(12) United States Patent
Larson et al.

(10) Patent No.: US 7,405,218 B2
(45) Date of Patent: Jul. 29, 2008

(54) ISOTHIAZOLE DERIVATIVES USEFUL AS ANTICANCER AGENTS

(75) Inventors: Eric R. Larson, Mystic, CT (US); Mark C. Noe, Mystic, CT (US); Thomas G. Gant, Niantic, CT (US)

(73) Assignees: Pfizer, Inc., New York, NY (US); OSI Pharmaceuticals, Inc., Melville, NY (US)

( * ) Notice: Subject to any disclaimer, the term of this patent is extended or adjusted under 35 U.S.C. 154(b) by 140 days.

(21) Appl. No.: 10/357,093

(22) Filed: Feb. 3, 2003

(65) Prior Publication Data

US 2003/0149048 A1 Aug. 7, 2003

Related U.S. Application Data

(62) Division of application No. 09/803,296, filed on Mar. 9, 2001, now Pat. No. 6,548,526, which is a division of application No. 09/316,837, filed on May 21, 1999, now Pat. No. 6,235,764.

(60) Provisional application No. 60/087,963, filed on Jun. 4, 1998.

(51) Int. Cl.
A61K 31/426 (2006.01)
A61K 31/427 (2006.01)
C07D 275/03 (2006.01)

(52) U.S. Cl. .................. 514/254.04; 514/326; 514/372; 544/367; 546/209; 548/213

(58) Field of Classification Search ................. 548/213; 546/209; 544/367; 514/372, 326, 254.04
See application file for complete search history.

(56) References Cited

U.S. PATENT DOCUMENTS

| 4,057,416 | A | 11/1977 | Gibbons | 71/90 |
| 4,059,433 | A | 11/1977 | Gibbons | 71/90 |
| 5,952,359 | A | 9/1999 | Godfrey | 514/369 |
| 6,235,764 | B1 | 5/2001 | Larson et al. | 514/372 |
| 6,548,526 | B2 * | 4/2003 | Larson et al. | 514/372 |

FOREIGN PATENT DOCUMENTS

| DE | 4425642 | 1/1996 |
| EP | 0578246 | 12/1994 |
| WO | 9220642 | 11/1992 |
| WO | 9921845 | 5/1999 |

OTHER PUBLICATIONS

Golub et al., Science, vol. 286, Oct. 15, 1999, pp. 531-537.*

* cited by examiner

*Primary Examiner*—Laura L Stockton
(74) *Attorney, Agent, or Firm*—Scully, Scott, Murphy & Presser, P.C.

(57) ABSTRACT

The present invention relates to compounds of the formula 1

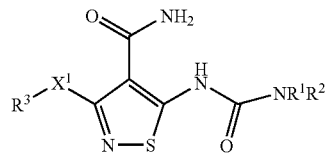

and to pharmaceutically acceptable salts, prodrugs and solvates thereof, wherein $X^1$, $R^1$, $R^2$ and $R^3$ are as defined herein. The invention also relates to pharmaceutical compositions containing the above compounds and to methods treating hyperproliferative disorders in mammals by administering the above compounds.

2 Claims, No Drawings

ISOTHIAZOLE DERIVATIVES USEFUL AS ANTICANCER AGENTS

This is a divisional application of U.S. application Ser. No. 09/803,296, filed Mar. 9, 2001, now U.S. Pat. No. 6,548,526 which is a divisional application of U.S. application Ser. Pat. No. 09/316,837, filed May 21, 1999, now U.S. Pat. No. 6,235,764, which claims the benefit of U.S. Provisional Application No. 60/087,963, filed Jun. 4, 1998, all of which are incorporated herein by reference.

BACKGROUND OF THE INVENTION

This invention relates to novel isothiazole derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

It is known that a cell may become cancerous by virtue of the transformation of a portion of its DNA into an oncogene (i.e. a gene that upon activation leads to the formation of malignant tumor cells). Many oncogenes encode proteins which are aberrant tyrosine kinases capable of causing cell transformation. Alternatively, the overexpression of a normal proto-oncogenic tyrosine kinase may also result in proliferative disorders, sometimes resulting in a malignant phenotype. It has been shown that certain tyrosine kinases may be mutated or overexpressed in many human cancers such as brain, lung, squamous cell, bladder, gastric, breast, head and neck, oesophageal, gynecological and thyroid cancers. Furthermore, the overexpression of a ligand for a tyrosine kinase receptor may result in an increase in the activation state of the receptor, resulting in proliferation of the tumor cells or endothelial cells. Thus, it is believed that inhibitors of receptor tyrosine kinases, such as the compounds of the present invention, are useful as selective inhibitors of the growth of mammalian cancer cells.

It is known that polypeptide growth factors, such as vascular endothelial growth factor (VEGF) having a high affinity to the human kinase insert-domain-containing receptor (KDR) or the murine fetal liver kinase 1 (FLK-1) receptor, have been associated with the proliferation of endothelial cells and more particularly vasculogenesis and angiogenesis. See PCT international application publication number WO 95/21613 (published Aug. 17, 1995). Agents, such as the compounds of the present invention, that are capable of binding to or modulating the KDR/FLK-1 receptor may be used to treat disorders related to vasculogenesis or angiogenesis such as diabetes, diabetic retinopathy, hemangioma, glioma, melanoma, Kaposi's sarcoma and ovarian, breast, lung, pancreatic, prostate, colon and epidermoid cancer.

Isothiazole derivatives useful as herbicides are referred to in U.S. Pat. Nos. 4,059,433 and 4,057,416, both assigned to FMC Corporation.

SUMMARY OF THE INVENTION

The present invention relates to compounds of the formula 1

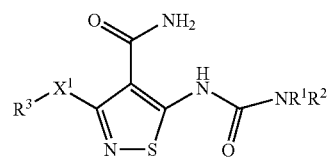

and to pharmaceutically acceptable salts, prodrugs and solvates thereof, wherein:

wherein $X^1$ is O or S;

$R^1$ is H, $C_1$-$C_{10}$ alkyl, $C_2$-$C_{10}$ alkenyl, $C_2$-$C_{10}$ alkynyl, —C(O)($C_1$-$C_{10}$ alkyl), —(CH$_2$)$_t$($C_6$-$C_{10}$ aryl), —(CH$_2$)$_t$(4-10 membered heterocyclic), —C(O)(CH$_2$)$_t$($C_6$-$C_{10}$ aryl), or —C(O)(CH$_2$)$_t$(5-10 membered heterocyclic), wherein t is an integer from 0 to 5; said alkyl group optionally includes 1 or 2 hetero moieties selected from O, S and —N($R^6$)— with the proviso that two O atoms, two S atoms, or an O and S atom are not attached directly to each other; said aryl and heterocyclic $R^1$ groups are optionally fused to a $C_6$-$C_{10}$ aryl group, a $C_5$-$C_8$ saturated cyclic group, or a 5-10 membered heterocyclic group; 1 or 2 carbon atoms in the foregoing heterocyclic moieties are optionally substituted by an oxo (=O) moiety; the —(CH$_2$)$_t$— moieties of the foregoing $R^1$ groups optionally include a carbon-carbon double or triple bond where t is an integer from 2 to 5; and the foregoing $R^1$ groups, except H, are optionally substituted by 1 to 3 $R^4$ groups;

$R^2$ is selected from the list of substituents provided in the definition of $R^1$, —SO$_2$(CH$_2$)$_t$($C_6$-$C_{10}$ aryl), —SO$_2$(CH$_2$)$_t$(5-10 membered heterocyclic), and —OR$^5$, t is an integer ranging from 0 to 5, the —(CH$_2$)$_t$— moieties of the foregoing $R^2$ groups optionally include a carbon-carbon double or triple bond where t is an integer from 2 to 5, and the foregoing $R^2$ groups are optionally substituted by 1 to 3 $R^4$ groups;

or $R^1$ and $R^2$ may be taken together with the nitrogen to which each is attached to form a 4-10 membered saturated monocyclic or polycyclic ring or a 5-10 membered heteroaryl ring, wherein said saturated and heteroaryl rings optionally include 1 or 2 heteroatoms selected from O, S and —N($R^6$)— in addition to the nitrogen to which $R^1$ and $R^2$ are attached, said —N($R^6$)— is optionally =N— or —N= where $R^1$ and $R^2$ are taken together as said heteroaryl group, said saturated ring optionally may be partially unsaturated by including 1 or 2 carbon-carbon double bonds, and said saturated and heteroaryl rings, including the $R^6$ group of said —N($R^6$)—, are optionally substituted by 1 to 3 $R^4$ groups;

$R^3$ is H, $C_1$-$C_{10}$ alkyl, $C_2$-$C_{10}$ alkenyl, $C_2$-$C_{10}$ alkynyl, —(CH$_2$)$_t$($C_6$-$C_{10}$ aryl), or —(CH$_2$)$_t$(5-10 membered heterocyclic), wherein t is an integer from 0 to 5; said alkyl group optionally includes 1 or 2 hetero moieties selected from O, S and —N($R^6$)— with the proviso that two O atoms, two S atoms, or an O and S atom are not attached directly to each other; said aryl and heterocyclic $R^3$ groups are optionally fused to a $C_6$-$C_{10}$ aryl group, a $C_5$-$C_8$ saturated cyclic group, or a 5-10 membered heterocyclic group; 1 or 2 carbon atoms in the foregoing heterocyclic moieties are optionally substituted by an oxo (=O) moiety; the —(CH$_2$)$_t$— moieties of the foregoing $R^3$ groups optionally include a carbon-carbon double or triple bond where t is an integer from 2 to 5, and the foregoing $R^3$ groups are optionally substituted by 1 to 5 $R^4$ groups;

each $R^4$ is independently selected from $C_1$-$C_{10}$ alkyl, $C_2$-$C_{10}$ alkenyl, $C_2$-$C_{10}$ alkynyl, halo, cyano, nitro, trifluoromethyl, trifluoromethoxy, azido, —OR$^5$, —C(O)R$^5$, —C(O)OR$^5$, —NR$^6$C(O)OR$^5$, —OC(O)R$^5$, —NR$^6$SO$_2$R$^5$, —SO$_2$NR$^5$R$^6$, —NR$^6$C(O)R$^5$, —C(O)NR$^5$R$^6$, —NR$^5$R$^6$, —S(O)$_j$R$^7$ wherein j is an integer ranging from 0 to 2, —SO$_3$H, —NR$^5$(CR$^6$R$^7$)$_t$OR$^6$, —(CH$_2$)$_t$($C_6$-$C_{10}$ aryl), —SO$_2$(CH$_2$)$_t$($C_6$-$C_{10}$ aryl), —S(CH$_2$)$_t$($C_6$-$C_{10}$ aryl), —O(CH$_2$)$_t$($C_6$-$C_{10}$ aryl), —(CH$_2$)$_t$(5-10 membered heterocyclic), and —(CR$^6$R$^7$)$_m$OR$^6$, wherein m is an integer from 1 to 5 and t is an integer from 0 to 5; said alkyl group optionally contains 1 or 2 hetero moieties selected from O, S and —N($R^6$)— with the proviso that two O atoms, two S atoms, or an O and S atom are not attached directly to each other; said aryl and heterocyclic $R^4$ groups are optionally fused to a $C_6$-$C_{10}$ aryl group, a $C_5$-$C_8$ saturated cyclic group, or a 5-10 membered heterocyclic group; 1 or 2 carbon atoms in the foregoing heterocyclic moieties are optionally substituted by an oxo (=O) moiety; and the alkyl, aryl and heterocyclic moieties of the foregoing $R^4$ groups are optionally substituted by 1 to 3 substituents independently selected from halo, cyano, nitro, trifluoromethyl, trifluoromethoxy, azido, —$NR^6SO_2R^5$, —$SO_2NR^5R^6$, —$C(O)R^5$, —$C(O)OR^5$, —$OC(O)R^5$, —$NR^6C(O)R^5$, —$C(O)NR^5R^6$, —$NR^5R^6$, —$(CR^6R^7)_mOR^6$ wherein m is an integer from 1 to 5, —$OR^5$ and the substituents listed in the definition of $R^5$;

each $R^5$ is independently selected from H, $C_1$-$C_{10}$ alkyl, —$(CH_2)_t(C_6$-$C_{10}$ aryl), and —$(CH_2)_t$(5-10 membered heterocyclic), wherein t is an integer from 0 to 5; said alkyl group optionally includes 1 or 2 hetero moieties selected from O, S and —$N(R^6)$— with the proviso that two O atoms, two S atoms, or an O and S atom are not attached directly to each other; said aryl and heterocyclic $R^5$ groups are optionally fused to a $C_6$-$C_{10}$ aryl group, a $C_5$-$C_8$ saturated cyclic group, or a 5-10 membered heterocyclic group; and the foregoing $R^5$ subsituents, except H, are optionally substituted by 1 to 3 substituents independently selected from halo, cyano, nitro, trifluoromethyl, trifluoromethoxy, azido, —$C(O)R^6$, —$C(O)OR^6$, —$CO(O)R^6$, —$NR^6C(O)R^7$, —$C(O)NR^6R^7$, —$NR^6R^7$, hydroxy, $C_1$-$C_6$ alkyl, and $C_1$-$C_6$ alkoxy; and, each $R^6$ and $R^7$ is independently H or $C_1$-$C_6$ alkyl;

with the proviso that said compound of formula 1 is not 1-methyl-3-(4-carbamoyl-3-ethoxy-5-isothiazolyl)urea, 1,1-dimethyl-3-(4-carbamoyl-3-ethoxy-5-isothiazolyl)urea, 1-methyl-3-(4-carbamoyl-3-propoxy-5-isothiazolyl)urea, 1-methyl-3-(4-carbamoyl-3-(methylthio)-5-isothiazolyl)urea, 1-methyl-3-(4-carbamoyl-3-(ethylthio)-5-isothiazolyl)urea, 1,1-dimethyl-3-(4-carbamoyl-3-(ethylthio)-5-isothiazolyl)urea, 1-methyl-3-(4-carbamoyl-3-(propylthio)-5-isothiazolyl)urea, 1,1-dimethyl-3-(4-carbamoyl-3-(propylthio)-5-isothiazolyl)urea, or 1-methyl-3-(4-carbamoyl-3-(isopropylthio)-5-isothiazolyl)urea.

Preferred compounds include those of formula 1 wherein $R^2$ is H and $R^1$ is $C_1$-$C_{10}$ alkyl optionally substituted by 1 or 2 substituents independently selected from —$NR^5R^6$, —$NR^5(CR^6R^7)_tOR^6$ and —$(CH_2)_t$(5-10 membered heterocyclic) wherein t is an integer from 0 to 5. Specific preferred $R^1$ groups include propyl, butyl, pentyl and hexyl optionally substituted by dimethylamino, hydroxy, pyrrolidinyl, morpholino, and ethyl-(2-hydroxy-ethyl)-amino.

Other preferred compounds include those of formula 1 wherein $R^2$ is H and $R^1$ is —$(CH_2)_t$(5-10 membered heterocyclic), wherein t is an integer from 0 to 5; said heterocyclic group is optionally fused to a $C_6$-$C_{10}$ aryl group, a $C_5$-$C_8$ saturated cyclic group, or a 5-10 membered heterocyclic group; and said $R^1$ group, including the optionally fused portions of said $R^1$ group, is optionally substituted by 1 or 2 substituents independently selected from $C_1$-$C_4$ alkyl, hydroxy and hydroxymethyl. Specific preferred heterocyclic groups of said $R^1$ group are morpholino, pyrrolidinyl, imidazolyl, piperazinyl, piperidinyl, and 2,5-diaza-bicyclo[2.2.1]hept-2-yl, the t variable of said $R^1$ group ranges from 2 to 5, and said heterocyclic groups are optionally substituted by hydroxy, hydroxymethyl and methyl.

Other preferred compounds include those of formula 1 wherein $R^3$ is —$(CH_2)_t(C_6$-$C_{10}$ aryl) wherein t is an integer from 1 to 3 and said $R^3$ group is optionally substituted by 1 to 4 $R^4$ groups. Specific preferred $R^3$ groups include benzyl optionally substituted by 1 to 4 substituents independently selected from halo and $C_1$-$C_4$ alkyl. More specific preferred $R^3$ groups include benzyl substituted by 1 to 4 substituents independently selected from methyl, fluoro, chloro and bromo.

Specific embodiments of the present invention include the following compounds:

5-{3-[3-(4-Methyl-piperazin-1-yl)-propyl]-ureido}-3-(2,3,6-trifluoro-4-methyl-benzyloxy)-isothiazole-4-carboxylic acid amide;

3-(4-Chloro-2,6-difluoro-benzyloxy)-5-(3-{4-[ethyl-(2-hydroxy-ethyl)-amino]-butyl}-ureido)-isothiazole-4-carboxylic acid amide;

3-(2-Fluoro-4-methyl-benzyloxy)-5-{3-[3-(4-methyl-piperazin-1-yl)-propyl]-ureido}-isothiazole-4-carboxylic acid amide;

3-(2,5-Difluoro-4-methyl-benzyloxy)-5-(3-4-[4-(2-hydroxy-ethyl)-piperazin-1-yl]-butyl}-ureido)-isothiazole-4-carboxylic acid amide;

3-(2,5-Difluoro-4-methyl-benzyloxy)-5-[3-(6-dimethylamino-hexyl)-ureido]-isothiazole-4-carboxylic acid amide;

3-(2-Fluoro-4-methyl-benzyloxy)-5-[3-(5-isopropylaminopentyl)-ureido]-isothiazole-4-carboxylic acid amide;

3-(4-Chloro-2,6-difluoro-benzyloxy)-5-[3-(4-pyrrolidin-1-yl-butyl)-ureido]-isothiazole-4-carboxylic acid amide;

3-(4-Chloro-2,6-difluoro-benzyloxy)-5-{3-[3-(4-methyl-piperazin-1-yl)-propyl]-ureido}-isothiazole-4-carboxylic acid amide;

3-(4-Chloro-2,6-difluoro-benzyloxy)-5-{3-[-(1-methyl-pyrrolidin-2-yl)-ethyl]-ureido}-isothiazole-4-carboxylic acid amide;

3-(2,6-Difluoro-4-methyl-benzyloxy)-5-[3-(4-pyrrolidin-1-yl-butyl)-ureido]-isothiazole-4-carboxylic acid amide;

3-(2,6-Difluoro-4-methyl-benzyloxy)-5-[3-{4-[4-(2-hydroxy-ethyl)-piperazin-1-yl]-butyl}-ureido)-isothiazole-4-carboxylic acid amide;

3-(4-Chloro-2,6-difluoro-benzyloxy)-5-[3-(3-hydroxy-5-pyrrolidin-1-yl)-pentyl)-ureido}-isothiazole-4-carboxylic acid amide;

3-(2,5-Difluoro-4-methyl-benzyloxy)-5-{3-[4-(3,4-dihydroxy-pyrrolidin-1-yl)-butyl]-ureido}-isothiazole-4-carboxylic acid amide;

3-(4-Chloro-2,6-difluoro-benzyloxy)-5-{3-[4-(3,4-dihydroxy-pyrrolidin-1-yl)-butyl]-ureido}-isothiazole-4-carboxylic acid amide;

3-(2,5-Difluoro-4-methyl-benzyloxy)-5-{3-[4-(2-hydroxymethyl-pyrrolidin-1-yl)-butyl]-ureido}-isothiazole-4-carboxylic acid amide;

3-(4-Chloro-2,6-difluoro-benzyloxy)-5-{3-[4-(2-hydroxymethyl-pyrrolidin-1-yl)-butyl-]-ureido}-isothiazole-4-carboxylic acid amide;

3-(2,5-Difluoro-4-methyl-benzyloxy)-5-{3-[4-(3-hydroxy-pyrrolidin-1-yl)-butyl]-ureido}-isothiazole-4-carboxylic acid amide;

3-(4-Bromo-2,6-difluoro-benzyloxy)-5-[3-(4-pyrrolidin-1-yl-butyl)-ureido}-isothiazole-4-carboxylic acid amide;

mesylate salt of 3-(4-Bromo-2,6-difluoro-benzyloxy)-5-[3-(4-pyrrolidin-1-yl-butyl)-ureido}-isothiazole-4-carboxylic acid amide;

3-(2,6-Difluoro-4-methyl-benzyloxy)-5-[3-(4-hydroxy-5-piperidin-1-yl-pentyl)-ureido]-isothiazole-4-carboxylic acid amide;

3-(2,5-Difluoro-4-methyl-benzyloxy)-5-{3-[4-(3-hydroxy-5-piperidin-1-yl-pentyl)-ureido]-isothiazole-4-carboxylic acid amide;

3-(4-Chloro-2,6-difluoro-benzyloxy)-5-{3-[4-(2-hydroxymethyl-piperidin-1-yl)-butyl]-ureido}-isothiazole-4-carboxylic acid amide;

3-(2,5-Difluoro-4-methyl-benzyloxy)-5-(3-{4-[ethyl-(2-hydroxy-ethyl)-amino]-butyl}-ureido)-isothiazole-4-carboxylic acid amide;

3-(4-Chloro-2,6-difluoro-benzyloxy)-5-[3-(5-hydroxy-6-piperidin-1-yl)-hexyl)-ureido}-isothiazole-4-carboxylic acid amide;
3-(4-Bromo-2,3,6-trifluoro-benzyloxy)-5-{3-[3-(4-methyl-piperazin-1-yl)-propyl]-ureido}-isothiazole-4-carboxylic acid amide;
3-(2,6-Difluoro-4-methyl-benzyloxy)-5-{3-[3-(4-methyl-piperazin-1-yl)-propyl]-ureido}-isothiazole-4-carboxylic acid amide;
hydrochloride salt of 3-(4-Bromo-2,6-difluoro-benzyloxy)-5-[3-(4-pyrrolidin-1-yl-butyl)-ureido}-isothiazole-4-carboxylic acid amide;
3-(2,6-Difluoro-4-methyl-benzyloxy)-5-[3-(3-hydroxy-5-pyrrolidin-1-yl-pentyl)-ureido]-isothiazole-4-carboxylic acid amide;
5-[3-(4-Pyrrolidin-1-yl-butyl)-ureido]-3-(2,3,6-trifluoro-4-methyl-benzyloxy)-isothiazole-4-carboxylic acid amide;
5-[3-(3-Hydroxy-5-pyrrolidin-1-yl-pentyl)-ureido]-3-(2,3,6-trifluoro-4-methyl-benzyloxy)-isothiazole-4-carboxylic acid amide;
3-(4-Chloro-2,6-difluoro-benzyloxy)-5-{3-[3-(5-methyl-2,5-diazabicyclo[2.2.1]hept-2-yl)-propyl]-ureido}-isothiazole-4-carboxylic acid amide;
3-(4-Chloro-2,3,6-trifluoro-benzyloxy)-5-{3-[3-(5-methyl-2,5-diaza-bicyclo[2.2.1]hept-2-yl)-propyl]-ureido}-isothiazole-4-carboxylic acid amide;
3-(4-Chloro-2,3,6-trifluoro-benzyloxy)-5-{3-[2-(1-methyl-pyrrolidin-2-yl)-ethyl]-ureido}-isothiazole-4-carboxylic acid amide;
3-(4-Chloro-2,3,6-trifluoro-benzyloxy)-5-[3-(4-pyrrolidin-1-yl-butyl)-ureido]-isothiazole-4-carboxylic acid amide;
3-(4-Chloro-2,3,6-trifluoro-benzyloxy)-5-{3-[4-(2-hydroxymethyl-pyrrolidin-1-yl)-butyl]-ureido}-isothiazole-4-carboxylic acid amide;
5-{3-[2-(1-Methyl-pyrrolidin-2-yl)-ethyl]-ureido}-3-(2,3,6-trifluoro-4-methyl-benzyloxy)-isothiazole-4-carboxylic acid amide;
5-[3-(4-Dimethylamino-butyl)-ureido]-3-(2,3,6-trifluoro-4-methyl-benzyloxy)-isothiazole-4-carboxylic acid amide;
5-[3-(3-Dimethylamino-propyl)-ureido]-3-(2,3,6-trifluoro-4-methyl-benzyloxy)-isothiazole-4-carboxylic acid amide;
5-[3-(3-Hydroxy-5-isopropylamino-pentyl)-ureido]-3-(2,3,6-trifluoro-4-methyl-benzyloxy)-isothiazole-4-carboxylic acid amide;
5-[3-(3-Isopropylamino-propyl)-ureido]-3-(2,3,6-trifluoro-4-methyl-benzyloxy)-isothiazole-4-carboxylic acid amide;
5-{3-[4-(4-Methyl-piperazin-1-yl)-butyl]-ureido}-3-(2,3,6-trifluoro-4-methyl-benzyloxy)-isothiazole-4-carboxylic acid amide;
5-(3-{4-[4-(2-Hydroxy-ethyl)-piperazin-1-yl]-butyl}-ureido)-3-(2,3,6-trifluoro-4-methyl-benzyloxy)-isothiazole-4-carboxylic acid amide;
5-[3-(3-Pyrrolidin-1-yl-propyl)-ureido]-3-(2,3,6-trifluoro-4-methyl-benzyloxy)-isothiazole-4-carboxylic acid amide;
5-[3-(4-Hydroxy-5-piperidin-1-yl-pentyl)-ureido]-3-(2,3,6-trifluoro-4-methyl-benzyloxy)-isothiazole-4-carboxylic acid amide;
3-(4Chloro-2,6-difluoro-benzyloxy)-5-[3-(4-imidazol-1-yl-butyl)-ureido]-isothiazole-4-carboxylic acid amide;
5-(3-{4-[Ethyl-(2-hydroxy-ethyl)-amino]-butyl-ureido)-3-(2,3,6-trifluoro-4-methyl-benzyloxy)-isothiazole-4-carboxylic acid amide;
3-(4-Chloro-(2,3,6-trifluoro-benzyloxy)-5-{3-[4-(2-hydroxmethyl-piperidin-1-yl)-butyl]-ureido}-isothiazole-4-carboxylic acid amide;
3-(4-Chloro-2,3,6-trifluoro-benzyloxy)-5-[3-(3-hydroxy-5-pyrrolidin-1-yl-pentyl)-ureido]-isothiazole-4-carboxylic acid amide;
3-(4-Bromo-2,6-difluoro-benzyloxy)-5-{3-[3-(4-methyl-piperazin-1-yl)-propyl]-ureido}-isothiazole-4-carboxylic acid amide;
3-(2,6-Difluoro-4-methyl-benzyloxy)-5-{3-[2-(1-methyl-pyrrolidin-2-yl)-ethyl]-ureido}-isothiazole-4-carboxylic acid amide;
3-(2,6-Difluoro-4-methyl-benzyloxy)-5-[3-(4-dimethylamino-butyl)-ureido}-isothiazole-4-carboxylic acid amide;
3-(2,6-Difluoro-4-methyl-benzyloxy)-5-[3-(3-dimethylamino-propyl)-ureido]-isothiazole-4-carboxylic acid amide;
3-(4-Bromo-2,3,6-trifluoro-benzyloxy)-5-[3-(4-pyrrolidin-1-yl-butyl)-ureido]-isothiazole-4-carboxylic acid amide;
3-(4-Chloro-2,3,6-trifluoro-benzyloxy)-5-[3-(4-imidazol-1-yl-butyl)-ureido]-isothiazole-4-carboxylic acid amide;
3-(4-Chloro-2,3,6-difluoro-benzyloxy)-5-(3-{3-[ethyl-(2-hydroxy-ethyl)-amino]-propyl}-ureido)-isothiazole-4-carboxylic acid amide;
3-(4-Chloro-2,3,6-trifluoro-benzyloxy)-5-(3-{3-[ethyl-(2-hydroxy-ethyl)-amino]-propyl}-ureido)-isothiazole-4-carboxylic acid amide;
5-[3-(3-Methylamino-propyl)-ureido]-3-(2,3,6-trifluoro-4-methyl-benzyloxy)-isothiazole-4-carboxylic acid amide;
5-[3-(3-Amino-propyl)-3-methyl-ureido]-3-(2,3,6-trifluoro-4-methyl-benzyloxy)-isothiazole-4-carboxylic acid amide;
5-[3-(4-Diethylamino-butyl)-ureido]-3-(2,3,6-trifluoro-4-methyl-benzyloxy)-isothiazole-4-carboxylic acid amide;
3-(2,6-Difluoro-4-methyl-benzyloxy)-5-[3-(3-pyrrolidin-1-yl-propyl)-ureido]-isothiazole-4-carboxylic acid amide;
3-(3-Chloro-2,6-difluoro-4-methyl-benzyloxy)-5-[3-(4-dimethylamino-butyl)-ureido]-isothiazole-4-carboxylic acid amide;
5-(3-{4-[Bis-(2-hydroxy-ethyl)-amino]-butyl}-ureido)-3-(2,6-difluoro-4-methyl-benzyloxy)-isothiazole-4-carboxylic acid amide;
and the pharmaceutically acceptable salts and hydrates of the foregoing compounds.

The invention also relates to a pharmaceutical composition for the treatment of a hyperproliferative disorder in a mammal which comprises a therapeutically effective amount of a compound of formula 1, or a pharmaceutically acceptable salt or hydrate thereof, and a pharmaceutically acceptable carrier. In one embodiment, said pharmaceutical composition is for the treatment of cancer such as brain, lung, squamous cell, bladder, gastric, pancreatic, breast, head, neck, renal, prostate, colorectal, oesophageal, gynecological (such as ovarian) or thyroid cancer. In another embodiment, said pharmaceutical composition is for the treatment of a non-cancerous hyperproliferative disorder such as benign hyperplasia of the skin (e.g., psoriasis) or prostate (e.g., benign prostatic hypertropy (BPH)).

The invention also relates to a pharmaceutical composition for the treatment of pancreatitis or kidney disease (including proliferative glomerulonephritis and diabetes-induced renal disease) in a mammal which comprises a therapeutically effective amount of a compound of formula 1, or a pharmaceutically acceptable salt or hydrate thereof, and a pharmaceutically acceptable carrier.

The invention also relates to a pharmaceutical composition for the prevention of blastocyte implantation in a mammal which comprises a therapeutically effective amount of a compound of formula 1, or a pharmaceutically acceptable salt or hydrate thereof, and a pharmaceutically acceptable carrier.

The invention also relates to a pharmaceutical composition for treating a disease related to vasculogenesis or angiogenesis in a mammal which comprises a therapeutically effective amount of a compound of formula 1, or a pharmaceutically acceptable salt or hydrate thereof, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal which comprises administering to said mammal a therapeutically effective amount of the compound of formula 1, or a pharmaceutically acceptable salt or hydrate thereof. In one embodiment, said method relates to the treatment of cancer such as brain, squamous cell, bladder, gastric, pancreatic, breast, head, neck, oesophageal, prostate, colorectal, lung, renal, gynecological (such as ovarian) or thyroid cancer. In another embodiment, said method relates to the treatment of a non-cancerous hyperproliferative disorder such as benign hyperplasia of the skin (e.g., psoriasis) or prostate (e.g., benign prostatic hypertropy (BPH)).

The invention also relates to a method for the treatment of a hyperproliferative disorder in a mammal which comprises administering to said mammal a therapeutically effective amount of a compound of formula 1, or a pharmaceutically acceptable salt or hydrate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The invention also relates to a method of treating pancreatitis or kidney disease in a mammal which comprises administering to said mammal a therapeutically effective amount of a compound of formula 1, or a pharmaceutically acceptable salt or hydrate thereof.

The invention also relates to a method of preventing blastocyte implantation in a mammal which comprises administering to said mammal a therapeutically effective amount of a compound of formula 1, or a pharmaceutically acceptable salt or hydrate thereof.

The invention also relates to a method of treating diseases related to vasculogenesis or angiogenesis in a mammal which comprises administering to said mammal an effective amount of a compound of formula 1, or a pharmaceutically acceptable salt or hydrate thereof. In one embodiment, said method is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, macular degeneration, hemangioma, glioma, melanoma, Kaposi's sarcoma and ovarian, breast, lung, pancreatic, prostate, colon and epidermoid cancer.

Further the compounds of the present invention may be used as contraceptives in mammals.

Patients that can be treated with the compounds of formulas 1, and the pharmaceutically acceptable salts and hydrates of said compounds, according to the methods of this invention include, for example, patients that have been diagnosed as having psoriasis, BPH, lung cancer, bone cancer, pancreatic cancer, skin cancer, cancer of the head and neck, cutaneous or intraocular melanoma, uterine cancer, ovarian cancer, rectal cancer or cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

The present invention also relates to intermediates selected from the group consisting of (2,6-difluoro-4-methyl-phenyl)-methanol, (2,3,6-trifluoro-4-methyl-phenyl)-methanol, (4-bromo-2,6-difluoro-phenyl)-methanol, (4-bromo-2,3,6-trifluoro-phenyl)-methanol, (4-chloro-2,6-difluoro-phenyl)-methanol, (3-chloro-2,6-difluoro-phenyl)-methanol, and (4-chloro-2,3,6-trifluoro-phenyl)-methanol.

The present invention also relates to an intermediate selected from the group consisting of:

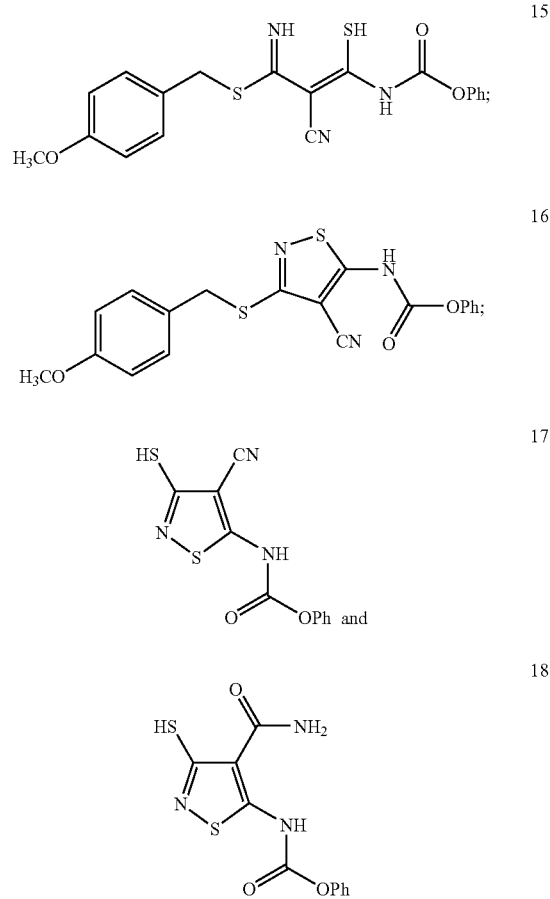

The present invention also relates to an intermediate selected from the group consisting of:

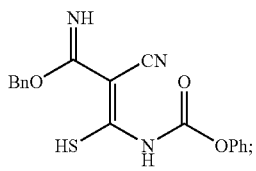

22

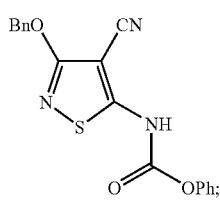

23

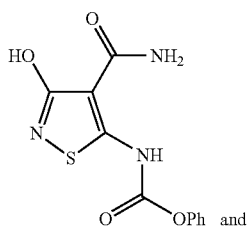

24

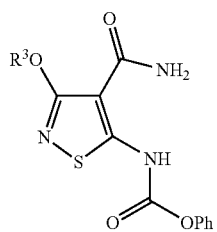

25 wherein $R^3$ is as defined above.

The present invention also relates to a method of preparing a compound of formula 1 which comprises either (a) treating a compound of formula 18

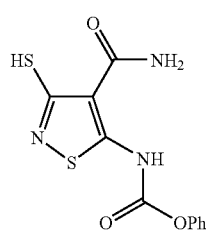

18 with a compound of the formula $R^3$—X wherein X is a halo group and $R^3$ is as defined above, and treating the resulting compound with a compound of the formula $R^1R^2NH$ wherein $R^1$ and $R^2$ are as defined above; or, (b) treating a compound of the formula 25

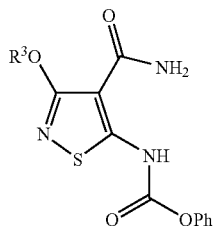

25 wherein $R^3$ is as defined above, with a compound of the formula $R^1R^2NH$ wherein $R^1$ and $R^2$ are as defined above.

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. It is understood that for cyclic moieties at least three carbon atoms are required in said alkyl group.

The term "alkenyl", as used herein, unless otherwise indicated, includes monovalent hydrocarbon radicals having at least one carbon-carbon double bond and also having straight, cyclic or branched moieties as provided above in the definition of "alkyl".

The term "alkynyl", as used herein, unless otherwise indicated, includes monovalent hydrocarbon radicals having at least one carbon-carbon triple bond and also having straight, cyclic or branched moieties as provided above in the definition of "alkyl".

The term "alkyoxy", as used herein, unless otherwise indicated, includes O-alkyl groups wherein "alkyl" is as defined above.

The term "aryl", as used herein, unless otherwise indicated, includes an organic radical derived from an aromatic hydrocarbon by removal of one hydrogen, such as phenyl or naphthyl.

The term "4-10 membered heterocyclic", as used herein, unless otherwise indicated, includes aromatic and non-aromatic heterocyclic groups containing one or more heteroatoms each selected from O, S and N, wherein each heterocyclic group has from 4-10 atoms in its ring system. Non-aromatic heterocyclic groups include groups having only 4 atoms in their ring system, but aromatic heterocyclic groups must have at least 5 atoms in their ring system. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo [3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The phrase "pharmaceutically acceptable salt(s)", as used herein, unless otherwise indicated, includes salts of acidic or basic groups which may be present in the compounds of formula 1. The compounds of formula 1 that are basic in nature are capable of forming a wide variety of salts with various inoroanic and organic acids. The acids that may be used to prepare pharmaceutically acceptable acid addition salts of such basic compounds of formula 1 are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formula 1 that are acidic in nature, are capable of forming base salts with various pharmacologically acceptable cations. Examples of such salts include the alkali metal or alkaline earth metal salts and particularly, the sodium and potassium salts.

Certain compounds of formula 1 may have asymmetric centers and therefore exist in different enantiomeric forms. This invention relates to the use of all optical isomers and stereoisomers of the compounds of formula 1 and mixtures thereof. The compounds of formula 1 may also exist as tautomers. This invention relates to the use of all such tautomers and mixtures thereof.

The subject invention also includes isotopically-labelled compounds, and the pharmaceutically acceptable salts thereof, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing and methods of treating bacterial infections through administering prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxy carbonyls, as outlined in D. Fleisher, R. Bong, B. H. Stewart, Advanced Drug Delivery Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., J. Medicinal Chemistry (1996) 39, 10.

DETAILED DESCRIPTION OF THE INVENTION

Compounds of the formula 1 and their pharmaceutically acceptable salts and solvates may be prepared as described below. Unless otherwise indicated, $R^1$, $R^2$ and $R^3$ are as defined above.

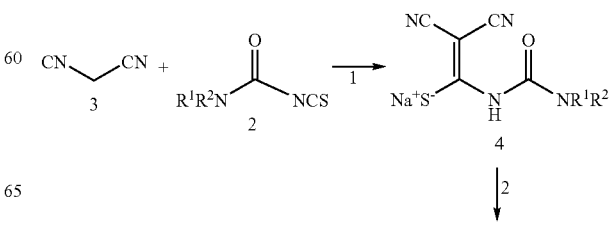

Scheme 1

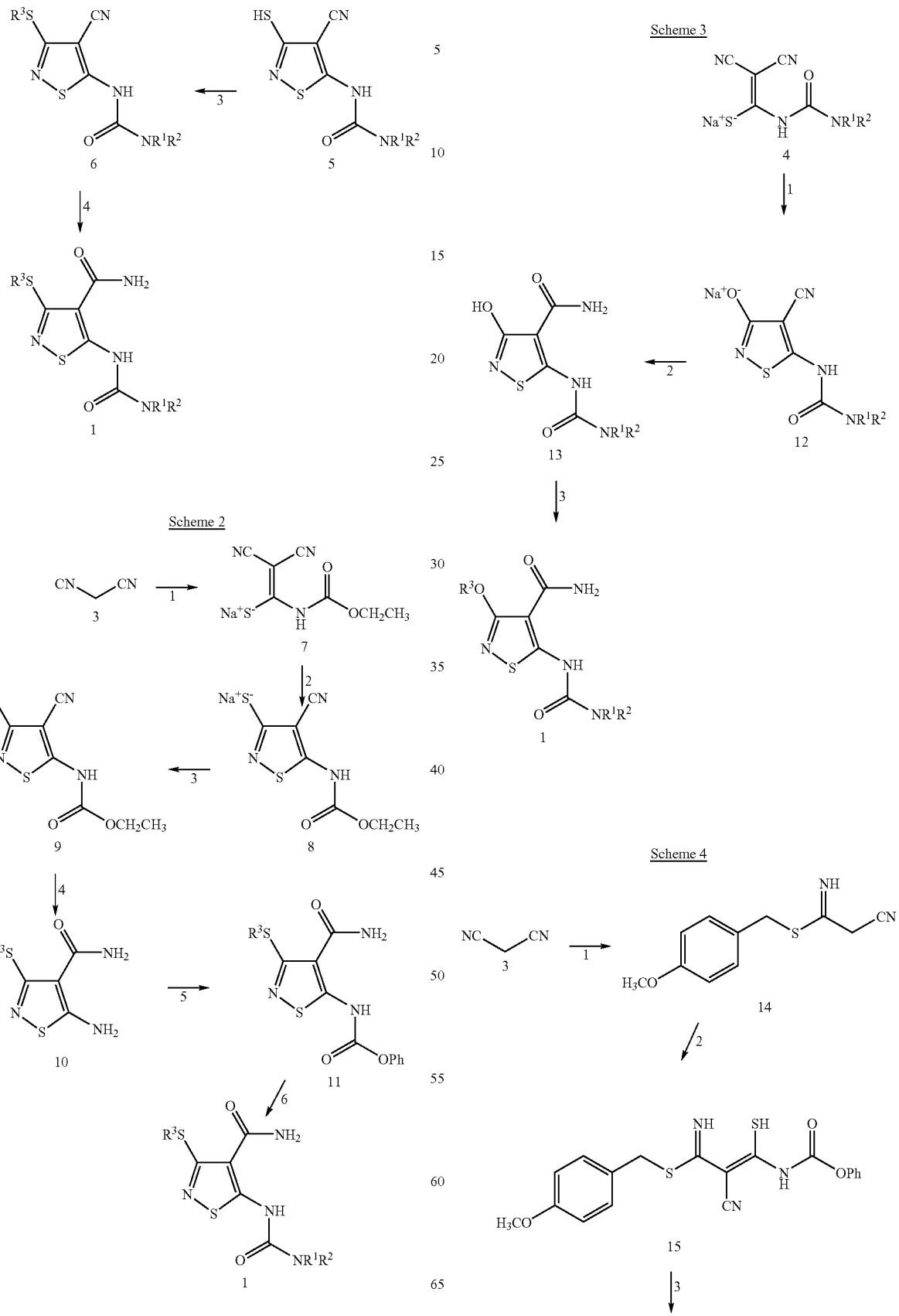

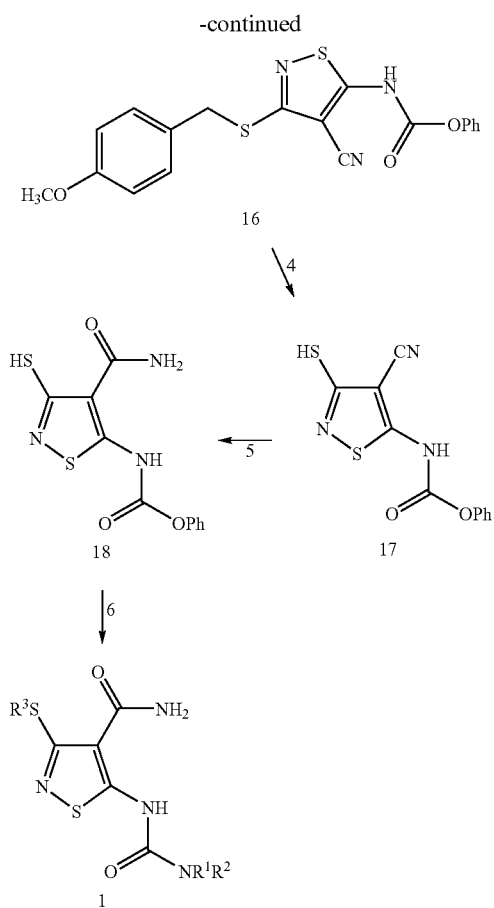
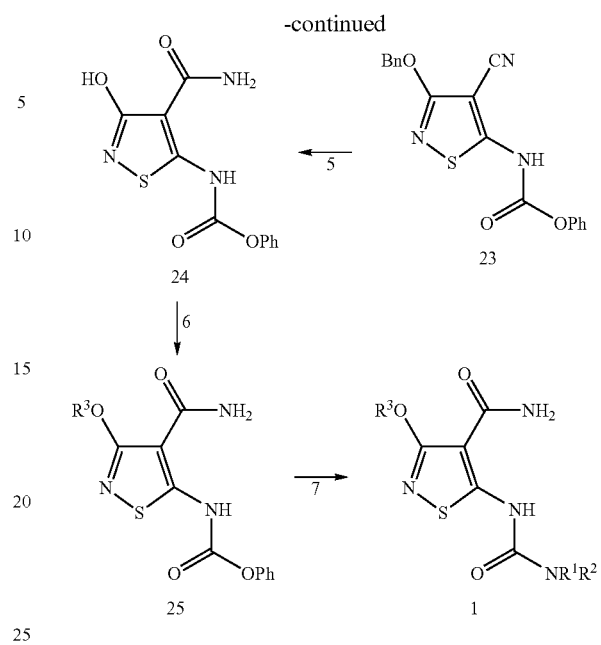
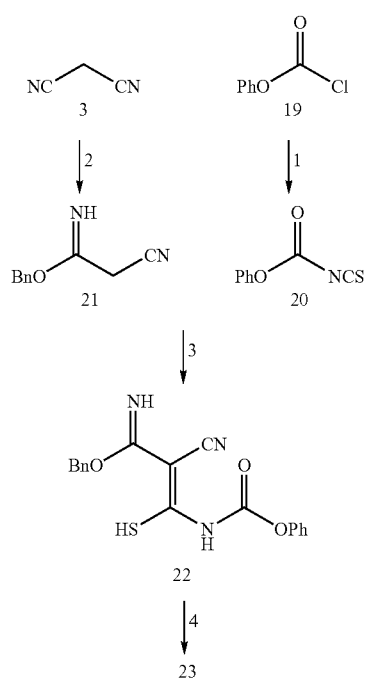

The compounds of the present invention are readily prepared by following the procedures outlined in the schemes illustrated above and typical synthetic procedures familiar to those skilled in the art. Scheme 1 illustrates the condensation of malononitrile with an isocyanate, oxidation with sulfur, alkylation with an $R^3$ containing compound, and hydration of the nitrile to provide the final compound. In step 1 of Scheme 1, the compound of formula 4 may be prepared by treating the compound of formula 3 and the compound of formula 2 ($R^1$ and $R^2$ are not H but otherwise are as defined above) with a suitably strong base, such as an alkoxide base, preferably sodium ethoxide, in a protic solvent, such as an alcohol, preferably ethanol, at a temperature ranging from −20° C. to 50° C., preferably 0° C. to 25° C., over a period of about 12 to 24 hours. In step 2 of Scheme 1, the compound of formula 5 may be prepared by treating the compound of formula 4 with sulfur (about 1 equivalent to excess) in a polar solvent, such as an alcoholic solvent, preferably methanol, at a temperature ranging from 25° C. to 80° C., preferably about 65° C., for a period of about 12 to 48 hours, preferably about 24 hours. In step 3 of Scheme 1, the compound of formula 6 may be prepared by treating the compound of formula 5 with an $R^3$-containing electrophile, such as a halide, preferably a chloride, bromide or iodide of such compound, in a polar solvent, preferably tetrahydrofuran (THF) or N,N-dimethylformamide (DMF), using about 1 to 5 equivalent, preferably a bit over 1 equivalent, and a base, such as a tertiary amine base, preferably diisopropylethylamine, for a period of about 12 to 48 hours, preferably about 24 hours, at a temperature ranging from 0° C. to 80° C., preferably about 25° C. In step 4 of Scheme 1, the compound of formula 1 (wherein $X^1$ is S) may be prepared by treating the compound of formula 6 under strongly acidic conditions, such as concentrated sulfuric acid, for a period of about 1 to 12 hours, preferably about 1.5 hours, at a temperature ranging from 25° C. to 100° C., preferably about 25° C., or under basic conditions, such as with aqueous sodium hydroxide (10%), for a period ranging from 6 to 24 hours at a temperature ranging from 25° C. to 120° C., preferably about 100° C.

Scheme 2 illustrates another method of preparing the compounds of formula 1 wherein $X^1$ is S. In step 1 of Scheme 2, the compound of formula 7 may be prepared by condensation of the compound of formula 3 with an alkoxycarbonyl isothiocyanate, such as ethoxy carbonyl isothiocyanate, in the presence of a strong base, such as an alkoxide base, preferably sodium ethoxide, in a polar solvent, such as an alcoholic solvent, preferably ethanol, for a period ranging from 12 to 24 hours at a temperature ranging from about 0° C. to 30° C. In step 2 of Scheme 2, the compound of formula 8 may be prepared by oxidative cyclization of the compound of formula 7 by treating the compound of formula 7 with about 1 equivalent of sulfur in an alcoholic solvent, such as methanol, at a temperature ranging from about 50° C. to 80° C., preferably about 65° C., for a period ranging from 24 to 48 hours. In step 3 of Scheme 2, the compound of formula 9 may be prepared by treating the compound of formula 8 with an $R^3$-containing electrophile, such as a halide, preferably the chloride, bromide or iodide of such compound, in a polar solvent, such as THF, at a temperature ranging from 25° C. to 40° C. for a period ranging from 12 to 24 hours. In step 4 of Scheme 2, the compound of formula 10 may be prepared by hydrolysing the compound of formula 9 with a suitably strong acid, such as concentrated sulfuric acid, at a temperature ranging from 80° C. to 120° C. for a period of about 6 to 18 hours. In step 5 of Scheme 2, the compound of formula 11 (wherein Ph is phenyl) may be prepared by treating the compound of formula 10 with an aryl or alkyl chloroformate, such as phenyl chloroformate, and a suitably strong base, such as pyridine, in a polar aprotic solvent, preferably THF or $CH_2Cl_2$, at a temperature ranging from 25° C. to 40° C. for a period ranging from 12 to 24 hours. In step 6 of Scheme 2, the compound of formula 1 (wherein $X^1$ is S) may be prepared by treating the compound of formula 11 with an excess (about 1.1 to 6 equivalents) of a primary or secondary amine of the formula $R^1R^2NH$ in a polar aprotic solvent, such as THF or a THF/DMF mixture, at a temperature ranging from 23° C. to 60° C. for a period ranging from 6 to 24 hours.

Scheme 3 illustrates a method of preparing the compounds of formula 1 wherein $X^1$ is O. The starting compound of formula 4 may be prepared as described above with reference to Scheme 1. In step 1 of Scheme 3, a solution of the salt of formula 4 in an inert solvent containing water or, preferably, in water alone, is treated with an oxidizing reagent, preferably dihydrogen peroxide. The mixture is held at a temperature and time sufficient to effect dissolution and cyclization, preferably at reflux for about 15 minutes, and then cooled to provide the compound of formula 12. In step 2 of Scheme 3, the compound of formula 12 is added to an acid solution, preferably concentrated sulfuric acid, followed by water sufficient to effect hydration, preferably about 10 equivalents, and is stirred at a temperature ranging from –20° C. and 100° C., preferably ambient temperature, for a period to effect hydration, preferably overnight. The mixture is then treated with water or, preferably, ice to provide the compound of formula 13. In step 3 of Scheme 3, the compound of formula 13 is treated with a base, preferably potassium tert-butoxide, in an inert solvent, preferably DMF, at a temperature ranging from –78° C. to 100° C., preferably ambient temperature. To this mixture is added an $R^3$ containing electrophile, such as an $R^3$ containing alkyl halide or sulfonate, preferably an iodide or bromide of such compound. The mixture is stirred until the reaction is complete as judged by TLC analysis to provide the compound of formula 1 (wherein $X^1$ is O).

Scheme 4 illustrates another method of preparing the compounds of formula 1 wherein $X^1$ is S. In step 1 of Scheme 4, the procedure follows the synthetic procedure outlined in M. Yokoyama and K. Sato, *Synthesis,* 813 (1988). Following this, the compound of formula 3 is treated with an alkyl thiol, such as 4-methoxy benzyl mercaptan, and a suitably strong base, such as sodium hydroxide, in a polar solvent, such as an alcohol/water mixture, preferably 1:1 ethanol/water, at a temperature ranging from –10° C. to 30° C., preferably about 0° C., for a period ranging from 2 to 6 hours, preferably about 3 hours, to provide the compound of formula 14. In step 2 of Scheme 4, the compound of formula 15 (Ph is phenyl) may be prepared by treating the compound of formula 14 with an alkoxy carbonyl isothiocyanate, such as phenoxy carbonyl isothiocyanate, in an aprotic solvent, such as ethyl acetate, at about 0° C. for about 12 to 36 hours. In step 3 of Scheme 4, the compound of formula 16 may be prepared by treating the compound of formula 15 with an oxidizing agent, such as bromine or iodine, preferably iodine, and a mild base, such as pyridine, in a polar solvent, such as acetonitrile, for about 1 hour at about 0° C. In step 4 of Scheme 4, the compound of formula 17 may be prepared by deprotection of the 4-methoxy benzyl group by treating the compound of formula 16 with mercuric acetate, about 1 equivalent, in the presence of an acid, preferably trifluoroacetic acid (TFA), with an excess of anisole, preferably 10 equivalents, at a temperature ranging from 0° C. to ambient temperature for a period ranging from 10 to 24 hours. In step 5 of Scheme 4, the compound of formula 18 may be prepared by hydration of the compound of formula 17 with a suitably strong acid, such as concentrated sulfuric acid, at a temperature ranging from 15° C. to 80° C., preferably ambient temperature, for a period ranging from 12 to 24 hours, preferably 18 hours. In step 6 of Scheme 4, the compound of formula 1 may be prepared by treating the compound of formula 18 with an $R^3$-containing electrophile, such as a halide, preferably the chloride, bromide or iodide of such compound, and a suitably strong base, such as diisopropyl ethyl amine, in a polar solvent, preferably DMF, at a temperature ranging from 0° C. to 50° C., preferably 25° C., for a period ranging from 12 to 24 hours. The resulting compound is then treated with a primary or secondary amine of the formula $R^1R^2NH$ (about 1.1 to 6 equivalents) in a THF/DMF mixture at a temperature ranging from 25° C. to 65° C. for a period ranging from 18 to 36 hours.

Scheme 5 illustrates another method of preparing a compound of formula 1 wherein $X^1$ is O. In step 1 of Scheme 5, a mixture of a thiocyanate salt, preferably potassium thiocyanate, in an inert solvent, preferably ethyl acetate, is stirred, preferably vigorously, under an inert atmosphere, overnight to powder the salt. This mixture is then treated with an aryl chloroformate of the formula 19 (Ph is phenyl) and the resulting mixture is stirred at a temperature ranging from –40° C. to ambient temperature, preferably about 5° C., for a period sufficient to effect reaction, preferably about 8 hours. The solid byproduct is filtered off and the product is kept cool, preferably not above ambient temperature. The product is redissolved in a suitable inert solvent, preferably ether, and additional insoluble byproduct is removed. After concentration, the product is again redissolved in a suitable inert solvent, preferably hexane, and additional insoluble byproducts removed. The compound of formula 20 is then isolated. In step 2 of Scheme 5, an acidic solution, preferably ethereal HCl, is treated with the compound of formula 3. Upon dissolution, the solution is cooled, preferably to 10° C., and is treated with an alcohol, preferably benzyl alcohol. After additional stirring, the mixture is held at a given temperature, preferably about 5° C., for a period sufficient to allow complete reaction, typically about 4 days, to provide the compound of formula 21. In step 3 of Scheme 5, a solution of the compound of formula 21 in a suitable inert solvent, preferably acetonitrile, at a temperature ranging from –40° C. to ambient temperature, preferably 0° C., is treated with a solution of the compound of formula 20 in a suitable inert solvent, preferably acetonitrile. The reaction is kept at a temperature ranging from 0° C. to ambient temperature, preferably ambient temperature, to effect reaction. The mixture is then kept at a temperature appropriate to increase solidification of the product, preferably about 5° C., for period sufficient to maximize yield, preferably about 2 days. The compound of formula 22 (Bn is benzyl) is then isolated. In step 4 of Scheme 5, the compound of formula 22 is taken up in a suitable inert solvent, preferably acetonitrile, at a temperature ranging from −40° C. and 40° C., preferably 0° C., and treated with a base, preferably pyridine, and an oxidant, preferably a solution of bromine or iodine in a suitable inert solvent, preferably acetonitrile. The mixture is then stirred at a temperature sufficient to effect reaction, preferably at 0° C. for about 1 hour followed by another hour at ambient temperature. The mixture is then allowed to stand at a temperature sufficient to increase solidification, preferably at 5° C., for a sufficient period, preferably overnight. The compound of formula 23 is then isolated. In step 5 of Scheme 5, the hydration and deprotection of the compound of formula 23 is effected by treatment with an acid, preferably concentrated sulfuric acid. If the compound of formula 23 is sufficiently wet with water from the previous step, no additional water is added. If the compound of formula 23 is dry, then additional water is added, preferably about 10 equivalents. The reaction is carried out at a temperature ranging from −20° C. to 100° C., preferably ambient temperature, for a period sufficient to effect complete reaction, typically marked by complete dissolution and preferably about 3 hours. After the reaction is completed, additional sulfuric acid is added to achieve complete conversion. The mixture is then treated with water or, preferably, ice. The compound of formula 24 is then isolated. In step 6 of Scheme 5, the compound of formula 24 is combined with a trivalent phosphine, preferably triphenyl phosphine, and an $R^3$ containing alcohol, and is treated with an azodicarboxylate derivative, preferably diisopropyl azodicarboxylate, and stirring is continued for a period of at least 1 minute. The compound of formula 25 is then isolated. In step 7 of Scheme 5, a mixture of the compound of formula 25 in a suitable inert solvent, preferably THF, is treated with a desired amine of the formula $R^1R^2NH$ and kept at a temperature sufficient to effect reaction, typically 0° C. to 100° C., preferably 50° C. to 70° C., for a period ranging from 1 hour to 48 hours, preferably overnight. The compound of formula 1 (wherein $X^1$ is O) is then isolated.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula 1 that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formulas 1. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

Included in the present invention are compounds identical to the compounds of formula 1 but for the fact that one or more hydrogen or carbon atoms are replaced by isotopes thereof. Such compounds are useful as research and diagnostic tools in metabolism pharmokinetic studies and in binding assays. Specific applications in research include radioligand binding assays, autoradiography studies and in vivo binding studies. Included among the radiolabelled forms of the compounds of formula 1 are the tritium and $C^{14}$ isotopes thereof.

The in vitro activity of the compounds of formula 1 in inhibiting the KDR/VEGF receptor may be determined by the following procedure.

The ability of the compounds of the present invention to inhibit tyrosine kinase activity may be measured using a recombinant enzyme in an assay that measures the ability of compounds to inhibit the phosphorylation of the exogenous substrate, polyGluTyr (PGT, Sigma™, 4:1). The kinase domain of the human KDR/VEGF receptor (amino acids 805-1350) is expressed in Sf9 insect cells as a glutathione S-transferase (GST)-fusion protein using the baculovirus expression system. The protein is purified from the lysates of these cells using glutathione agarose affinity columns. The enzyme assay is performed in 96-well plates that are coated with the PGT substrate (0.625 μg PGT per well). Test compounds are diluted in dimethylsulfoxide (DMSO), and then added to the PGT plates so that the final concentration of DMSO in the assay is 1.6% (v/v). The recombinant enzyme is diluted in phosphorylation buffer (50 mM Hepes, pH 7.3, 125 mM NaCl, 24 mM $MgCl_2$). The reaction is initiated by the addition of ATP to a final concentration of 10 μM. After a 30 minute incubation at room temperature with shaking, the reaction is aspirated, and the plates are washed with wash buffer (PBS-containing 0.1% Tween-20). The amount of phosphorylated PGT is quantitated by incubation with a HRP-conjugated (HRP is horseradish peroxidase) PY-54 antibody (Transduction Labs), developed with TMB peroxidase (TMB is 3,3',5,5'-tetramethylbenzidine), and the reaction is quantitated on a BioRad™ Microplate reader at 450 nM. Inhibition of the kinase enzymatic activity by the test compound is detected as a reduced absorbance, and the concentration of the compound that is required to inhibit the signal by 50% is reported as the $IC_{50}$ value for the test compound.

To measure the ability of the compounds to inhibit KDR tyrosine kinase activity for the full length protein that exists in a cellular context, the porcine aortic endothelial (PAE) cells transfected with the human KDR (Waltenberger et al., J. Biol. Chem. 269:26988, 1994) may be used. Cells are plated and allowed to attach to 96-well dishes in the same media (Ham's F12) with 10% FBS (fetal bovine serum). The cells are then washed, re-fed with serum depleted media that contains 0.1% (v/v) bovine serum albumin (BSA), and allowed to incubate for 24 hours. Immediately prior to dosing with compound, the cells are re-fed with the serum depleted media (without BSA). Test compounds, dissolved in DMSO, are diluted into the media (final DMSO concentration 0.5% (v/v)). At the end of a 2 hour incubation, $VEGF_{165}$ (50 ng/ml final) is added to the media for an 8 minute incubation. The cells are washed and lysed in HNTG buffer (20 mM Hepes, pH 7.5, 150 mM NaCl, 0.2% Triton™ X-100, 10% glycerol, 0.2 mM PMSF (phenymethylsulfonyl fluoride), 1 μg/ml pepstatin, 1 μg/ml leupeptin, 1 μg/ml aprotonin, 2 mM sodium pyrophosphate, 2 mM sodium orthovanadate). The extent of phosphorylation of KDR is measured using an ELISA assay. The 96-well plates are coated with 1 μg per well of goat anti-rabbit antibody. Unbound antibody is washed off the plate and remaining sites are blocked with Superblock buffer (Pierce) prior to addition of the anti-flk-1 C-20 antibody (0.5 μg per plate, Santa Cruz). Any unbound antibody is washed off the plates prior to addition of the cell lysate. After a 2 hour incubation of the lysates with the flk-1 antibody, the KDR associated phosphotyrosine is quantitated by development with the HRP-conjugated PY-54 antibody and TMB, as described above. The ability of the compounds to inhibit the VEGF-stimulated autophosphorylation reaction by 50%, relative to VEGF-stimulated controls is reported as the $IC_{50}$ value for the test compound.

The ability of the compounds to inhibit mitogenesis in human endothelial cells is measured by their ability to inhibit $^3$H-thymidine incorporation into HUVE cells (human umbilical vein endothelial cells, Clonetics™). This assay has been well described in the literature (Waltenberger J et al. J. Biol. Chem. 269: 26988, 1994; Cao Y et al. J. Biol. Chem. 271: 3154, 1996). Briefly, $10^4$ cells are plated in collagen-coated 24-well plates and allowed to attach. Cells are re-fed in serum-free media, and 24 hours later are treated with various concentrations of compound (prepared in DMSO, final concentration of DMSO in the assay is 0.2% v/v), and 2-30 ng/ml $VEGF_{165}$. During the last 3 hours of the 24 hour compound treatment, the cells are pulsed with $^3$H thymidine (NEN, 1 μCi per well). The media are then removed, and the cells washed extensively with ice-cold Hank's balanced salt solution, and then 2 times with ice cold trichloroacetic acid (10% v/v). The cells are lysed by the addition of 0.2 ml of 0.1 N NaOH, and the lysates transferred into scintillation vials. The wells are then washed with 0.2 ml of 0.1 N HCl, and this wash is then transferred to the vials. The extent of $^3$H thymidine incorporation is measured by scintillation counting. The ability of the compounds to inhibit incorporation by 50%, relative to control (VEGF treatment with DMSO vehicle only) is reported as the $IC_{50}$ value for the test compound.

The activity of the compounds of formula 1, in vivo, can be determined by the amount of inhibition of tumor growth by a test compound relative to a control. The tumor growth inhibitory effects of various compounds are measured according to the methods of Corbett T. H., et al. "Tumor Induction Relationships in Development of Transplantable Cancers of the Colon in Mice for Chemotherapy Assays, with a Note on Carcinogen Structure", *Cancer Res.*, 35, 2434-2439 (1975) and Corbett, T. H., et al., "A Mouse Colon-tumor Model for Experimental Therapy", *Cancer Chemother. Rep. (Part 2)*", 5, 169-186 (1975), with slight modifications. Tumors are induced in the flank by s.c. injection of $1 \times 10^6$ log phase cultured tumor cells suspended in 0.1-0.2 ml PBS. After sufficient time has elapsed for the tumors to become palpable (5-6 mm in diameter), the test animals (athymic mice) are treated with active compound (formulated by dissolution in appropriate diluent, for example water or 5% Gelucire™ 44/14 m PBS by the intraperitoneal (ip) or oral (po) routes of administration once or twice daily for 5-10 consecutive days. In order to determine an anti-tumor effect, the tumor is measured in millimeters with Vernier calipers across two diameters and the tumor volume ($mm^3$) is calculated using the formula: Tumor weight=(length×[width]$^2$)/2, according to the methods of Geran, R. I., et al. "Protocols for Screening Chemical Agents and Natural Products Against Animal Tumors and Other Biological Systems", Third Edition, *Cancer Chemother. Rep.*, 3, 1-104 (1972). The flank site of tumor implantation provides reproducible dose/response effects for a variety of chemotherapeutic agents, and the method of measurement (tumor diameter) is a reliable method for assessing tumor growth rates.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cisplatin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations.

PREPARATION 1

Dimethylcarbamoylisothiocyanate

A three liter, three-neck flask fitted with a mechanical stirrer was charged with dimethylcarbamyl chloride (250 mL, 2.70 mol) in anhydrous acetonitrile (1.5 L) and heated to reflux. Next was added potassium thiocyanate (270 g, 2.8 mol, pre-dried at 160° C. under high vacuum for 3 hours) portionwise over 1 hour with caution as the reaction bubbled violently at the start of each addition. After the final addition, the mixture was heated at reflux for an additional 1 hour. The heating mantle was removed and the mixture stirred at ambient temperature for an additional 2.5 hours and was then stored in the refrigerator overnight. The mixture was filtered to remove unwanted solid material and the filtrate concentrated. To the resulting oil was added ether (1 L) and the solid and thick material discarded. The filtrate was again concentrated affording the desired material a dull orange oil (204 g, 1.57 mol, 58%). $^1$H NMR (400 MHz, CDCl$_3$) δ 2.90 (s, 3H), 2.98 (s, 3H) ppm.

Sodium, 2,2-dicyano-1-(3,3-dimethyl-ureido)-ethenethiolate

To a 1 M solution of sodium ethoxide in ethanol (prepared by treating 110 mL of anhydrous ethanol with 2.5 g (0.11 mole) of sodium) was added malononitrile (7.2 g, 0.11 mole) at 0° C. Dimethylcarbamoylisothiocyanate (14.3 g, 0.110 mole) was added, and the resulting mixture was allowed to warm to ambient temperature overnight. The mixture was concentrated in vacuo. The residue was treated with hexanes and was concentrated in vacuo to a solid. The residue was triturated with hexanes, collected by filtration and dried in vacuo affording 20 g (83%) of sodium; 2,2-dicyano-1-(3,3-dimethyl-ureido)-ethenethiolate as a colorless solid: $^1$H NMR (400 MHz, DMSO-d$_6$) δ 8.40 (s, 1H), 2.78 (s, 6H) ppm; $^{13}$C NMR (100 MHz, DMSO-d$_6$): δ 189.9, 154.3, 121.4, 118.7, 57.9, 36.5 ppm.

3-(4-Cyano-3-mercapto-isothiazol-5-yl)-1,1-dimethyl-urea

A mixture of sodium, 2,2-dicyano-1-(3,3-dimethyl-ureido)-ethenethiolate (5.0 g, 23 mmol), sulfur (0.734 g, 23 mmol) and 46 mL of methanol was stirred at reflux for 24 hours. The mixture was filtered, and the filtrate was concentrated in vacuo. The residue was diluted with water and the resulting mixture was extracted twice with ethyl acetate. The aqueous layer was acidified with 1 M HCl (aq) and was extracted into ethyl acetate. The organic layer was dried over Na$_2$SO$_4$, filtered and concentrated. The solid residue was collected and dried in vacuo yielding 2.0 g (40%) of 3-(4-cyano-3-mercapto-isothiazol-5-yl)-1,1-dimethyl-urea as a yellow solid: $^1$H NMR (400 MHz, DMSO-d$_6$) δ 2.97 (s, 6H) ppm; MS (APCl, m/z): 227 [M–H]$^-$ General Procedure for the Alkylation of 3-(4-Cyano-3-mercapto-isothiazol-5-yl)-1,1-dimethyl-urea To a mixture of 3-(4-cyano-3-mercapto-isothiazol-5-yl)-1,1-dimethyl-urea (0.20 g, 0.88 mmol), the appropriate alkyl chloride, alkyl bromide or alkyl iodide (0.90 mmol) and THF or DMF was added diisopropylethylamine (0.116 g, 0.90 mmol). The resulting mixture was stirred for 24 hours at ambient temperature. The mixture was paritidoned between 1M aqueous HCl and ethyl acetate. The organic layer was removed, and the aqueous layer was extracted three times with ethyl acetate. The combined organic layers were dried over Na$_2$SO$_4$, filtered and concentrated in vacuo. The residue was filtered through a small pad of silica gel eluting with ethyl acetate-hexanes (1:1), affording the alkylated product.

3-(4-Cyano-3-hexylsulfanyl-isothiazol-5-yl)-1,1-dimethyl-urea

Following the above general procedure using iodohexane (0.19 g, 0.90 mmol) as the alkyl iodide afforded 0.14 g (51%) of 3-(4-cyano-3-hexylsulfanyl-isothiazol-5-yl)-1,1-dimethyl-urea as a colorless solid: $^1$H NMR (400 MHz, acetone-d$_6$) δ 9.82 (bs, 1H), 3.20 (t, 2H, J=7.2 Hz), 3.11 (s, 6H), 1.71

(p, 2H, J=7.2 Hz), 1.43 (m, 2H), 1.31 (m, 4H), 0.88 (t, 3H, J=6.0 Hz) ppm; MS (APCl, m/z): 313 [M+H]+.

EXAMPLE 1

5-(3,3-Dimethyl-ureido)-3-hexylsulfanyl-isothiazole-4-carboxylic Acid Amide

A mixture of 3-(4-cyano-3-hexylsulfanyl-isothiazol-5-yl)-1,1-dimethyl-urea (0.09 g, 0.29 mmol) and concentrated sulfuric acid (0.18 mL) was stirred at ambient temperature for 1.5 hours. The mixture was diluted with ice water, extracted three times into ethyl acetate. The combined organic layers were dried over $Na_2SO_4$, filtered and concentrated in vacuo affording 0.076 g (78%) of 5-(3,3-dimethyl-ureido)-3-hexylsulfanyl-isothiazole-4-carboxylic acid amide as a colorless solid: $^1H$ NMR (300 MHz, acetone-$d_6$) δ 7.08 (bs, 2H), 3.20 (t, 2H, J=7.2 Hz), 3.02 (s, 6H), 1.63 (p, 2H, J=7.2 Hz), 1.35 (m, 2H), 1.23 (m, 4H) 0.78 (t, 3H, J=6.9 Hz) ppm; MS (APCl, m/z): 331 [M+H]+.

PREPARATION 2

Sodium; 2,2-dicyano-1-ethoxycarbonylamino-ethenethiolate

Sodium metal (1.01 g, 44 mmol) was dissolved in 40 mL of ethanol at ambient temperature. The resulting solution was cooled in an ice bath, and malononitrile (2.91 g, 44 mmol) was added. The ice bath was removed, and the mixture was stirred at ambient temperture for 30 minutes. After cooling to 0° C., ethoxycarbonylisothiocyanate (5.77 g, 44 mmol) was added, and the mixture was allowed to warm to ambient temperature overnight. The mixture was concentrated in vacuo, and the residue solidified upon repeated dilution with hexane and concentration in vacuo. The resulting yellow solids were collected and dried in vacuo, affording 10.74 g (100%) of sodium, 2,2-dicyano-1-ethoxycarbonylamino-ethenethiolate as a light yellow solid that contain 0.5 molar equiv. of ethanol as indicated by $^1H$ NMR spectroscopy. $^1H$ NMR (300 MHz, DMSO-$d_6$) δ 4.36 (t, 0.5 H, J=5.0 Hz (EtOH)), 4.03 (q, 2H, J=7.1 Hz), 3.43 (dq, 1H J=5.0, 6.7 Hz (EtOH)), 1.26 (t, 3H, J=7.3 Hz), 1.06 (t, 1.5H, J=7.0 Hz (EtOH)) ppm; MS (APCl, m/z): 197 [M−Na]−.

Sodium, 4-cyano-5-ethoxycarbonylamino-isothiazole-3-thiolate

A mixture of sodium, 2,2-dicyano-1-ethoxycarbonylamino-ethenethiolate (3.3 g, 15 mmol), sulfur (0.48 g, 15 mmol) and methanol (30 mL) was heated at reflux for 24 hours. The mixture was filtered and concentrated in vacuo, and the gummy residue was triturated twice with 10:1 ether-ethyl acetate to afford 2.6 g (69%) of sodium, 4-cyano-5-ethoxycarbonylamino-isothiazole-3-thiolate as a yellow solid. $^1H$ NMR (400 MHz, DMSO-$d_6$) δ3.99 (q, 2 H, J=6.8 Hz), 1.16 (t, 3H, J=7.2 Hz) ppm; MS (APCl, m/z): 228 [M−Na]−.

(4-Cyano-3-pentylsulfanyl-isothiazol-5-yl)-carbamic Acid Ethyl Ester

A mixture of sodium, 4-cyano-5-ethoxycarbonylamino-isothiazole-3-thiolate (5.0 g, 20 mmol), 1-iodopentane (4.0 g, 20 mmol) and tetrahydrofuran (20 mL) was stirred at ambient temperature for 16 hours. After concentration in vacuo, the residue was partitioned between ethyl acetate and brine. The aqueous layer was extracted three times with ethyl acetate, and the combined organic layers were dried over $Na_2SO_4$, filtered and concentrated in vacuo. The residue was filtered through a pad of silica gel using 1:1 ethyl acetate-hexane as eluent. The filtrated was concentrated and the residue was recrystallized from cold aqueous methanol, affording 2.5 g (42%) (4-cyano-3-pentylsulfanyl-isothiazol-5-yl)-carbamic acid ethyl ester as a colorless solid. An additional 0.5 g (8.4%) was obtained by concentration of the mother liquor and purification by radial chromatography (4 mm plate, 4:1 hexane-ethyl acetate). $^1H$ NMR (400 MHz, acetone-$d_6$) δ 11.1 (bs, 1 H), 4.32 (q, 2H, J=7.2 Hz), 3.21 (t, 2H, J=7.2 Hz), 1.73 (p, 2H, J=6.8 Hz), 1.44-1.28 (m, 7H), 0.90 (t, 3H, J=7.6 Hz) ppm; MS (APCl, m/z): 312 [M+Na]$^{30}$.

5-Amino-3-pentylsulfanyl-isothiazole-4-carboxylic Acid Amide

A mixture of (4-Cyano-3-pentylsulfanyl-isothiazol-5-yl)-carbamic acid ethyl ester (2.7 g, 9.0 mmol) and concentrated sulfuric acid (5 mL) was heated to 100° C. for 6 hours. After cooling to ambient temperature, the mixture was diluted with ice water, extracted three times with ethyl acetate, and the combined organic layers were dried over $Na_2SO_4$, filtered and concentrated in vacuo, affording 2.2 g (100%) of 5-amino-3-pentylsulfanyl-isothiazole-4-carboxylic acid amide as a yellow oil. $^1H$ NMR (400 MHz, CDCl$_3$) δ 3.26 (t, 2 H, J=7.2 Hz), 1.71 (m, 2H), 1.43-1.19 (m, 4H), 0.88 (t, 3H, J=6.8 Hz) ppm.

(4-Carbamoyl-3-pentylsulfanyl-isothiazol-5-yl)-carbamic Acid Phenyl Ester

To a solution of 5-amino-3-pentylsulfanyl-isothiazole-4-carboxylic acid amide (2.2 g, 9.0 mmol) in 36 mL of tetrahydrofuran was added pyridine (0.90 g, 11 mmol) and phenyl chloroformate (1.7 g, 11 mmol). After stirring for 3 hours, additional pyridine (0.15 g, 1.9 mmol) and phenyl chloroformate (0.29 g, 1.9 mmol) was added, and the mixture was stirred at room temperature overnight. The mixture was concentrated in vacuo, diluted with water and extracted 2× with $CH_2Cl_2$, 1× with ethyl acetate. The combined organic layers were washed with brine, dried over $MgSO_4$, filtered and concentrated in vacuo. The residue was triturated for 12 hours with ether-hexane, and the resulting solids were collected and dried in vacuo, affording 2.6 g (79%) of (4-carbamoyl-3-pentylsulfanyl-isothiazol-5-yl)-carbamic acid phenyl ester as a colorless solid. $^1H$ NMR (300 MHz, CDCl$_3$) δ 7.41 (t, 2 H, J=7.3 Hz), 7.29-7.20 (m, 3H), 3.31 (t, 2H, J=7.3 Hz), 1.72 (m, 2H), 1.50-1.30 (m, 4H), 0.90 (t, 3H, J=7.1 Hz) ppm; MS (APCl, m/z): 366 [M+H]+.

EXAMPLE 2

3-Pentylsulfanyl-5-[3-(3-pyrrolidin-1-yl-propyl)-ureido]-isothiazole-4-carboxylic Acid Amide To a mixture of (4-carbamoyl-3-pentylsulfanyl-isothiazol-5-yl)-carbamic acid phenyl ester (0.10 g, 0.27 mmol) and 1 mL of tetrahydrofuran was added N-3-aminopropylpyrrolidine (0.175 g, 1.4 mmol). After stirring for 72 hours at ambient temperature, the mixture was poured into 1M NaOH, extracted twice with ethyl acetate, and the combined organic layers were dried over $Na_2SO_4$, filtered and concentrated. Purification of the residue by radial chromatography (2 mm plate, 3% ethanol-$CH_2Cl_2$–30% ethanol-$CH_2Cl_2$ containing 0.5% $NH_4OH$), followed by concentration and trituration of the residue with ether-hexane afforded 0.076 g (78%) of 3-pentylsulfanyl-5-[3-(3-pyrrolidin-1-yl-propyl)-ureido]-isothiazole-4-carboxylic acid amide as a colorless solid $^1$H NMR (400 MHz, CDCl$_3$) δ 7.57 (bs, 1H), 7.06 (bs, 2H), 3.35 (m, 2H), 3.26(m, 2H), 2.53 (t, 2H, J=6.8 Hz), 2.47(m, 4H), 1.73 (m, 8H), 1.4-1.2 (m, 4H), 0.88 (t, 3H, J=7.2 Hz) ppm; MS (APCl, m/z): 400 [M+H]$^+$.

PREPARATION 3

3-(4-Cyano-3-hydroxy-isothiazol-5-yl)-1,1-dimethyl-urea (Sodium Salt)

A solution of 3-(2,2-Dicyano-1-mercapto-vinyl)-1,1-dimethyl-urea (sodium salt) (30 g, 137 mmol) in water (300 mL) was treated at ambient temperature with hydrogen peroxide (14 mL of a 10 M solution). The reaction warmed and thickened with solid formation and so was treated with additional water (100 mL). The mixture was heated to reflux for 15 minutes, effecting complete dissolution and then cooled to ambient temperature. After 1 hour at ambient temperature, the mixture was concentrated to a constant weight (35 g, >100% due to water content) and was used immediately in the next step.

5-(3,3-Dimethyl-ureido)-3-hydroxy-isothiazole-4-carboxylic Acid Amide

The solid obtained in the previous step (35 g) was added to concentrated sulfuric acid (150 mL) followed by water (5 mL) and stirred at ambient temperature overnight. The mixture was treated with ice (500 g) and stirred 2 hours. The mixture was filtered and air pulled through the cake overnight. The solid was crushed with mortar and pestle and kept under high vacuum until constant weight (21.7 g, 94.2 mmol, 69% over two steps).

EXAMPLE 3

5-(3,3-Dimethyl-ureido)-3-heptyloxy-isothiazole-4-carboxylic Acid Amide

A suspension of 5-(3,3-Dimethyl-ureido)-3-hydroxy-isothiazole-4-carboxylic acid amide (200 mg, 0.87 mmol) in DMF (5 mL) was treated with KOtBu (107 mg, 0.96 mmol) at ambient temperature causing complete dissolution. Next was added 1-iodoheptane (1 mL) and the reaction stirred at ambient temperature until complete dissappearance of starting materials as measured by TLC using hexane/ethyl acetate/methanol/acetic acid (48/48/2/2) as eluent. The reaction mixture was then concentrated by rotary evaporation under high vacuum, the residue dissolved in ethyl acetate and methanol, and was then purified via radial chromatography (2 mm plate) using the same eluent as for TLC affording two components. The more polar material was identified as the N-alkyated adduct (102 mg, 0.311 mmol, 36%). $^1$H NMR (400 MHz, CDCl$_3$) δ 0.86 (t, J=6.7 Hz, 3H), 1.25-1.31 (m, 8H), 1.64-1.70 (m, 2H), 3.07 (s, 6H), 3.68 (t, J=7.2 Hz, 2H), 5.40 (s, 1H), 8.86 (s, 1H), 12.1 (s, 1H), ppm; $^{13}$C NMR (101 MHz, CDCl$_3$) δ 13.94, 22.45, 26.48, 28.74, 29.52, 31.52, 36.11, 42.54, 166.99 ppm; MS (APCl, m/z): 329 [M+H]$^+$. The less polar material was the O-alkyated adduct (134 mg, 0.408 mmol, 48%). $^1$H NMR (400 MHz, CDCl$_3$) δ 0.88 (t, J=6.8 Hz, 3H), 1.24-1.50 (m, 8H), 1.75-1.88 (m, 2H), 3.07 (s, 6H), 4.43 (t, J=6.7 Hz, 2H), 5.42 (s, 1H), 7.25 (s, 1H appears to be superimposed on CDCl$_3$ peak), 11.6 (s, 1H) ppm; $^{13}$C NMR (101 MHz, CDCl$_3$) δ 13.94, 22.45, 25.86, 28.83, 31.60, 36.11, 68.69, 97.69, 154.15, 162.27, 166.20, 169.45 ppm; MS (APCl, m/z): 329 [M+H]$^+$.

PREPARATION 4

2-Cyano-thioacetimidic Acid 4-methoxy-benzyl Ester

To a solution of sodium hydroxide (13 g, 0.32 mol) in 750 mL of 1:1 ethanol-water at 0° C. was added 4-methoxybenzylmercaptan (50 g, 0.324 mol) and malononitrile (21 g, 0.324 mol). After stirring for 3 hours at 0° C., the mixture was diluted with 500 mL of saturated aqueous NH$_4$Cl, diluted with 4 l of water and filtered. The solids were washed with ether, and the filtrated was diluted with an equal volume of hexane and filtered. The combined solids were dried in vacuo, affording 43 g (60%) of 2-cyano-thioacetimidic acid 4-methoxy-benzyl ester as a colorless solid. $^1$H NMR (400 MHz, CDCl$_3$) δ 7.22 (d, 2H, J=7.6 Hz), 6.84 (d, 2H, J=8.8 Hz), 4.74 (bs, 1H), 3.98 (s, 2H), 3.78 (s, 3H) ppm; MS (APCl, m/z): 221 [M+H]$^+$.

2-Cyano-3-mercapto-3-phenoxycarbonylamino-thioacrylimidic acid 4-methoxy-benzyl Ester To a solution of of 2-cyano-thioacetimidic acid 4-methoxy-benzyl ester (42 g, 0.19 mol) in 191 mL of ethyl acetate at 0° C. was added phenoxycarbonylisothiocyanate (34 g, 0.19 mol), and the mixture was stirred at 0° C. for 24 hours. The mixture was diluted with ether and filtered. The solids were washed with ether, collected and dried in vacuo, affording 56 g (73%) of 2-cyano-3-mercapto-3-phenoxycarbonylamino-thioacrylimidic acid 4-methoxy-benzyl ester as a yellow solid. $^1$H NMR (400 MHz, CDCl$_3$) δ 12.81(s, 1H), 9.01 (s, 1H), 8.68 (s, 1H) 7.28-6.99 (m, 7H), 6.69 (d, 2H, J=8.8 Hz), 4.17 (s, 2H), 3.64 (s, 3H) ppm; MS (APCl, m/z): 400 [M+H]$^+$.

[4-Cyano-3-(4-methoxy-benzylsulfanyl)-isothiazol-5-yl]-carbamic Acid Phenyl Ester To a mixture of 2-Cyano-3-mercapto-3-phenoxycarbonylamino-thioacrylimidic acid 4-methoxy-benzyl ester (11 g, 28 mmol) and ethyl acetate (250 mL) was added, at 0° C., pyridine (4.4 g, 55 mmol). A solution of iodine (7.0 g, 28 mmol) in 350 mL of ethyl acetate was added dropwise over 1 hour. The resulting suspension was stirred for 1 hour, treated with 200 mL of 1 M HCl and filtered, affording 7.0 g (64%) of [4-cyano-3-(4-methoxy-benzylsulfanyl)-isothiazol-5-yl]-carbamic acid phenyl ester as a colorless solid. The filtrate was extracted with 1 l of ethyl acetate, and the organic phase was washed with aqueous NaHCO$_3$, dried over Na$_2$SO$_4$, filtered and concentrated, yielding an additional 2.8 g (26%) of [4-cyano-3-(4-methoxy-benzylsulfanyl)-isothiazol-5-yl]-carbamic acid phenyl ester. $^1$H NMR (400 MHz, CDCl$_3$) δ 11.95 (s, 1H), 7.35 (t, 2H, J=8.4 Hz), 7.20 (m, 3H), 7.13 (d, 2H, J=8.0 Hz), 6.78 (t, 2H, J=8.6 Hz), 4.34 (s, 2H), 3.73 (s, 3H) ppm; MS (APCl, m/z): 398 [M+H]$^+$.

(4-Cyano-3-mercapto-isothiazol-5-yl)-carbamic Acid Phenyl Ester

To a mixture of [4-cyano-3-(4-methoxy-benzylsulfanyl)-isothiazol-5-yl]-carbamic acid was added mercuric acetate (0.80 g, 2.5 mmol). The mixture was allowed to warm to room temperature overnight. After concentration in vacuo, the mixture was diluted with 100 mL of water and 100 mL of ethyl acetate. Hydrogen sulfide was bubbled in slowly until precipitation of the mercury salts was complete. The mixture was diluted with brine, extracted 3× with 200 mL of ethyl acetate, and the combined organic layers were filtered through celite, dried over Na$_2$SO$_4$, filtered and concentrated in vacuo, affording 0.70 g (100%) of (4-cyano-3-mercapto-isothiazol-5-yl)-carbamic acid phenyl ester as a colorless solid. $^1$H NMR (400 MHz, acetone-d$_6$) δ 7.47 (t, 2H, J=7.6 Hz), 7.35-7.30 (m, 3H) ppm; MS (APCI, m/z): 276 [M−H]$^−$.

(4-Carbamoyl-3-mercapto-isothiazol-5-yl)-carbamic Acid Phenyl Ester

A mixture of (4-cyano-3-mercapto-isothiazol-5-yl)-carbamic acid phenyl ester (0.70 g, 2.5 mmol), 2,6-di-tert-butyl-4-methylphenol (BHT) (one crystal) and concentrated sulfuric acid (3 mL) was stirred for 18 hours at room temperature. The mixture was diluted with ice water, extracted 3× with ethyl acetate, and the combined organic layers were dried over Na$_2$SO$_4$, filtered and concentrated in vacuo. The residue was dissolved in 10 mL of ethanol at 0° C. and was treated with 0.096 g (2.5 mmol) of NaBH$_4$. After stirring for 30 minutes, the mixture was acidified with 1 M HCl, extracted into ethyl acetate, dried over Na$_2$SO$_4$, filtered and concentrated in vacuo, affording 0.60 g (81%) of (4-carbamoyl-3-mercapto-isothiazol-5-yl)-carbamic acid phenyl ester as a yellow solid. $^1$H NMR (400 MHz, acetone-d$_6$) δ 13.0 (s, 1H), 11.0-10.9 (bs, 1H), 10.3 (s, 1H), 7.47 (t, 2H, J=6.8 Hz), 7.37-7.30 (m, 4H) ppm; MS (APCI, m/z): 296 [M+H]$^+$.

EXAMPLE 4

5-[3-(3-Chloro-4-fluoro-benzyl)-ureido]-3-(4-methyl-benzylsulfanyl)-isothiazole-4-carboxylic Acid Amide To a mixture of (4-carbamoyl-3-mercapto-isothiazol-5-yl)-carbamic acid phenyl ester (0.075 g, 0.25 mmol) in 0.5 mL of DMF was added 4-methylbenzylchloride (0.036 g, 0.25 mmol), followed by N,N-diisopropylethylamine (0.033 g, 0.25 mmol). After stirring for 18 hours at ambient temperature, tetrahydrofuran (1 mL) was added, followed by 3-chloro-4-fluorobenzylamine (0.081 g, 0.51 mmol). After stirring for 24 hours at 45° C., the mixture was diluted with 1M HCl, extracted 3× with ethyl acetate, and the combined organic layers were dried over Na$_2$SO$_4$, filtered and concentrated in vacuo. The residue was purified by radial chromatography on silica gel eluting with ethyl acetate-hexane, affording 26 mg of 5-[3-(3-chloro-4-fluoro-benzyl)-ureido]-3-(4-methyl-benzylsulfanyl)-isothiazole-4-carboxylic acid amide as a colorless solid. HPLC ret. time: 4.9 minutes. $^1$H NMR (400 MHz, acetone-d$_6$) δ7.95 (bs, 1H), 7.54 (dd, 1H, J=2, 7.2 Hz), 7.39 (m, 1H), 7.31-7.25 (m, 3H), 7.11 (d, 2H, J=8.0 Hz), 7.01 (bs, 2H), 4.48 (m, 4H), 2.28 (s, 3H) ppm; MS (APCI, m/z): 465 [M+H]$^+$.

PREPARATION 5

2-Cyano-acetimidic Acid Benzyl Ester

To a solution of ethereal HCl (4.00 L, 1M, 4.00 mol) was added warmed (liquified) malononitrile (252 mL, 4.00 mol). Upon dissolution, the solution was cooled to 10° C. Next was added benzyl alcohol (414 mL, 4.00 mol) and the mixture stirred at 10° C. for 0.5 hour. The reaction flask was placed in the refrigerator and allowed to stand at 5° C. for 4 days. The solid obtained was filtered cold, washed with cold ether (1.5 L) and dried under vacuum (40 mm Hg) for 1 hour affording 545 g (2.59 mol, 65%) of the Pinner adduct as a white solid. The neutralization of this HCl salt was carried out as follows. A solution of potassium carbonate (359 g, 2.59 mol) in water (700 mL) was prepared and cooled to 5° C. The solution was added to a separatory funnel along with ether (2 L) and THF (500 mL). The entire separatory funnel was placed in an ice bath until the temperature of the extractant solution was 5° C. The Pinner adduct (545 g, 2.59 mol) was then added to the separatory funnel and the funnel was shaken vigorously for 5 minutes. The aqueous layer was discarded and the organic layer collected following filtration of suspended particles. The organic layer was placed again into the separatory funnel, shaken with brine and allowed to settle completely to allow virtual complete removal of brine layer. The organic layer was concentrated on a rotary evaporator and the unstable product (327 g, 1.88 mmol, 73%) used immediately in the next step.

Phenoxycarbonylisothiocyanate

A suspension of KSCN (80 g, 823 mmol, from a fresh, previously unopened bottle) in ethyl acetate (2 L, dry) was stirred vigorously overnight under an atmosphere of nitrogen in order to powder the KSCN. The fine suspension was then treated dropwise with phenyl chloroformate (100 mL, 800 mmol) over 1 hour. The reaction was stirred overnight at ambient temperature and then stirred at 5° C. for 8 hours. The KCl produced was filtered off and the solvent removed by rotary evaporation taking care not to warm the product above ambient temperature. The product was redissolved in ether (2 L), the additional precipitate removed by filtration and discarded, and the ethereal solution of product again concentrated under reduced pressure taking care not to warm the product above ambient temperature. The product was redissolved in hexane (2 L), the additional precipitate removed by filtration and discarded, and the hexane solution of product again concentrated under reduced pressure taking care not to warm the product above ambient temperature. The product so obtained (101 g, 564 mmol, 68%) was highly pure and could be stored at −5° C. for a matter of several days, or at room temperature for a few hours, but was typically used quickly, as in the current example. $^1$H NMR (400 MHz, CDCl$_3$) δ 7.10-7.21 (m, 2H), 7.21-7.31 (m, 1H), 7.31-7.45 (m, 2H) ppm; $^{13}$C NMR (101 MHz, CDCl$_3$) δ 120.75, 126.77, 129.65, 150.46 ppm; IR (neat) 1190, 1232, 1491, 1590, 1751, 1960 cm−1.

2-Cyano-3-mercapto-3-phenoxycarbonylamino-acrylimidic Acid Benzyl Ester

To a stirred 0° C. solution of 2-cyano-acetimidic acid benzyl ester (327 g, 1.88 mol) in acetonitrile (1 L) was added a 0° C. solution of phenoxycarbonylisothiocyanate (353 g, 1.97 mol) in acetonitrile (1 L). The reaction was allowed to warm to ambient temperature and was stirred overnight. The mixture was then placed in the refrigerator and kept still at 5° C. for 48 hours. The solid product was filtered, compressed, and washed with 20° C. acetonitrile (3×200 mL). Air was then drawn though the relatively stable solid followed by further drying under high vacuum to yield a yellow solid (282 g, 798 mmol, 42%). $^1$H NMR (400 MHz, DMSO) δ 5.39 (s, 2H), 7.11-7.19 (m, 2H), 7.20-7.24 (m, 1H), 7.36-7.46 (m, 7H), 10.23 (broad s, 1H), 10.67 (s, 1H), 12.19 (broad s, 1H) ppm; MS (APCI, m/z): 354 [M+H]$^+$.

(3-Benzyloxy-4-cyano-isiothiazol-5-yl)-carbamic Acid Phenyl Ester

To a 0° C. suspension of the adduct, 2-cyano-3-mercapto-3-phenoxycarbonylaminoacrylimidic acid benzyl ester (282 g, 798 mmol) in acetonitrile (2 L) was added pyridine (129 mL, 1.60 mol). Next was added a solution of bromine (41.1 mL, 798 mmol) in acetonitrile (200 mL) over 15 minutes. The reaction was stirred at 0° C. for an additional 1 hour and then at ambient temperature for 2 hour. The mixture was placed in the refrigerator and held at 5° C. overnight. The solid product was filtered and washed with 0° C. ether (1 L), dried in the same funnel by drawing air through the solid for 4 hours. The solid was added to water (1 L), stirred vigorously for 1 hour, filtered and dried in the same funnel by drawing air through the solid overnight to afford a white solid (320 g pure though still containing some water) that was used, as is, in the next step. $^1$H NMR (400 MHz, DMSO) δ5.35 (s, 2H), 7.25-7.45 (m, 10H), 13.20 (broad s, 1H) ppm; MS (APCl, m/z): 350 [M−H]$^−$.

(4-Carbamoyl-3-hydroxy-isothiazol-5-yl)-carbamic Acid Phenyl Ester

The wet solid, (3-Benzyloxy-4-cyano-isothiazol-5-yl)-carbamic acid phenyl ester, (320 g) was added slowly to concentrated sulfuric acid (650 mL) over 1.5 hours. Additional concentrated sulfuric acid (100 mL) was added and the mixture stirred a further 3 hours. The viscous solution was diluted by slow addition of ice (2000 g) followed by vigorous stirring for an additional 2 hours. The acid was partially removed by dividing the suspension into eight containers that were placed in a centrifuge, spun at 3000 rpm for 45 minutes at 21° C. The aqueous layer was discarded, additional pure water was added, the pellet resuspended, and the process repeated. After seven dilution/centrifugation/redilution cycles, the pH of the aqueous layer had increased to ~4 and the solid was collected and dried by drawing air through a cake in a funnel for 2 days. The less-wet solid was crushed, placed again in the filter, and air was again drawn through the solid for another day. This process was repeated until the solid was dry to afford a tan solid (234 g, 105% over two steps, minor impurities present—did not interfere appreciably with the subsequent steps). $^1$H NMR (400 MHz, DMSO) δ 7.00 (broad s, 1H), 7.27-7.31 (m, 3H), 7.40-7.45 (m, 2H), 7.89 (s, 1H), 8.08 (s, 1H), 11.92 (s, 1H); MS (APCl, m/z): 184 [M−(H and PhOH)]$^−$.

[4-Carbamoyl-3-(2,6-difluoro-4-methyl-benzyloxy)-isothiazol-5-yl]-carbamic Acid Phenyl Ester To a suspension of (4-carbamoyl-3-hydroxy-isothiazol-5-yl)carbamic acid phenyl ester (1.77 g, 6.23 mmol), triphenylphosphine (1.99 g, 7.59 mmol), o,o'-difluoro-p-methyl-benzyl alcohol (1.00 g, 6.32 mmol) in THF (21 mL) was added diisopropyl azodicarboxylate (DIAD, 1.49 mL, 7.59 mmol) slightly faster than dropwise. The reaction mixture warmed and became clear. After stirring for 15 minutes, the majority of THF was removed by rotary evaporation and the crude mixture purified on silica gel using chloroform/acetone/acetic acid (98.5/0.75/0.75) as eluent to afford a white solid (802 mg, 1.91 mmol, 30%).

EXAMPLE 5

3-(2,6-Difluoro-4-methyl-benzyloxy)-5-{3-[3-(4-methyl-piperazin-1-yl)-propyl]-ureido}-isothiazole-4-carboxylic Acid Amide To a suspension of [4-Carbamoyl-3-(2,6-difluoro-4-methyl-benzyloxy)-isothiazol-5-yl]-carbamic acid phenyl ester (125 mg, 0.298 mmol) in THF (1 mL) was added 1-(3-aminopropyl)-4-methylpiperazine (70 mg, 0.45 mmol). The mixture was shaken at 50° C. overnight, cooled to ambient temperature, and loaded directly onto a radial chromatograph followed by elution with chloroform/methanol/concentrated ammonium hydroxide (50/5/1) to afford a white solid (121 mg, 0.251 mmol, 84%). $^1$H NMR (400 MHz, CDCl$_3$) δ 1.72 (t, J=5.81 Hz, 2H), 2.20-2.85 (m, 10H), 2.28 (s, 3H superimposed on multiplet from 2.20-2.85), 2.35 (s, 3H superimposed on multiplet from 2.20-2.85), 3.39 (t, J=5.4 Hz, 2H), 5.51 (s, 2H), 5.74 (broad s, 1H), 6.74 (d, J=8.3 Hz, 2H), 7.05 (s, 1H), 7.58 (broad s, 1H), 11.01 (broad s, 1H) ppm; MS (APCl, m/z): 483 [M+H]$^+$.

Synthesis of Representative Fluorotoluene Derivatives

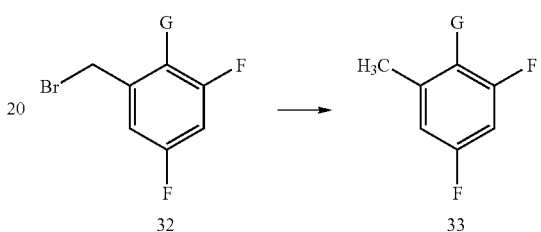

1,3-Difluoro-5-methyl-benzene (G=H)

A mixture of 1-bromomethyl-3,5-difluoro-benzene (75 g, 0.362 mol), Pd/C (5%, 5 g), and sodium acetate (208 g, 2.54 mol) in ether (300 mL) was treated with hydrogen gas (50 psi) in a Parr shaker for 2 days. The mixture was filtered through Celite and the organic solution washed three times with saturated aqueous sodium bicarbonate solution. The aqueous layers were washed with ether and the combined organic layers dried (MgSO$_4$), filtered, and partially concentrated by evaporation using a cold water bath. The volatile product was obtained as a mixture with ether and the ratio (~3:2, ether:product, g:g) calculated based on $^1$H NMR integration to determine actual yield (45.5 g, 0.355 mol, 98%) of product for scaling reagents in the ensuing reaction. $^1$H NMR (400 MHz, CDCl$_3$) δ 2.25 (s, 3H), 6.51-6.56 (m, 1H), 6.58-6.60 (m, 2H) ppm.

1,2,5-Trifluoro-3-methyl-benzene (G=F)

The title compound was prepared from 1-bromomethyl-2,3,5-trifluoro-benzene by a procedure analogous to that for 3,5-difluorotoluene, above. $^1$H NMR (400 MHz, CDCl$_3$) δppm; MS (APCl, m/z): [M+H]$^+$.

Synthesis of Representative Benzyl Alcohols for Conversion to R$^3$

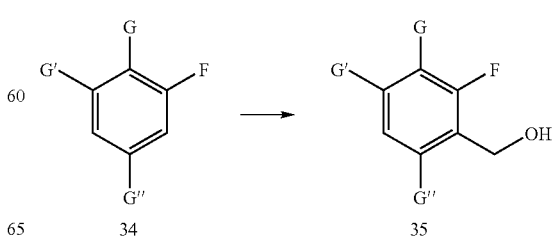

(2,6-Difluoro-4-methyl-phenyl)-methanol (G=H, G'=Me, G"=F)

A solution of 1,3-difluoro-5-methyl-benzene (45.5 g, 0.355 mol, mixed with a small volume of ether) in dry THF (1.77 L) was cooled to −78° C. under nitrogen and treated dropwise with n-BuLi (142 mL of a 2.5 M solution in hexanes, 0.355 mol). The solution was stirred an additional 25 minutes and was then treated with DMF (27.5 mL, 0.355 mol). After stirring an additional 45 minutes, the solution was treated with acetic acid (40.6 mL, 0.71 mol) and the flask removed from the −78° C. bath. The mixture was stirred at ambient temperature for 2 hours and was then treated successively with water (300 mL) and MeOH (300 mL). Next was added, portionwise, NaBH$_4$ (26.8 g, 0.71 mol) followed by stirring for 1 hour. The flask was cooled in an ice bath and the mixture treated with 6 N HCl until pH ~5. The mixture was concentrated via rotary evaporation to remove THF and MeOH and the product extracted with ether and washed several times with small volumes of water and once with brine. The ether layer was dried (MgSO$_4$), filtered, and concentrated to afford an oil (45 g, 0.285 mol, 80%) that solidified upon refrigeration. $^1$H NMR (400 MHz, CDCl$_3$) δ 1.75 (t, J=6.5 Hz, 1H), 2.32 (s, 3H), 4.72 (d, J=6.4 Hz, 2H), 6.69 (d, J=7.9 Hz, 2H) ppm.

(2,3,6-Trifluoro-4-methyl-phenyl)-methanol (G=F, G'=Me, G"=F)

The title compound was prepared from 1,2,5-trifluoro-3-methyl-benzene by a procedure analogous to that for (2,6-difluoro-4-methyl-phenyl)-methanol, above. $^1$H NMR (400 MHz, CDCl$_3$) δ 1.87 (broad s, 1H), 2.28 (d, J=1.9 Hz, 3H), 4.74 (s, 2H), 6.68-6.72 (m, 1H) ppm.

(4-Bromo-2,6-difluoro-phenyl)-methanol (G=H, G'=Br, G"=F)

The title compound was prepared from 1-bromo-3,5-difluoro-benzene by a procedure analogous to that for (2,6-difluoro-4-methyl-phenyl)-methanol, above with the following exception: lithium diisopropylamide (LDA) was used in place of n-BuLi and deprotonation time was extended to 45 minutes. $^1$H NMR (400 MHz, CDCl$_3$) δ 1.91 (t, J=6.5 Hz, 1H), 4.71 (d, J=6.4 Hz, 2H), 7.06-7.12 (m, 2H) ppm.

(4-Bromo-2,3,6-trifluoro-phenyl)-methanol (G=F, G'=Br, G"=F)

The title compound was prepared from 1-bromo-2,3,5-trifluoro-benzene by a procedure analogous to that for (2,6-difluoro-4-methyl-phenyl)-methanol, above with the following exception: lithium diisopropylamide (LDA) was used in place of n-BuLi and deprotonation time was extended to 45 minutes. $^1$H NMR (400 MHz, CDCl$_3$) δ 1.89 (t, J=6.5 Hz, 1H), 4.75 (d, J=6.4 Hz, 2H), 7.11-7.15 (m, 1H) ppm.

(3-Chloro-2,6-difluoro-phenyl)-methanol (G=Cl, G'=H, G"=F)

The title compound was prepared from 1-chloro-2,4-difluoro-benzene by a procedure analogous to that for (2,6-difluoro-4-methyl-phenyl)-methanol, above. $^1$H NMR (400 MHz, CDCl$_3$) δ 1.90 (t, J=6.4 Hz, 1H), 4.78 (d, J=6.4 Hz, 2H), 6.87 (app. dt, J=1.8, 8.9 Hz, 1H), 7.32 (app. dt, J=5.8, 2.8 Hz, 1H) ppm.

(2-Fluoro-4,6-dimethyl-phenyl)-methanol (G=H, G'=Me, G"=Me)

A solution of N,N,N',N'-tetramethylethylenediamine (13.4 mL, 88.6 mmol) in THF (115 mL) was cooled to −78° C. and treated with sec-BuLi (68.2 mL of of 1.3 M solution in cyclohexane, 88.6 mmol). The resulting yellow solution was stirred for 20 minutes at −78° C. and was then treated with a solution of 1-fluoro-3,5-dimethyl-benzene (10.0 g, 80.5 mmol) in THF (56 mL). The mixture was stirred for 1 hour at −78° C. and was then treated with a solution of DMF (6.86 mL, 88.6 mmol) in THF (26 mL). The reddish-brown mixture was stirred an additional 1 hour, and was then treated with HOAc (10 mL) and water (200 mL). The mixture was warmed to ambient temperature, extracted with ether (500 mL) and the aqueous layer extracted with additional ether (2×300 mL). The combined organic extracts were combined and washed successively with 0.2 M HCl (2×200 mL), water (500 mL) and brine (300 mL). The organic layer was dried (MgSO$_4$) and concentrated to afford the aldehyde as a clear oil (11.9 g, 78.2 mmol, 97%). The aldehyde was then dissolved in THF (100 mL), MeOH (100 mL), and water (100 mL) and treated portionwise with NaBH$_4$ (2.96 g, 78.2 mmol). The mixture was stirred at ambient temperature for 1 hour and was then concentrated under reduced pressure to remove the THF and MeOH. The remaining aqueous layer was extracted twice with ether (600 mL and 200 mL) and the combined organic layers washed successively with 0.1 M HCl (300 mL), water (300 mL), and brine (300 mL). The organic layer was dried (MgSO$_4$) and concentrated to afford an oil (10.8 g, 70.4 mmol, 90%). $^1$H NMR (400 MHz, CDCl$_3$) δ 2.28 (s, 3H), 2.38 (s, 3H), 4.70 (s, 2H), 6.71 (d, J=10.6 Hz, 1H), 6.79 (s, 1H) ppm.

(2-Fluoro-4-methyl-phenyl)-methanol (G=H, G'=Me, G"=H)

A solution of 4-bromo-3-fluorotoluene (12.2 g, 64.7 mmol) in THF (170 mL) was cooled to −78° C. and treated dropwise with n-BuLi (25.9 mL of a 2.5 M solution in hexanes, 65 mmol). After stirring for 1 hour, the solution was treated with N,N-dimethylformamide (DMF) (5.5 mL, 71 mmol) and stirred an additional 30 minutes followed by addition of acetic acid (12 mL). The flask was removed from the cold-bath and allowed to warm to ambient temperature. Next was added water and the product extracted with ether. The organic layer was washed successively with dilute HCl and brine and was then dried (MgSO$_4$) and concentrated. The procedure was repeated (using 11.8 g 4-bromo-3-fluorotoluene) and the combined material subjected to the following reduction: The aldehyde (17.6 g, 127 mmol) was dissolved in THF (165 mL), MeOH (165 mL), and water (165 mL). Next was added NaBH$_4$ (5.3 g, 140 mmol) portionwise over several minutes (bubbling, exothermic) and stirring was continued for 2 hours. The reaction was diluted with a large volume of ether and was treated with dilute HCl to quench. The layers were separated and the organic layer was dried (MgSO$_4$) and concentrated to afford the product as an oil (17.0 g, 121 mmol, 95%). $^1$H NMR (400 MHz, CDCl$_3$) δ 2.33 (s, 3H), 4.69 (s, 2H), 6.86 (d, J=11.2 Hz, 1H), 6.93 (d, J=7.24-7.28 (m, 1H) ppm.

(4-Chloro-2,5-difluoro-phenyl)-methanol

To a mixture of 4-chloro-2,5-difluoro-benzoic acid (15 g, 78 mmol) tetrahydrofuran (THF) (75 mL) and trimethylborate (26 mL, 230 mmol) was added borane-methylsulfide complex (86 mL, 86 mmol, 10 M solution in DMS), and the mixture was stirred for 18 hours at ambient temperature. Additional borane-methylsulfide complex (2.47 mL, 24.7 mmol) was added to drive the reaction to completion. The mixture was poured into 1M aqueous NaOH, extracted 3× with ether, and the combined organic layers were dried over anhydrous MgSO$_4$, filtered and concentrated in vacuo. Trituration of the solid residue with ether-hexane afforded 14 g of (4-chloro-2,5-difluoro-phenyl)-methanol as a colorless solid. $^1$H NMR (400 MHz, CDCl$_3$) 67 7.26 (dd, 1H, J=6, 8.8 Hz), 7.11 (dd, 1H, J=6, 9.2 Hz), 4.71 (d, 2H, J=6.0 Hz), 1.80 (t, 1H, J=6.0 Hz) ppm.

tert-Butyl-(2,3-difluoro-benzyloxy)-dimethyl-silane

To a solution of (2,3-difluoro-phenyl)-methanol (5.0 g, 35 mmol), imidazole (4.9 g, 72 mmol) and DMF (40 mL) was added tert-butyldimethylchlorosilane (5.4 g, 36 mmol). After stirring at ambient temperature for 24 hours, the mixture was partitioned between 400 mL of ether and 100 mL of water. The organic layer was washed twice with water, dried over MgSO$_4$, filtered and concentrated in vacuo, affording 6.8 g of tert-butyl-(2,3-difluoro-benzyloxy)-dimethyl-silane as a colorless oil. $^1$H NMR (400 MHz, CDCl$_3$) δ 7.22 (m, 1H), 7.04 (m, 2H), 4.79 (s, 2H), 0.91 (s, 9H), 0.12 (s, 6H) ppm.

tert-Butyl-(2,3-difluoro-4-methyl-benzyloxy)-dimethyl-silane

To a solution of TMEDA (3.9 mL, 3.0 g, 26 mmol) in THF (33 mL) at −78° C. was added sec butyllithium (20 mL, 1.3 M in hexane, 26 mmol). After stirring for 20 minutes, a solution of tert-butyl-(2,3-difluoro-benzyloxy)-dimethyl-silane (6.0 g, 23 mmol) in 17 mL of THF was added dropwise. After stirring for 1 hour, the solution was added dropwise to a solution of methyl iodide (8 mL) in THF (40 mL) at −20° C. After stirring for 18 hours, the mixture was quenched with saturated aqueous NH$_4$Cl, extracted 3× into ether, and the combined organic layers were dried over MgSO$_4$, filtered and concentrated in vacuo, giving 6.6 g of tert-butyl-(2,3-difluoro-4-methyl-benzyloxy)-dimethyl-silane as a light yellow oil. $^1$H NMR (400 MHz, CDCl$_3$) δ 7.07 (app. t, 1H, J=7.2 Hz), 6.89 (app. t, 1H, J=7.3 Hz), 4.74 (s, 2H), 2.26 (d, 3H, J=1.9 Hz), 0.87 (s, 9H), 0.07 (s, 6H) ppm.

(2,3-Difluoro-4-methyl-phenyl)-methanol

To a solution of tert-butyl-(2,3-difluoro-4-methyl-benzyloxy)-dimethyl-silane (6.5 g, 24 mmol) in THF (24 mL) was added tetrabutylammonium fluoride (24 mL of a 1M solution in THF, 24 mmol). After stirring at ambient temperature for 1 hour, the mixture was poured into water, acidified with 1M aqueous HCl, extracted 3× with ethyl acetate, and the combined organic layers were dried over Na$_2$SO$_4$, filtered and concentrated in vacuo. The residue was purified by silica gel chromatography (10:1 to 2:1 hexane-ethyl acetate), affording (2,3-Difluoro-4-methyl-phenyl)-methanol as a light yellow oil.

1-Bromo-2,5-difluoro-4-methyl-benzene

A mixture of 2,5-difluorotoluene (25 g, 0.20 mol) and iron powder (11 g, 0.2 mol) was cooled to −5° C. Bromine was added dropwise such that the internal temperature of the reaction did not rise above 0° C. After stirring for 3 hours, the mixture was diluted with ether, filtered and washed with aqueous sodium thiosulfate solution. The aqueous layer was extracted with ether, and the combined organic layers were dried over MgSO$_4$, filtered and concentrated in vacuo. Distillation at atmospheric pressure gave 34 g of 1-bromo-2,5-difluoro-4-methyl-benzene as a colorless oil (b.p. 180 oC). $^1$H NMR (300 MHz, CDCl$_3$) δ 7.20 (dd, 1H, J=6.0, 8.5 Hz), 6.93 (m, 1H), 2.23 (s, 3H) ppm.

(2,5-Difluoro-4-methyl-phenyl)-methanol

A mixture of 1-bromo-2,5-difluoro-4-methyl-benzene (3.3 g, 16 mmol) and ether (75 mL) was cooled to −78° C., and a solution of n-butyllithium in hexane (5.4 mL, 2.5 M, 13.5 mmol) was added dropwise. After stirring for 1 hour, dimethylformamide (1.1 mL, 14 mmol) was added, and the mixture was stirred for 1 hour. The mixture was treated with 1M HCl and water, warmed to ambient temperature and was extracted 3× with ether. The combined organic layers were dried over MgSO$_4$, filtered and concentrated in vacuo. The residue was diluted with tetrahydrofuran (50 mL), and the mixture was treated with sodium borohydride (0.50 g, 13.5 mmol) and ethanol (2 mL). After stirring for 30 minutes, the mixture was diluted cautiously with 0.5M aqueous HCl, extracted 3× with ethyl acetate, and the combined organic layers were dried over Na$_2$SO$_4$, filtered and concentrated in vacuo. Recrystallization of the residue from hexane afforded 1.24 g (54%) of (2,5-Difluoro-4-methyl-phenyl)-methanol as a colorless solid. $^1$H NMR (400 MHz, CDCl$_3$) δ 7.05 (dd, 1H, J=6.0, 9.2 Hz), 6.84 (dd, 1H, J=6.4, 10 Hz), 4.68 (d, 2H, J=6.0 Hz), 2.23 (s, 3H), 1.76 (t, 1H, J=6.0 Hz) ppm.

(5-Chloro-2-fluoro-4-methyl-phenyl)-methanol (5-Chloro-2-fluoro-4-methyl-phenyl)-methanol was prepared in analogous fashion to (2,5-difluoro-4-methyl-phenyl)-methanol using 2-chloro-5-fluorotoluene as starting material. $^1$H NMR (400 MHz, CDCl$_3$) δ 7.38 (d, 1H, J=6.8 Hz), 6.92 (d, 1H, J=10 Hz), 4.69 (s, 2H), 2.34 (s, 3H) ppm.

4-Chloro-2,6-difluoro-benzaldehyde

To a solution of 3,5-difluoro-1-chlorobenzene (5.0 g, 34 mmol) in tetrahydrofuran (70 mL) at −78° C. was added a solution of n-butyllithium in hexane (12.1 mL, 2.5 M, 30 mmol). After stirring for 1 hour, dimethylformamide (5.2 mL, 67 mmol) was added, and the mixture was stirred for 1.5 hours. The mixture was warmed to ambient temperature, diluted with ether and poured into 150 mL of 0.5 M aqueous HCl. The aqueous phase was extracted 3× into ether, and the combined organic layers were dried over MgSO$_4$, filtered and concentrated in vacuo, affording 5.72 g (96%) of 4-chloro-2,6-difluoro-benzaldehyde as a colorless solid. $^1$H NMR (400 MHz, CDCl$_3$) δ 10.27 (s, 1H), 7.04 (d, 2H, J=7.9 Hz) ppm.

(4-Chloro-2,6-difluoro-phenyl)-methanol

To a mixture of 4-chloro-2,6-difluoro-benzaldehyde (5.7 g, 32 mmol), tetrahydrofuran (150 mL) and ethanol (20 mL) was added sodium borohydride (1.2 g, 32 mmol) at 0° C. The mixture was stirred for 30 minutes, warmed to ambient temperature, and additional sodium borohydride (0.40 g, 11 mmol) was added to drive the reaction to completion (TLC). The mixture was concentrated in vacuo, diluted with ether and treated cautiously with 1M aqueous HCl. The aqueous phase was extracted 3× with ether, and the combined organic layers were dried over MgSO$_4$, filtered and concentrated. Trituration of the residue with pentane afforded 4.8 g (83%)

of (4-chloro-2,6-difluoro-phenyl)-methanol as a colorless solid. ¹H NMR (300 MHz, CDCl₃) δ 7.04 (d, 2H, J=7.1 Hz), 4.73 (s, 2H) ppm.

General Procedure for the Preparation of Isothiazole Phenyl Carbamates: [4-Carbamoyl-3-(2,5-difluoro-4-methyl-benzyloxy)-isothiazol-5-yl]-carbamic Acid Phenyl Ester To a mixture of (4-carbamoyl-3-hydroxy-isothiazol-5-yl)-carbamic acid phenyl ester (2.1 g, 7.6 mmol), (2,5-difluoro-4-methyl-phenyl)-methanol (1.2 g, 7.6 mmol), triphenylphosphine (2.1 g, 8.0 mmol) and tetrahydrofuran (19 mL) was added diethylazodicarboxylate (1.3 mL, 8.0 mmol). After stirring for 16 hours at ambient temperature, additional (2,5-difluoro-4-methyl-phenyl)-methanol (0.24 g, 1.5 mmol), triphenylphosphine (0.42 g, 1.6 mmol) and diethylazodicarboxylate (0.30 mL, 1.8 mmol) were added, and the mixture was stirred for 1 hour. After concentrating in vacuo, the mixture was purified by silica gel chromatography eluting with acetone-acetic acid-methylene chloride (0.5%,0.5%,99%), affording, after trituration from ether-hexane, 1.1 g (35%) of [4-carbamoyl-3-(2,5-difluoro-4-methyl-benzyloxy)-isothiazol-5-yl]-carbamic acid phenyl ester as a colorless solid. HPLC ret. time: 4.8 min. ¹H NMR (400 MHz, CD₃OD) δ 7.40 (t, 2H, J=8.0 Hz), 7.27 (t, 1H, J=7.2 Hz), 7.20 (d, 2H, J=8.4 Hz), 7.17 (dd, 1H, J=6.0,9.2 Hz), 7.00 (dd, 1H, J=6.4, 10 Hz), 5.49 (s, 2H), 2.24 (s, 3H) ppm.

[4-Carbamoyl-3-(2,3-difluoro-4-methyl-benzyloxy)-isothiazol-5-yl]-carbamic Acid Phenyl Ester Preparation of the title compound as described for example 3 using (2,3-difluoro-4-methyl-phenyl)-methanol afforded 1.7 g (57%) of [4-carbamoyl-3-(2,3-difluoro-4-methyl-benzyloxy)-isothiazol-5-yl]-carbamic acid phenyl ester as a colorless solid. HPLC ret. time: 4.8 minutes. ¹H NMR (400 MHz, CDCl₃) δ 11.38 (s, 1H), 7.40 (t, 2H, J=8.0 Hz), 7.26 (t, 1H, J=7.2 Hz), 7.20 (d, 1H, J=8.4 Hz), 7.14 (b, 1H), 7.11 (t, 1H, J=7.6 Hz), 6.94 (t, 1H, J=7.2 Hz), 5.6 (b, 1H), 5.52 (s, 2H), 2.31 (d,3H, J=1.7 Hz) ppm.

[4-Carbamoyl-3-(2,5-difluoro-4-chloro-benzyloxy)-isothiazol-5-yl]-carbamic Acid Phenyl Ester Preparation of the title compound as described for example 3 using (2,5-difluoro-4-chloro-phenyl)-methanol afforded 0.86 g (26%) of [4-carbamoyl-3-(2,5-difluoro-4-chloro-benzyloxy)-isothiazol-5-yl]-carbamic acid phenyl ester as a colorless solid. HPLC ret. time: 4.8 minutes. ¹H NMR (400 MHz, DMSO-d₆) δ 11.73 (s, 1H), 8.04 (s, 1H), 7.77 (m, 2H), 7.51 (m, 2H), 7.36 (m, 3H), 7.23 (s, 1H), 5.51 (s, 2H) ppm.

[4-Carbamoyl-3-(2,6-difluoro-4-chloro-benzyloxy)-isothiazol-5-yl]-carbamic Acid Phenyl Ester Preparation of the title compound as described for example 3 using (2,6-difluoro-4-chloro-phenyl)-methanol afforded 0.86 g (26%) of [4-carbamoyl-3-(2,6-difluoro-4-chloro-benzyloxy)-isothiazol-5-yl]-carbamic acid phenyl ester as a colorless solid. HPLC ret. time: 4.5 minutes. ¹H NMR (400 MHz, CDCl₃, CD₃OD) δ 7.31 (t, 2H, J=8.0 Hz), 7.18 (t, 1H, J=7.6 Hz), 7.10 (d, 2H, J=7.6 Hz), 6.92 (d, 2H, J=7.2 Hz), 5.45 (s, 2H) ppm.

General Procedure for the Preparation of Isothiazole Ureas

EXAMPLE 6

3-(2,5-difluoro-4-methyl-benzyloxy)-5-[3-(4-pyrrolidin-1-yl butyl)-ureido]-isothiazole-4-carboxylic Acid Amide A mixture of [4-carbamoyl-3-(2,5-difluoro-4-methyl-benzyloxy)-isothiazol-5-yl]-carbamic acid phenyl ester (0.34 g, 0.81 mmol), 4-pyrrolidinobutylamine (0.12 g, 0.81 mmol) and tetrahydrofuran (2.8 mL) was shaken at 45-50° C. for 24 hours. The mixture was concentrated and purified by radial chromatography (4 mm plate, CH₃OH—CHCl₃—NH₄OH (10:89:1) to (15:84:1)), affording 0.31 g of the title compound as a colorless solid. The material was dissolved in ca. 10 mL of 4:1 methanol-chloroform at −10° C. and was treated with a solution of methanesulfonic acid (0.043 mL in 0.5 mL of CH₃OH). After stirring for 5 minutes, the mixture was concentrated in vacuo, and the residue was triturated with methanol-ether, affording 0.35 g of the title compound (82%) as a colorless solid. HPLC ret. time: 3.3 minutes. ¹H NMR (400 MHz, D₂O) δ 6.74 (dd, 1H, J=6.0, 9.6 Hz), 6.63 (dd, 1H, J=6.4, 10.4 Hz), 4.61 (s, 2H), 3.44 (m, 2H), 3.05-2.98 (m, 4H), 2.98-2.81 (m, 2H), 2.62 (s, 3H), 1.95-1.93 (m, 4H), 1.83-1.80 (m, 2H), 1.6-1.5 (m, 2H), 1.4-1.3 (m, 2H) ppm; MS (APCl, m/z): 468 [M+H]⁺.

EXAMPLE 7

3-(2,5-difluoro-4-methyl-benzyloxy)-5-[3-(4-hydroxy-5-piperidin-1-yl-pentyl)-ureido]-isothiazole-4-carboxylic Acid Amide The title compound was prepared from [4-carbamoyl-3-(2,5-difluoro-4-methyl-benzyloxy)-isothiazol-5-yl]-carbamic acid phenyl ester and 5-amino-1-piperidin-1-yl-pentan-2-ol by the procedure analogous to Example 6. HPLC ret. time: 3.3 minutes. ¹H NMR (400 MHz, CD₃OD) δ 7.18 (dd, 1H, J=6.0, 9.2 Hz), 7.05 (dd, 1H, J=6.0, 10 Hz), 5.47 (s, 2H), 3.80 (m, 1H), 3.23 (t, 2H, J=6.4 Hz), 2.7-2.4 (m, 7H), 2.25 (s, 3H), 1.8-1.4 (m, nH) ppm; MS (APCl, m/z): 512 [M+H]⁺.

EXAMPLE 8

(R)-3-(2,5-Difluoro-4-methyl-benzyloxy)-5-{3-[4-(3-hydroxy-pyrrolidin-1-yl)-butyl]-ureido}-isothiazole-4-carboxylic Acid Amide The title compound was prepared from [4-carbamoyl-3-(2,5-difluoro-4-methyl-benzyloxy)-isothiazol-5-yl]-carbamic acid phenyl ester and (R)-1-(4-amino-butyl)-pyrrolidin-3-ol by the procedure analogous to Example 6. HPLC ret. time: 3.2 minutes. ¹H NMR (400 MHz, CD₃OD) δ 7.19 (dd, 1H, J=6.0, 9.2 Hz), 7.04 (dd, 1H, J=6.0, 10 Hz), 5.45 (s, 2H), 4.34 (m, 1H), 3.23 (m, 2H), 2.86 (dd, 1H, J=6.0, 10.4 Hz), 2.78 (m, 1H), 2.65-2.54 (m, 4H), 2.25 (s, 3H), 2.14 (m, 1H), 1.73 (m, 1H), 1.56 (m, 4H) ppm; MS (APCl, m/z): 484 [M+H]⁺.

EXAMPLE 9

3-(2,5-Difluoro-4-methyl-benzyloxy)-5-[3-(6-dimethylamino-hexyl)-ureido]-isothiazole-4-carboxylic Acid Amide The title compound was prepared from [4-carbamoyl-3-(2, 5-difluoro-4-methyl-benzyloxy)-isothiazol-5-yl]-carbamic acid phenyl ester and N1,N1-Dimethyl-hexane-1,6-diamine by the procedure analogous to Example 6. HPLC ret. time: 3.4 minutes. $^{1}$H NMR (400 MHz, CD$_3$OD) δ 7.18 (dd, 1H, J=6.0, 9.2 Hz), 7.03 (dd, 1H, J=6.4, 10 Hz), 5.45 (s, 2H), 3.19 (t, 2H, J=7.2 Hz), 2.28 (m, 2H), 2.24 (s, 3H), 2.22 (s, 6H), 1.55-1.45 (m, 4H), 1.35-1.33 (m, 4H) ppm; MS (APCl, m/z): 470 [M+H]$^+$.

EXAMPLE 10

3-(2,5-Difluoro-4-methyl-benzyloxy)-5-{3-[4-(2-hydroxymethyl-pyrrolidin-1-yl)-butyl]-ureido}-isothiazole-4-carboxylic Acid Amide The title compound was prepared from [4-carbamoyl-3-(2,5-difluoro-4-methyl-benzyloxy)-isothiazol-5-yl]-carbamic acid phenyl ester and (S)-[1-(4-amino-butyl)-pyrrolidin-2-yl]-methanol by the procedure analogous to Example 6. HPLC ret. time: 3.2 minutes. $^{1}$H NMR (400 MHz, CD$_3$OD) δ 7.18 (dd, 1H, J=6.0, 9.2 Hz), 7.04 (dd, 1H, J=6.4, 10 Hz), 5.45 (s, 2H), 3.62-3.56 (m, 2H), 3.29-3.23 (m, 2H), 3.02 (m, 1H), 2.78 (m, 1H), 2.83 (m, 1H), 2.51 (m, 2H), 2.24 (d, 3H, J=1.6 Hz), 2.02 (m, 1H), 1.88-1.56 (m, 7H) ppm; MS (APCl, m/z): 498 [M+H]$^+$.

EXAMPLE 11

3-(2,5-Difluoro-4-methyl-benzyloxy)-5-{3-[4-(3-hydroxy-piperidin-1-yl)-butyl]-ureido}-isothiazole-4-carboxylic Acid Amide The title compound was prepared from [4-carbamoyl-3-(2,5-difluoro-4-methyl-benzyloxy)-isothiazol-5-yl]-carbamic acid phenyl ester and 1-(4-amino-butyl)-piperidin-3-ol by the procedure analogous to Example 6. HPLC ret. time: 3.3 minutes. $^{1}$H NMR (400 MHz, CD$_3$OD) δ 7.18 (dd, 1H, J=6.8, 9.6 Hz), 7.04 (dd, 1H, J=5.6, 10 Hz), 5.45 (s, 2H), 3.64 (m, 1H), 3.24-3.22 (m, 2H), 2.90 (m, 1H), 2.73 (m, 1H), 2.37 (m, 2H), 2.25 (d, 3H, J=1.6 Hz), 1.99-1.87 (m, 3H), 1.74 (m, 1H), 1.74-1.53 (m, 6H) ppm; MS (APCl, m/z): 498 [M+H]$^+$.

EXAMPLE 12

3-(2,5-Difluoro-4-methyl-benzyloxy)-5-[3-(5-isopropylamino-pentyl)-ureido]-isothiazole-4-carboxylic Acid Amide The title compound was prepared from [4-carbamoyl-3-(2,5-difluoro-4-methyl-benzyloxy)-isothiazol-5-yl]-carbamic acid phenyl ester and N1-Isopropyl-pentane-1,5-diamine by the procedure analogous to Example 6. HPLC ret. time: 3.4 minutes. $^{1}$H NMR (300 MHz, CD$_3$OD) δ 7.20 (dd, 1H, J=5.7, 9.0 Hz), 7.06 (dd, 1H, J=6.3, 10 Hz), 5.47 (s, 2H), 3.23 (t, 2H, J=6.6 Hz), 2.93 (s, 1H, J=6.3 Hz), 2.70 (m, 2H), 2.27 (d, 3H, J=1.8 Hz), 1.7-1.5 (m, 4H), 1.5-1.3 (m, 2H), 1.11 (d, 6H, J=6.6 Hz) ppm; MS (APCl, m/z): 470 [M+H]$^+$.

EXAMPLE 13

3-(2,3-Difluoro-4-methyl-benzyloxy)-5-{3-[4-(3,4-dihydroxy-pyrrolidin-1-yl)-butyl]-ureido}-isothiazole-4-carboxylic Acid Amide The title compound was prepared from [4-carbamoyl-3-(2,5-difluoro-4-methyl-benzyloxy)-isothiazol-5-yl]-carbamic acid phenyl ester and 1-(4-amino-butyl)-pyrrolidine-3,4-diol by the procedure analogous to Example 6. HPLC ret. time: 3.1 minutes. $^{1}$H NMR (400 MHz, CD$_3$OD) δ 7.17 (t, 1H, J=7.6 Hz), 7.03 (t, 1H, J=7.3 Hz), 5.49 (s, 2H), 4.01 (s, 2H), 3.21 (s, 2H), 2.93 (m, 2H), 2.48 (m, 4H), 2.29 (s, 3H), 1.54 (bs, 4H) ppm; MS (APCl, m/z): 500 [M+H]$^+$.

EXAMPLE 14

3-(4-Chloro-2,6-difluoro-benzyloxy)-5-[3-(3-hydroxy-5-pyrrolidin-1-yl-pentyl)-ureido]-isothiazole-4-carboxylic Acid Amide—Methanesulfonate Salt The title compound was prepared from [4-carbamoyl-3-(2,5-difluoro-4-methyl-benzyloxy)-isothiazol-5-yl]-carbamic acid phenyl ester and 1-amino-5-pyrrolidin-1-yl-pentan-3-ol by the procedure analogous to Example 6. HPLC ret. time: 3.1 minutes. $^{1}$H NMR (400 Mhz, D$_2$O) δ 6.81 (d, 2H, J=7.2 Hz), 5.17 (s, 2H), 3.61 (bm, 1H), 3.47 (bm, 2H), 3.2-3.0 (m, 4H), 2.89 (m, 2H), 2.62 (s, 3H), 1.94 (m, 2H), 1.85-1.2 (m, 6H) ppm; MS (APCl, m/z): 518 [M+H]$^+$.

EXAMPLE 15

3-(4-Chloro-2,6-difluoro-benzyloxy)-5-[3-(3-hydroxy-5-pyrrolidin-1-yl-pentyl)-ureido]-isothiazole-4-carboxylic Acid Amide—Methanesulfonate Salt The title compound was prepared from [4-carbamoyl-3-(2,5-difluoro-4-methyl-benzyloxy)-isothiazol-5-yl]-carbamic acid phenyl ester and 1-amino-5-pyrrolidin-1-yl-pentan-3-ol by the procedure analogous to Example 6. HPLC ret. time: 3.3 minutes. $^{1}$H NMR (400 MHz, CD$_3$OD) δ 7.17 (d, 2H, J=6.4 Hz), 5.51 (s, 2H), 3.64 (bm, 1H), 3.24 (t, 2H, J=6.0 Hz), 2.92 (m, 1H), 2.72 (m, 1H), 2.39 (m, 2H), 1.98 (m, 1H), 1.87 (m, 2H), 1.75 (m, 1H), 1.54 (m, 4H), 1.22 (m, 2H) ppm; MS (APCl, m/z): 517 [M+H]$^+$.

EXAMPLE 16

3-(4-Chloro-2,6-difluoro-benzyloxy)-5-[3-(3-hydroxy-5-pyrrolidin-1-yl-pentyl)-ureido]-isothiazole-4-carboxylic Acid Amine—Methanesulfonate Salt The title compound was prepared from [4-carbamoyl-3-(2,5-difluoro-4-methyl-benzyloxy)-isothiazol-5-yl]-carbamic acid phenyl ester and 1-amino-5-pyrrolidin-1-yl-pentan-3-ol by the procedure analogous to Example 6. HPLC ret. time: 3.3 minutes. $^{1}$H NMR (400 MHz, CD$_3$OD) δ 7.17 (d, 2H, J=6.4 Hz), 5.51 (s, 2H), 3.64 (bm, 1H), 3.24 (t, 2H, J=6.0 Hz), 2.92 (m, 1H), 2.72 (m, 1H), 2.39 (m, 2H), 1.98 (m, 1H), 1.87 (m, 2H), 1.75 (m, 1H), 1.54 (m, 4H), 1.22 (m, 2H) ppm; MS (APCl, m/z): 517 [M+H]$^+$.

EXAMPLE 17

5-(3-{4-[Bis-(2-hydroxy-ethyl)-amino]-butyl}-ureido)-3-(2,5-difluoro-4-methyl-benzyloxy)-isothiazole-4-carboxylic Acid Amide The title compound was prepared from [4-carbamoyl-3-(2,5-difluoro-4-methyl-benzyloxy)-isothiazol-5-yl]-carbamic acid phenyl ester and 2-[(4-amino-butyl)-(2-hydroxy-ethyl)-amino]-ethanol by the procedure analogous to Example 6. HPLC ret. time: 3.1 minutes. $^{1}$H NMR (400 MHz, CD$_3$OD) δ 7.20 (dd, 1H, J=6.0, 9.2 Hz), 7.04 (dd, 1H, J=6.8, 9.6 Hz), 5.45 (s, 2H), 3.63 (t, 4H, J=5.6 Hz), 3.28 (m, 2H), 2.74 (m, 4H), 2.68 (m, 2H), 2.25 (d, 3H, J=2.0 Hz), 1.56 (m, 4H) ppm; MS (APCl, m/z): 502 [M+H]$^+$.

EXAMPLE 18

3-(2,5-Difluoro-4-methyl-benzyloxy)-5-{3-[4-(3,4-dihydroxy-pyrrolidin-1-yl)-butyl]-ureido}-isothiazole-4-carboxylic Acid Amide The title compound was prepared from [4-carbamoyl-3-(2,5-difluoro-4-methyl-benzyloxy)-isothiazol-5-yl]-carbamic acid phenyl ester and 1-(4-amino-butyl)-pyrrolidine-3,4-diol by the procedure analogous to Example 8. HPLC ret. time: minutes. $^1$H NMR (400 MHz, CD$_3$OD) δ 7.20 (dd, 1H, J=6.0, 9.2 Hz), 7.04 (dd, 1H, J=6.8, 9.6 Hz), 5.45 (s, 2H), 3.63 (t, 4H, J=5.6 Hz), 3.28 (m), 2.74 (m, 4H), 2.68 (m, 2H), 2.25 (d, 3H, J=2.0 Hz), 1.56 (m, 4H) ppm.

EXAMPLE 19

5-[3-(4-tert-Butylamino-3-hydroxy-butyl)-ureido]-3-(2,5-difluoro-4-methyl-benzyloxy)-isothiazole-4-carboxylic Acid Amide The title compound was prepared from [4-carbamoyl-3-(2,5-difluoro-4-methyl-benzyloxy)-isothiazol-5-yl]-carbamic acid phenyl ester and 4-amino-1-tert-butylamino-butan-2-ol by the procedure analogous to Example 6. HPLC ret. time: 3.3 minutes. $^1$H NMR (400 MHz, CD$_3$OD) δ 7.18 (dd, 1H, J=6.8, 9.6 Hz), 7.04 (dd, 1H, J=6.4, 10 Hz), 5.45 (s, 2H), 3.66 (m, 1H), 3.34 (t, 2H, J=7.6 Hz), 2.58 (m, 2H), 2.25 (s, 3H), 1.69-1.60 (m, 2H), 1.12 (s, 9H) ppm; MS (APCl, m/z): 486 [M+H]$^+$.

EXAMPLE 20

3-(4-Chloro-2,6-difluoro-benzyloxy)-5-{3-[3-(4-methyl-piperazin-1-yl)-propyl]-ureido}-isothiazole-4-carboxylic Acid Amide—Hydrochloride Salt The title compound was prepared from [4-carbamoyl-3-(2,6-difluoro-4-chloro-benzyloxy)-isothiazol-5-yl]-carbamic acid phenyl ester and 3-(4-methyl-piperazin-1-yl)-propylamine by the procedure analogous to Example 6. $^1$H NMR (400 MHz, D$_2$O) δ 6.86 (bm, 2H), 5.20 (s, 2H), 3.4-2.6 (bm, 8H), 3.10 (b, 2H), 2.63 (b, 5H), 1.67 (m, 2H) ppm; MS (APCl, m/z): 503 [M+H]$^+$.

EXAMPLE 21

3-(4-Chloro-2,6-difluoro-benzyloxy)-5-[3-(3-hydroxy-5-isopropylamino-pentyl)-ureido]-isothiazole-4-carboxylic Acid Amide The title compound was prepared from [4-carbamoyl-3-(2,6-difluoro-4-chloro-benzyloxy)-isothiazol-5-yl]-carbamic acid phenyl ester and 1-amino-5-isopropylamino-pentan-3-ol by the procedure analogous to Example 6. HPLC ret. time: 3.2 minutes. $^1$H NMR (400 MHz, CD$_3$OD) δ 7.17 (d, 1H, J=7.6 Hz), 5.52 (s, 2H), 3.69 (m, 1H), 3.34 (t, 2H, J=6.4 Hz), 2.80 (s, 1H, J=6.0 Hz), 2.73 (m, 2H), 1.68-1.58 (m, 4H), 1.06 (d, 6H, J=6.0 Hz) ppm; MS (APCl, m/z): 506 [M+H]$^+$.

EXAMPLE 22

3-(4-Chloro-2,6-difluoro-benzyloxy)-5-[3-(3-hydroxy-5-isopropylamino-pentyl)-ureido]-isothiazole-4-carboxylic Acid Amide The title compound was prepared from [4-carbamoyl-3-(2,6-difluoro-4-chloro-benzyloxy)-isothiazol-5-yl]-carbamic acid phenyl ester and 1-amino-5-isopropylamino-pentan-3-ol by the procedure analogous to Example 6. HPLC ret. time: 3.2 minutes. $^1$H NMR (400 MHz, CD$_3$OD) δ 7.17 (d, 1H, J=7.6 Hz), 5.52 (s, 2H), 3.69 (m, 1H), 3.34 (t, 2H, J=6.4 Hz), 2.80 (s, 1H, J=6.0 Hz), 2.73 (m, 2H), 1.68-1.58 (m, 4H), 1.06 (d, 6H, J=6.0 Hz) ppm; MS (APCl, m/z): 506 [M+H]$^+$.

EXAMPLE 23

3-(2,5-Difluoro-4-methyl-benzyloxy)-5-(3-{6-[4-(2-hydroxy-ethyl)-piperazin-1-yl]-hexyl}-ureido)-isothiazole-4-carboxylic Acid Amide The title compound was prepared from [4-carbamoyl-3-(2,5-difluoro-4-methyl-benzyloxy)-isothiazol-5-yl]-carbamic acid phenyl ester and 2-[4-(6-amino-hexyl)-piperazin-1-yl]-ethanol by the procedure analogous to Example 6. HPLC ret. time: 3.0 minutes. $^1$H NMR (400 MHz, CD$_3$OD) δ 7.17 (d, 1H, J=6.4, 9.6 Hz), 7.01 (m, 1H), 5.44 (s, 2H), 3.64 (t, 2H, J=5.6 Hz), 3.18 (t, 2H, J=6.8 Hz), 2.7-2.4 (bm, 8H), 2.50 (t, 2H, J=6.0 Hz), 2.23 (m, 2H), 2.23 (s, 3H), 1.50 (m, 4H), 1.35 (m, 4H) ppm; MS (APCl, m/z): 555 [M+H]$^+$.

EXAMPLE 24

3-(4-Chloro-2,5-difluoro-benzyloxy)-5-[3-(6-dimethylamino-hexyl)-ureido]-isothiazole-4-carboxylic Acid Amide The title compound was prepared from [4-carbamoyl-3-(2,5-difluoro-4-methyl-benzyloxy)-isothiazol-5-yl]-carbamic acid phenyl ester and 2-[4-(6-amino-hexyl)-piperazin-1-yl]-ethanol by the procedure analogous to Example 6. HPLC ret. time: 3.0 minutes. $^1$H NMR (400 MHz, CD$_3$OD) δ 7.17 (d, 1H, J=6.4, 9.6 Hz), 7.01 (m, 1H), 5.44 (s, 2H), 3.64 (t, 2H, J=5.6 Hz), 3.18 (t, 2H, J=6.8 Hz), 2.7-2.4 (bm, 8H), 2.50 (t, 2H, J=6.0 Hz) 2.33 (m, 2H), 2.23 (s, 3H), 1.50 (m, 4H), 1.35 (m, 4H) ppm; MS (APCl, m/z): 555 [M+H]$^+$.

EXAMPLE 25

5-{3-[3-(4-Methyl-piperazin-1-yl)-propyl]-ureido}-3-(2,3,6-trifluoro-4-methyl-benzyloxy)-isothiazole-4-carboxylic Acid Amide The title compound was prepared from [4-carbamoyl-3-(2,3,6-trifluoro-4-methyl-benzyloxy)-isothiazol-5-yl]-carbamic acid phenyl ester and 3-(4-methyl-piperazin-1-yl)-propylamine by the procedure analogous to Example 1. MS (APCl, m/z): 501 [M+H]$^+$.

EXAMPLE 26

3-(2-Fluoro-4-methyl-benzyloxy)-5-{3-[3-(4-methyl-piperazin-1-yl)-propyl]-ureido}-isothiazole-4-carboxylic Acid Amide The title compound was prepared from [4-carbamoyl-3-(2-fluoro-4-methyl-benzyloxy)-isothiazol-5-yl]-carbamic acid phenyl ester and 3-(4-methyl-piperazin-1-yl)-propylamine by the procedure analogous to Example 1. MS (APCl, m/z): 465 [M+H]$^+$.

EXAMPLE 27

3-(2-Fluoro-4-methyl-benzyloxy)-5-[amino-pentyl)-ureido]-isothiazole-4-carboxylic Acid Amide The title compound was prepared from [4-carbamoyl-3-(2-fluoro-4-methyl-benzyloxy)-isothiazol-5-yl]-carbamic acid phenyl ester and N-isopropyl-pentane-1,5-diamine by the procedure analogous to Example 1. MS (APCl, m/z): 452 [M+H]$^+$.

EXAMPLE 28

3-(2,6-Difluoro-4-methyl-benzyloxy)-5-[3-(4-pyrrolidin-1-yl-butyl)-ureido]-isothiazole-4-carboxylic Acid Amide The title compound was prepared from [4-carbamoyl-3-(2,6-difluoro-4-methyl-benzyloxy)-isothiazol-5-yl]-carbamic acid phenyl ester and 4-pyrrolidin-1-yl-butylamine by the procedure analogous to Example 1. $^1$H NMR (400 MHz, CDCl$_3$) δ 1.63 (br. s, 4H), 1.83 (br. s, 4H), 2.34 (s, 3H), 2.46-2.52 (m, 6H), 3.28 (s, 2H), 5.40 (s, 1H), 5.50 (s, 2H), 6.74 (d, J=8.3 Hz, 2H), 6.98 (s, 1H), 7.94 (br. s, 1H), 10.83 (br. s, 1H) ppm; MS (APCl, m/z): 468 [M+H]$^+$.

EXAMPLE 29

3-(2,6-Difluoro-4-methyl-benzyloxy)-5-(3-{4-[4-(2-hydroxy-ethyl)-piperazin-1-yl]-butyl}-ureido)-isothiazole-4-carboxylic Acid Amide The title compound was prepared from [4-carbamoyl-3-(2,6-difluoro-4-methyl-benzyloxy)-isothiazol-5-yl]-carbamic acid phenyl ester and 2-[4-(4-amino-butyl)-piperazin-1-yl]-ethanol by the procedure analogous to Example 1. MS (APCl, m/z): 527 [M+H]$^+$.

EXAMPLE 30

3-(4-Bromo-2,6-difluoro-benzyloxy)-5-[3-(4-pyrrolidin-1yl-butyl)-ureido]-isothiazole-4-carboxylic Acid Amide The title compound was prepared from [3-(4-bromo-2,6-difluoro-benzyloxy)-4-carbamoyl-isothiazol-5-yl]-carbamic acid phenyl ester and 4-pyrrolidin-1-yl-butylamine by the procedure analogous to Example 1. MS (APCl, m/z): 532 and 534 [M+H]$^+$.

EXAMPLE 31

3-(2,6-Difluoro-4-methyl-benzyloxy)-5-[3-(4-hydroxy-5-piperidin-1-yl-pentyl)-ureido]-isothiazole-4-carboxylic Acid Amide The title compound was prepared from [4-carbamoyl-3-(2,6-difluoro-4-methyl-benzyloxy)-isothiazol-5-yl]-carbamic acid phenyl ester and 5-amino-1-piperidin-1-yl-pentan-2-ol by the procedure analogous to Example 1. MS (APCl, m/z): 512 [M+H]$^+$.

EXAMPLE 32

3-(4-Bromo-2,3,6-trifluoro-benzyloxy)-5-{3-[3-(4-methyl-piperazin-1-yl)-propyl]-ureido}-isothiazole-4-carboxylic Acid Amide The title compound was prepared from [3-(4-bromo-2,3,6-trifluoro-benzyloxy)-4-carbamoyl-isothiazol-5-yl]-carbamic acid phenyl ester and 3-(4-methyl-piperazin-1-yl)-propylamine by the procedure analogous to Example 1. MS (APCl, m/z): 565 and 567 [M+H]$^+$.

EXAMPLE 33

3-(2,6-Difluoro-4-methyl-benzyloxy)-5-{3-[3-(4-methyl-piperazin-1-yl)-propyl]-ureido}-isothiazole-4-carboxylic Acid Amide The title compound was prepared from [4-Carbamoyl-3-(2,6-difluoro-4-methyl-benzyloxy)-isothiazol-5-yl]-carbamic acid phenyl ester and and 3-(4-methyl-piperazin-1-yl)-propylamine by the procedure analogous to Example 1. MS (APCl, m/z): 483 [M+H]$^+$.

EXAMPLE 34

3-(2,6-Difluoro-4-methyl-benzyloxy)-5-[3-(3-hydroxy-5-pyrrolidin-1-yl-pentyl)-ureido]-isothiazole-4-carboxylic Acid Amide The title compound was prepared from [4-carbamoyl-3-(2,6-difluoro-4-methyl-benzyloxy)-isothiazol-5-yl]-carbamic acid phenyl ester and 1-amino-5-pyrrolidin-1-yl-pentan-3-ol by the procedure analogous to Example 1. MS (APCl, m/z): 498 [M+H]$^+$.

EXAMPLE 35

5-[3-(4-Pyrrolidin-1-yl-butyl)-ureido]-3-(2,3,6-trifluoro-4-methyl-benzyloxy)-isothiazole-4-carboxylic Acid Amide The title compound was prepared from [4-carbamoyl-3-(2,3,6-trifluoro-4-methyl-benzyloxy)-isothiazol-5-yl]-carbamic acid phenyl ester and 4-pyrrolidin-1-yl-butylamine by the procedure analogous to Example 1. MS (APCl, m/z): 486 [M+H]$^+$.

EXAMPLE 36

5-[3-(3-Hydroxy-5-pyrrolidin-1-yl-pentyl)-ureido]-3-(2,3,6-trifluoro-4-methyl-benzyloxy)-isothiazole-4-carboxylic acid amide The title compound was prepared from [4-carbamoyl-3-(2,3,6-trifluoro-4-methyl-benzyloxy)-isothiazol-5-yl]-carbamic acid phenyl ester and 1-amino-5-pyrrolidin-1-yl-pentan-3-ol by the procedure analogous to Example 1. MS (APCl, m/z): 516 [M+H]$^+$.

EXAMPLE 37

5-{3-[2-(1-Methyl-pyrrolidin-2-yl)-ethyl]-ureido}-3-(2,3,6-trifluoro-4-methyl-benzyloxisothiazole-4-carboxylic Acid Amide The title compound was prepared from [4-carbamoyl-3-(2,3,6-trifluoro-4-methyl-benzyloxy)-isothiazol-5-yl]-carbamic acid phenyl ester and 2-(1-methyl-pyrrolidin-2-yl)-ethylamine by the procedure analogous to Example 1. MS (APCl, m/z): 472 [M+H]$^+$.

EXAMPLE 38

5-[3-(4-Dimethylamino-butyl)-ureido]-3-(2,3,6-trifluoro-4-methyl-benzyloxy)-isothiazole-4-carboxylic Acid Amide The title compound was prepared from [4-carbamoyl-3-(2,3,6-trifluoro-4-methyl-benzyloxy)-isothiazol-5-yl]-carbamic acid phenyl ester and N,N-dimethyl-butane-1,4-diamine by the procedure analogous to Example 1. MS (APCl, m/z): 460 [M+H]$^+$.

EXAMPLE 39

5-[3-(3-Dimethylamino-propyl)-ureido]-3-(2,3,6-trifluoro-4-methyl-benzyloxy-isothiazole-4-carboxylic Acid Amide The title compound was prepared from [4-carbamoyl-3-(2,3,6-trifluoro-4-methyl-benzyloxy)-isothiazol-5-yl]-carbamic acid phenyl ester and N,N-dimethyl-propane-1,3-diamine by the procedure analogous to Example 1. MS (APCl, m/z): 446 [M+H]$^+$.

EXAMPLE 40

5-[3-(3-Hydroxy-5-isopropylamino-pentyl)-ureido]-3-(2,3,6-trifluoro-4-methyl-benzyloxy)-isothiazole-4-carboxylic Acid Amide The title compound was prepared from [4-carbamoyl-3-(2,3,6-trifluoro-4-methyl-benzyloxy)-isothiazol-5-yl]-carbamic acid phenyl ester and 1-amino-5-isopropylamino-pentan-3-ol by the procedure analogous to Example 1. MS (APCl, m/z): 504 [M+H]$^+$.

EXAMPLE 41

5-[3-(3-Isopropylamino-propyl)-ureido]-3-(2,3,6-trifluoro-4-methyl-benzyloxy)-isothiazole-4-carboxylic Acid Amide The title compound was prepared from [4-carbamoyl-3-(2,3,6-trifluoro-4-methyl-benzyloxy)-isothiazol-5-yl]-carbamic acid phenyl ester and N-isopropyl-propane-1,3-diamine by the procedure analogous to Example 1. MS (APCl, m/z): 460 [M+H]$^+$.

EXAMPLE 42

5-{3-[4-(4-Methyl-piperazin-1-yl)-butyl]-ureido}-3-(2,3,6-trifluoro-4-methyl-benzyloxy)-isothiazole-4-carboxylic Acid Amide The title compound was prepared from [4-carbamoyl-3-(2,3,6-trifluoro-4-methyl-benzyloxy)-isothiazol-5-yl]-carbamic acid phenyl ester and 4-(4-methyl-piperazin-1-yl)-butylamine by the procedure analogous to Example 1. MS (APCl, m/z): 515 [M+H]$^+$.

EXAMPLE 43

5-(3-{4-[4-(2-Hydroxy-ethyl)-piperazin-1-yl]-butyl}-ureido)-3-(2,3,6-trifluoro-4-benzyloxy)-isothiazole-4-carboxylic Acid Amide The title compound was prepared from [4-carbamoyl-3-(2,3,6-trifluoro-4-methyl-benzyloxy)-isothiazol-5-yl]-carbamic acid phenyl ester and 2-[4-(4-amino-butyl)-piperazin-1-yl]-ethanol by the procedure analogous to Example 1. MS (APCl, m/z): 545 [M+H]$^+$.

EXAMPLE 44

5-[3-(3-Pyrrolidin-1-yl-propyl)-ureido]-3-(2,3,6-trifluoro-4-methyl-benzyloxy)-isothiazole-4-carboxylic Acid Amide The title compound was prepared from [4-carbamoyl-3-(2,3,6-trifluoro-4-methyl-benzyloxy)-isothiazol-5-yl]-carbamic acid phenyl ester and 3-pyrrolidin-1-yl-propylamine by the procedure analogous to Example 1. MS (APCl, m/z): 472 [M+H]$^+$.

EXAMPLE 45

5-[3-(4-Hydroxy-5-piperidin-1-yl-pentyl)-ureido]-3-(2,3,6-trifluoro-4-methyl-benzyloxy)-isothiazole-4-carboxylic Acid Amide The title compound was prepared from [4-carbamoyl-3-(2,3,6-trifluoro-4-methyl-benzyloxy)-isothiazol-5-yl]-carbamic acid phenyl ester and 5-amino-1-piperidin-1-yl-pentan-2-ol by the procedure analogous to Example 1. MS (APCl, m/z): 530 [M+H]$^+$.

EXAMPLE 46

5-(3-{4-[Ethyl-(2-hydroxy-ethyl)-amino]-butyl}-ureido)-3-(2,3,6-trifluoro-4-methyl-benzyloxy)-isothiazole-4-carboxylic Acid Amide The title compound was prepared from [4-carbamoyl-3-(2,3,6-trifluoro-4-methyl-benzyloxy)-isothiazol-5-yl]-carbamic acid phenyl ester and 2-[(4-amino-butyl)-ethyl-amino]-ethanol by the procedure analogous to Example 1. MS (APCl, m/z): 504 [M+H]$^+$.

EXAMPLE 47

3-(4-Bromo-2,6-difluoro-benzyloxy)-5-{3-[3-(4-methyl-piperazin-1-yl)-propyl]-ureido}-isothiazole-4-carboxylic Acid Amide The title compound was prepared from [3-(4-bromo-2,6-difluoro-benzyloxy)-4-carbamoyl-isothiazol-5-yl]-carbamic acid phenyl ester and 3-(4-methyl-piperazin-1-yl)-propylamine by the procedure analogous to Example 1. MS (APCl, m/z): 547 and 549 [M+H]$^+$.

EXAMPLE 48

3-(2,6-Difluoro-4-methyl-benzyloxy)-5-{3-[2-(1-methyl-pyrrolidin-2-yl)-ethyl]-ureido}-isothiazole-4-carboxylic Acid Amide The title compound was prepared from [4-carbamoyl-3-(2,6-difluoro-4-methyl-benzyloxy)-isothiazol-5-yl]-carbamic acid phenyl ester and 2-(1-methyl-pyrrolidin-2-yl)-ethylamine by the procedure analogous to Example 1. MS (APCl, m/z): 454 [M+H]$^+$.

EXAMPLE 49

3-(2,6-Difluoro-4-methyl-benzyloxy)-5-[3-(4-dimethylamino-butyl)-ureido]-isothiazole-4-carboxylic Acid Amide The title compound was prepared from [4-carbamoyl-3-(2,6-difluoro-4-methyl-benzyloxy)-isothiazol-5-yl]-carbamic acid phenyl ester and N,N-dimethyl-butane-1,4-diamine by the procedure analogous to Example 1. MS (APCl, m/z): 442 [M+H]$^+$.

EXAMPLE 50

3-(2,6-Difluoro-4-methyl-benzyloxy)-5-[3-(3-dimethylamino-propyl)-ureido]-isothiazole-4-carboxylic Acid Amide The title compound was prepared from [4-carbamoyl-3-(2,6-difluoro-4-methyl-benzyloxy)-isothiazol-5-yl]-carbamic acid phenyl ester and N,N-dimethyl-propane-1,3-diamine by the procedure analogous to Example 1. MS (APCl, m/z): 428 [M+H]$^+$.

EXAMPLE 51

3-(4-Bromo-2,3,6-trifluoro-benzyloxy)-5-[3-(4-pyrrolidin-1-yl-butyl)-ureido]-isothiazole-4-carboxylic Acid Amide The title compound was prepared from [3-(4-bromo-2,3,6-trifluoro-benzyloxy)-4-carbamoyl-isothiazol-5-yl]-carbamic acid phenyl ester and 4-pyrrolidin-1-yl-butylamine by the procedure analogous to Example 1. MS (APCl, m/z): 550 and 552 [M+H]$^+$.

EXAMPLE 52

5-[3-(3-Methylamino-propyl)-ureido]-3-(2,3,6-trifluoro-4-methyl-benzyloxy)-isothiazole-4-carboxylic Acid Amide The title compound was prepared from [4-carbamoyl-3-(2,3,6-trifluoro-4-methyl-benzyloxy)-isothiazol-5-yl]-carbamic acid phenyl ester and N-methyl-propane-1,3-diamine by the procedure analogous to Example 1. MS (APCl, m/z): 432 [M+H]$^+$.

EXAMPLE 53

5-[3-(3-Amino-propyl)-3-methyl-ureido]-3-(2,3,6-trifluoro-4-methyl-benzyloxy)-isothiazole-4-carboxylic Acid Amide The title compound was prepared from [4-carbamoyl-3-(2,3,6-trifluoro-4-methyl-benzyloxy)-isothiazol-5-yl]-carbamic acid phenyl ester and N-methyl-propane-1,3-diamine by the procedure analogous to Example 1. MS (APCl, m/z): 432 [M+H]$^+$.

EXAMPLE 54

5-[3-(4-Diethylamino-butyl)-ureido]-3-(2,3,6-trifluoro-4-methyl-benzyloxy)-isothiazole-4-carboxylic Acid Amide The title compound was prepared from [4-carbamoyl-3-(2,3,6-trifluoro-4-methyl-benzyloxy)-isothiazol-5-yl]-carbamic acid phenyl ester and N,N-diethyl-butane-1,4-diamine by the procedure analogous to Example 1. MS (APCl, m/z): 488 [M+H]$^+$.

EXAMPLE 55

3-(2,6-Difluoro-4-methyl-benzyloxy)-5-[3-(3-pyrrolidin-1-yl-propyl)-ureido]-isothiazole-4-carboxylic Acid Amide The title compound was prepared from [4-carbamoyl-3-(2,6-difluoro-4-methyl-benzyloxy)-isothiazol-5-yl]-carbamic acid phenyl ester and 3-pyrrolidin-1-yl-propylamine by the procedure analogous to Example 1. MS (APCl, m/z): 454 [M+H]$^+$.

EXAMPLE 56

3-(3-Chloro-2,6-difluoro-4-methyl-benzyloxy)-5-[3-(4-dimethylamino-butyl)-ureido]-isothiazole-4-carboxylic Acid Amide The title compound was prepared [4-carbamoyl-3-(3-chloro-2,6-difluoro-4-methyl-benzyloxy)-isothiazol-5-yl]-carbamic acid phenyl ester and N,N-diethyl-butane-1,4-diamine by the procedure analogous to Example 1. MS (APCl, m/z): 476 [M+H]$^+$.

EXAMPLE 57

5-(3-{4-[Bis-(2-hydroxy-ethyl)-amino]-butyl}-ureido)-3-(2,6-difluoro-4-methyl-benzyloxy)-isothiazole-4-carboxylic Acid Amide The title compound was prepared from [4-carbamoyl-3-(2,6-difluoro-4-methyl-benzyloxy)-isothiazol-5-yl]-carbamic acid phenyl ester and 2-[(4-amino-butyl)-(2-hydroxy-ethyl)-amino]-ethanol by the procedure analogous to Example 1. MS (APCl, m/z): 502 [M+H]$^+$.

The following specific compounds were prepared using the general synthetic procedures described above with reference to Schemes 1-5 and the specific synthetic procedures described in the above preparations and examples.

(3-tert-Butyl-isothiazol-5-yl)-(6,7-dimethoxy-quinolin-4-yl)-amine;
3-Ethylsulfanyl-5-(3-hexyl-ureido)-isothiazole-4-carboxylic acid amide;
5-(3-Benzyl-ureido)-3-ethylsulfanyl-isothiazole-4-carboxylic acid amide;
3-Ethylsulfanyl-5-(3-ethyl-ureido)-isothiazole-4-carboxylic acid amide;
3-Ethylsulfanyl-5-[(pyrrolidine-1-carbonyl)-amino]-isothiazole-4-carboxylic acid amide;
5-(3-Butyl-ureido)-3-ethylsulfanyl-isothiazole-4-carboxylic acid amide;
5-(3,3-Dimethyl-ureido)-3-propylsulfanyl-isothiazole-4-carboxylic acid amide;
5-(3-Methyl-ureido)-3-propylsulfanyl-isothiazole-4-carboxylic acid amide;
5-(3-Butyl-ureido)-3-propylsulfanyl-isothiazole-4-carboxylic acid amide;
5-(3-Methyl-ureido)-3-pentylsulfanyl-isothiazole-4-carboxylic acid amide;
5-(3,3-Dimethyl-ureido)-3-pentylsulfanyl-isothiazole-4-carboxylic acid amide;
5-(3,3-Dimethyl-ureido)-3-isopropylsulfanyl-isothiazole-4-carboxylic acid amide;
3-Pentylsulfanyl-5-ureido-isothiazole-4-carboxylic acid amide;
3-Benzylsulfanyl-5-(3,3-dimethyl-ureido)-isothiazole-4-carboxylic acid amide;
5-(3,3-Dimethyl-ureido)-3-propoxy-isothiazole-4-carboxylic acid amide;
3-Butoxy-4-carbamoyl-isothiazol-5-yl)-carbamic acid ethyl ester;
5-(3,3-Dimethyl-ureido)-3-phenethylsulfanyl-isothiazole-4-carboxylic acid amide;
5-(3,3-Dimethyl-ureido)-3-hexylsulfanyl-isothiazole-4-carboxylic acid amide;
3-(4-Chloro-butylsulfanyl)-5-(3,3-dimethyl-ureido)-isothiazole-4-carboxylic acid amide;
3-Butoxy-5-(3,3-dimethyl-ureido)-isothiazole-4-carboxylic acid amide;
3-Butylsulfanyl-5-(3,3-dimethyl-ureido)-isothiazole-4-carboxylic acid amide;
3-Cyclohexylsulfanyl-5-(3-methyl-ureido)-isothiazole-4-carboxylic acid amide;
5-(3,3-Dimethyl-ureido)-3-(3-methyl-butylsulfanyl)-isothiazole-4-carboxylic acid amide;
5-(3,3-Dimethyl-ureido)-3-pentyloxy-isothiazole-4-carboxylic acid amide;
5-(3,3-Dimethyl-ureido)-3-prop-2-ynylsulfanyl-isothiazole-4-carboxylic acid amide;
5-(3,3-Dimethyl-ureido)-3-heptylsulfanyl-isothiazole-4-carboxylic acid amide;
5-(3,3-Dimethyl-ureido)-3-isobutylsulfanyl-isothiazole-4-carboxylic acid amide;
5-(3-Methyl-ureido)-3-phenylsulfanyl-isothiazole-4-carboxylic acid amide;
5-(3,3-Dimethyl-ureido)-3-(3-hydroxy-butylsulfanyl)-isothiazole-4-carboxylic acid amide;
5-Amino-3-propoxy-isothiazole-4-carboxylic acid amide;
3-Propoxy-5-(3-propyl-ureido)-isothiazole-4-carboxylic acid amide;
5-(3-Butyl-ureido)-3-propoxy-isothiazole-4-carboxylic acid amide;
5-(3-Ethyl-ureido)-3-propoxy-isothiazole-4-carboxylic acid amide;
5-(3-Pentyl-ureido)-3-propoxy-isothiazole-4-carboxylic acid amide;
5-(3-Hexyl-ureido)-3-propoxy-isothiazole-4-carboxylic acid amide;
5-[(Azetidine-1-carbonyl)-amino]-3-propoxy-isothiazole-4-carboxylic acid amide;
Piperidine-1-carboxylic acid (4-carbamoyl-3-propoxy-isothiazol-5-yl)-amide;
5-(3-Phenethyl-ureido)-3-propoxy-isothiazole-4-carboxylic acid amide;
3-Propoxy-5-[(pyrrolidine-1-carbonyl)-amino]-isothiazole-4-carboxylic acid amide;
5-(3,3-Dimethyl-ureido)-3-methylsulfanyl-isothiazole-4-carboxylic acid amide;
3-Cyclopentylsulfanyl-5-(3,3-dimethyl-ureido)-isothiazole-4-carboxylic acid amide;
5-(3-Benzyl-ureido)-3-propoxy-isothiazole-4-carboxylic acid amide;
5-(3,3-Dimethyl-ureido)-3-(naphthalen-1-ylmethylsulfanyl)-isothiazole-4-carboxylic acid amide;
3-[4-Carbamoyl-5-(3,3-dimethyl-ureido)-isothiazol-3-ylsulfany]-propionic acid;
3-Propoxy-5-ureido-isothiazole-4-carboxylic acid amide;
3-Propoxy-5-(3-pyridin-3-yl-ureido)-isothiazole-4-carboxylic acid amide;
5-(3,3-Dimethyl-ureido)-3-(4-methyl-benzylsulfanyl)-isothiazole-4-carboxylic acid amide;
5-(3,3-Dimethyl-ureido)-3-(4-methoxy-benzylsulfanyl)-isothiazole-4-carboxylic acid amide;
5-(3,3-Dimethyl-ureido)-3-(4-methyl-pentylsulfanyl)-isothiazole-4-carboxylic acid amide;
5-(3-Butyl-ureido)-3-pentylsulfanyl-isothiazole-4-carboxylic acid amide;
5-Acetylamino-3-pentylsulfanyl-isothiazole-4-carboxylic acid amide;
5-Benzoylamino-3-pentylsulfanyl-isothiazole-4-carboxylic acid amide;
3-Decyloxy-5-(3,3-dimethyl-ureido)-isothiazole-4-carboxylic acid amide;
Morpholine-4-carboxylic acid (4-carbamoyl-3-pentylsulfanyl-isothiazol-5-yl)-amide;
5-[3-(2-Hydroxy-ethyl)-ureido]-3-pentylsulfanyl-isothiazole-4-carboxylic acid amide;
5-[(3-Hydroxy-azetidine-1-carbonyl)-amino]-3-pentylsulfanyl-isothiazole-4-carboxylic acid amide;
5-[3-(3-Hydroxy-propyl)-ureido]-3-pentylsulfanyl-isothiazole-4-carboxylic acid amide;
3-Pentylsulfanyl-5-(3-propyl-ureido)-isothiazole-4-carboxylic acid amide;
5-(3,3-Dimethyl-ureido)-3-hexyloxy-isothiazole-4-carboxylic acid amide;
5-(3,3-Dimethyl-ureido)-3-heptyloxy-isothiazole-4-carboxylic acid amide;
5-(3-Isobutyl-ureido)-3-pentylsulfanyl-isothiazole-4-carboxylic acid amide;
5-(3-Furan-2-ylmethyl-ureido)-3-pentylsulfanyl-isothiazole-4-carboxylic acid amide;
5-(3,3-Dimethyl-ureido)-3-octyloxy-isothiazole-4-carboxylic acid amide;
5-(3,3-Dimethyl-ureido)-3-(3-methyl-benzyloxy)-isothiazole-4-carboxylic acid amide;
3-Allyloxy-5-(3,3-dimethyl-ureido)-isothiazole-4-carboxylic acid amide;
5-(3,3-Dimethyl-ureido)-3-nonyloxy-isothiazole-4-carboxylic acid amide;
5-(3,3-Dimethyl-ureido)-3-(naphthalen-2-ylmethylsulfanyl)-isothiazole-4-carboxylic acid amide;
5-(3,3-Dimethyl-ureido)-3-(3-methyl-but-2-enyloxy)-isothiazole-4-carboxylic acid amide;

5-(3,3-Dimethyl-ureido)-3-(3-phenyl-allyloxy)-isothiazole-4-carboxylic acid amide;
5-(3,3-Dimethyl-ureido)-3-pent-2-enyloxy-isothiazole-4-carboxylic acid amide;
5-(3,3-Dimethyl-ureido)-3-(2-methyl-allyloxy)-isothiazole-4-carboxylic acid amide;
3-Benzyloxy-5-(3,3-dimethyl-ureido)-isothiazole-4-carboxylic acid amide;
5-(3,3-Dimethyl-ureido)-3-phenethyloxy-isothiazole-4-carboxylic acid amide;
3-(2-Cyclohexyl-ethoxy)-5-(3,3-dimethyl-ureido)-isothiazole-4-carboxylic acid amide;
5-(3-Ethyl-ureido)-3-pentylsulfanyl-isothiazole-4-carboxylic acid amide;
5-[3-(3-Dimethylamino-propyl)-ureido]-3-pentylsulfanyl-isothiazole-4-carboxylic acid amide;
5-(3,3-Dimethyl-ureido)-3-(2-fluoro-3-methyl-benzyloxy)-isothiazole-4-carboxylic acid amide;
5-(3,3-Dimethyl-ureido)-3-(3-methoxy-benzyloxy)-isothiazole-4-carboxylic acid amide;
3-Pentylsulfanyl-5-(3-thiophen-2-ylmethyl-ureido)-isothiazole-4-carboxylic acid amide;
5-[3-(3-Methyl-butyl)-ureido]-3-pentylsulfanyl-isothiazole-4-carboxylic acid amide;
5-[3-(4-Hydroxy-butyl)-ureido]-3-pentylsulfanyl-isothiazole-4-carboxylic acid amide;
5-[3-(3-Methoxy-propyl)-ureido]-3-pentylsulfanyl-isothiazole-4-carboxylic acid amide;
4-Hydroxy-piperidine-1-carboxylic acid (4-carbamoyl-3-pentylsulfanyl-isothiazol-5-yl)-amide;
5-(3,3-Dimethyl-ureido)-3-(3-trifluoromethyl-benzyloxy)-isothiazole-4-carboxylic acid amide;
5-(3,3-Dimethyl-ureido)-3-(4-methyl-benzyloxy)-isothiazole-4-carboxylic acid amide;
5-(3,3-Dimethyl-ureido)-3-(naphthalen-2-ylmethoxy)-isothiazole-4-carboxylic acid amide;
3-Heptyloxy-5-(3-methyl-urcido)-isothiazole-4-carboxylic acid amide;
3-(3,5-Dimethyl-benzyloxy)-5-(3,3-dimethyl-ureido)-isothiazole-4-carboxylic acid amide;
5-(3,3-Dimethyl-ureido)-3-(2-methyl-benzyloxy)-isothiazole-4-carboxylic acid amide;
[3-(4-Carbamoyl-3-pentylsulfanyl-isothiazol-5-yl)-ureido]-acetic acid methyl ester;
5-[3-(5-Methyl-furan-2-ylmethyl)-ureido]-3-pentylsulfanyl-isothiazole-4-carboxylic acid amide;
5-[3-(2-Hydroxy-propyl)-ureido]-3-pentylsulfanyl-isothiazole-4-carboxylic acid amide;
5-[(2,5-Dihydro-pyrrole-1-carbonyl)-amino]-3-pentylsulfanyl-isothiazole-4-carboxylic acid amide;
5-{3-[2-(1H-midazol-4-yl)-ethyl]-ureido}-3-pentylsulfanyl-isothiazole-4-carboxylic acid amide;
3-Pentylsulfanyl-5-[3-(tetrahydro-furan-2-ylmethyl)-ureido]-isothiazole-4-carboxylic acid amide;
5-[3-(2-Cyano-ethyl)-ureido]-3-pentylsulfanyl-isothiazole-4-carboxylic acid amide;
5-(3-Cyclopropylmethyl-ureido)-3-pentylsulfanyl-isothiazole-4-carboxylic acid amide;
5-(3-Allyl-ureido)-3-pentylsulfanyl-isothiazole-4-carboxylic acid amide;
5-[3-(2-Dimethylamino-ethyl)-ureido]-3-pentylsulfanyl-isothiazole-4-carboxylic acid amide;
3-Hexylsulfanyl-5-(3-isobutyl-ureido)-isothiazole-4-carboxylic acid amide;
3-Hexylsulfanyl-5-(3-propyl-ureido)-isothiazole-4-carboxylic acid amide;
5-(3,3-Dimethyl-ureido)-3-(3-fluoro-benzyloxy)-isothiazole-4-carboxylic acid amide;
3-(3,5-Difluoro-benzyloxy)-5-(3,3-dimethyl-ureido)-isothiazole-4-carboxylic acid amide;
5-(3-Butyl-ureido)-3-heptyloxy-isothiazole-4-carboxylic acid amide;
3-(3-Chloro-benzyloxy)-5-(3,3-dimethyl-ureido)-isothiazole-4-carboxylic acid amide;
5-(3,3-Dimethyl-ureido)-3-(3-iodo-benzyloxy)-isothiazole-4-carboxylic acid amide;
5-(3,3-Dimethyl-ureido)-3-(3-phenoxy-propoxy)-isothiazole-4-carboxylic acid amide;
5-(3,3-Dimethyl-ureido)-3-(4-phenoxy-butoxy)-isothiazole-4-carboxylic acid amide;
5-(3,3-Dimethyl-ureido)-3-(3-m-tolyl-propoxy)-isothiazole-4-carboxylic acid amide;
3-(5-Cyano-pentyloxy)-5-(3,3-dimethyl-ureido)-isothiazole-4-carboxylic acid amide;
5-(3,3-Dimethyl-ureido)-3-methoxy-isothiazole-4-carboxylic acid amide;
3-(5-Chloro-pentyloxy)-5-(3,3-dimethyl-ureido)-isothiazole-4-carboxylic acid amide;
3-(4-Cyano-butoxy)-5-(3,3-dimethyl-ureido)-isothiazole-4-carboxylic acid amide;
5-(3-Furan-2-ylmethyl-ureido)-3-hexylsulfanyl-isothiazole-4-carboxylic acid amide;
5-(3-Butyl-ureido)-3-hexylsulfanyl-isothiazole-4-carboxylic acid amide;
3-Hexylsulfanyl-5-[3-(3-hydroxy-propyl)-ureido]-isothiazole-4-carboxylic acid amide;
3-Pentylsulfanyl-5-[3-(3-pyrrolidin-1-yl-propyl)-ureido]-isothiazole-4-carboxylic acid amide;
3-Hexylsulfanyl-5-[3-(2-hydroxy-ethyl)-ureido]-isothiazole-4-carboxylic acid amide;
3-Benzylsulfanyl-5-(3-methyl-ureido)-isothiazole-4-carboxylic acid amide;
5-{3-[2-(1-Methyl-1H-pyrrol-2-yl)-ethyl]-ureido}-3-pentylsulfanyl-isothiazole-4-carboxylic acid amide;
3-Benzylsulfanyl-5-(3-butyl-ureido)-isothiazole-4-carboxylic acid amide;
Benzoic acid 2-[4-carbamoyl-5-(3,3-dimethyl-ureido)-isothiazol-3-yloxy]-ethyl ester;
5-(3,3-Dimethyl-ureido)-3-(2-phenoxy-ethoxy)-isothiazole-4-carboxylic acid amide;
3-(3-Benzyloxy-propoxy)-5-(3,3-dimethyl-ureido)-isothiazole-4-carboxylic acid amide;
5-(3,3-Dimethyl-ureido)-3-(3,3-diphenyl-propoxy)-isothiazole-4-carboxylic acid amide;
3-(6-Chloro-hexyloxy)-5-(3,3-dimethyl-ureido)-isothiazole-4-carboxylic acid amide;
5-(3,3-Dimethyl-ureido)-3-(2-ethoxy-ethoxy)-isothiazole-4-carboxylic acid amide;
5-(3,3-Dimethyl-ureido)-3-(4-vinyl-benzyloxy)-isothiazole-4-carboxylic acid amide;
3-Cyclohexylmethoxy-5-(3,3-dimethyl-ureido)-isothiazole-4-carboxylic acid amide;
5-(3,3-Dimethyl-ureido)-3-(4-phenyl-butoxy)-isothiazole-4-carboxylic acid amide;
5-(3,3-Dimethyl-ureido)-3-[3-(3-methoxy-phenyl)-propoxy]-isothiazole-4-carboxylic acid amide;
3-(2,5-Dimethyl-benzyloxy)-5-(3,3-dimethyl-ureido)-isothiazole-4-carboxylic acid amide;
3-Hexylsulfanyl-5-{3-[2-(1H-imidazol-4-yl)-ethyl]-ureido}-isothiazole-4-carboxylic acid amide;
3-Hexylsulfanyl-5-[3-(4-hydroxy-butyl)-ureido]-isothiazole-4-carboxylic acid amide;

3-Hexylsulfanyl-5-[3-(2-hydroxy-propyl)-ureido]-isothiazole-4-carboxylic acid amide;
3-Benzylsulfanyl-5-[3-(2-hydroxy-propyl)-ureido]-isothiazole-4-carboxylic acid amide;
3-Benzylsulfanyl-5-(3-benzyl-ureido)-isothiazole-4-carboxylic acid amide;
3-Benzylsulfanyl-5-(3-furan-2-ylmethyl-ureido)-isothiazole-4-carboxylic acid amide;
3-Benzylsulfanyl-5-(3-isobutyl-ureido)-isothiazole-4-carboxylic acid amide;
3-Hexylsulfanyl-5-(3-pentyl-ureido)-isothiazole-4-carboxylic acid amide;
3-Hexylsulfanyl-5-(3-methyl-ureido)-isothiazole-4-carboxylic acid amide;
3-Hexylsulfanyl-5-[3-(3-methyl-butyl)-ureido]-isothiazole-4-carboxylic acid amide;
5-(3-Ethyl-ureido)-3-hexylsulfanyl-isothiazole-4-carboxylic acid amide;
5-[3-(2-Morpholin-4-yl-ethyl)-ureido]-3-pentylsulfanyl-isothiazole-4-carboxylic acid amide;
5-[3-(2,3-Dihydroxy-propyl)-ureido]-3-heptyloxy-isothiazole-4-carboxylic acid amide;
3-Heptyloxy-5-[3-(2-hydroxy-propyl)-ureido]-isothiazole-4-carboxylic acid amide;
5 3-Heptyloxy-5-[3-(2-hydroxy-propyl)-ureido]-isothiazole-4-carboxylic acid amide;
3-Heptyloxy-5-[3-(5-hydroxy-pentyl)-ureido]-isothiazole-4-carboxylic acid amide;
3-Heptyloxy-5-[3-(3-hydroxy-2,2-dimethyl-propyl)-ureido]-isothiazole-4-carboxylic acid amide;
3-Heptyloxy-5-[3-(2-hydroxy-propyl)-ureido]-isothiazole-4-carboxylic acid amide;
3-Heptyloxy-5-[3-(3-hydroxy-propyl)-ureido]-isothiazole-4-carboxylic acid amide;
3-Heptyloxy-5-[3-(2-hydroxy-ethyl)-ureido]-isothiazole-4-carboxylic acid amide;
3-Heptyloxy-5-[3-(4-hydroxy-butyl)-ureido]-isothiazole-4-carboxylic acid amide;
5-(3,3-Dimethyl-ureido)-3-(5-methyl-hexyloxy)-isothiazole-4-carboxylic acid amide;
5-(3,3-Dimethyl-ureido)-3-(naphthalen-1-ylmethoxy)-isothiazole-4-carboxylic acid amide;
5-(3,3-Dimethyl-ureido)-3-(3-phenyl-propoxy)-isothiazole-4-carboxylic acid amide;
5-(3,3-Dimethyl-ureido)-3-(4-methyl-pentyloxy)-isothiazole-4-carboxylic acid amide;
3-(3-Bromo-benzyloxy)-5-(3,3-dimethyl-ureido)-isothiazole-4-carboxylic acid amide;
3-(3,4-Dimethyl-benzyloxy)-5-(3,3-dimethyl-ureido)-isothiazole-4-carboxylic acid amide;
3-(2,4-Dimethyl-benzyloxy)-5-(3,3-dimethyl-ureido)-isothiazole-4-carboxylic acid amide;
3-(3,5-Bis-trifluoromethyl-benzyloxy)-5-(3,3-dimethyl-ureido)-isothiazole-4-carboxylic acid amide;
3-(4-Chloro-benzylsulfanyl)-5-[3-(3-hydroxy-propyl)-ureido]-isothiazole-4-carboxylic acid amide;
3-Benzylsulfanyl-5-[3-(3-hydroxy-propyl)-ureido]-isothiazole-4-carboxylic acid amide;
3-(4-Chloro-benzylsulfanyl)-5-(3-furan-2-ylmethyl-ureido)-isothiazole-4-carboxylic acid amide;
3-(4-Chloro-benzylsulfanyl)-5-[3-(2-hydroxy-propyl)-ureido]-isothiazole-4-carboxylic acid amide;
3-Hexylsulfanyl-5-[3-(2-morpholin-4-yl-ethyl)-ureido]-isothiazole-4-carboxylic acid amide;
3-(4-Chloro-benzylsulfanyl)-5-(3-isobutyl-ureido)-isothiazole-4-carboxylic acid amide;
5-(3-Benzyl-ureido)-3-(4-chloro-benzylsulfanyl)-isothiazole-4-carboxylic acid amide;
3-(4-Chloro-benzylsulfanyl)-5-(3-methyl-ureido)-isothiazole-4-carboxylic acid amide;
5-(3-Butyl-ureido)-3-(4-chloro-benzylsulfanyl)-isothiazole-4-carboxylic acid amide;
5-[3-(2-Dimethylamino-ethyl)-ureido]-3-hexylsulfanyl-isothiazole-4-carboxylic acid amide;
3-Hexylsulfanyl-5-[3-(3-pyrrolidin-1-yl-propyl)-ureido]-isothiazole-4-carboxylic acid amide;
5-[3-(3-Dimethylamino-propyl)-ureido]-3-hexylsulfanyl-isothiazole-4-carboxylic acid amide;
3-Hexylsulfanyl-5-{3-[3-(2-oxo-pyrrolidin-1-yl)-propyl]-ureido}-isothiazole-4-carboxylic acid amide;
3-(4-Chloro-benzylsulfanyl)-5-[3-(2,3-dihydroxy-propyl)-ureido]-isothiazole-4-carboxylic acid amide;
3-(4-Chloro-benzylsulfanyl)-5-[3-(5-hydroxy-pentyl)-ureido]-isothiazole-4-carboxylic acid amide;
3-(4-Chloro-benzylsulfanyl)-5-[3-(4-hydroxy-butyl)-ureido]-isothiazole-4-carboxylic acid amide;
3-(4-Chloro-benzylsulfanyl)-5-[3-(2-hydroxy-butyl)-ureido]-isothiazole-4-carboxylic acid amide;
5-[3-(2,3-Dihydroxy-propyl)-ureido]-3-hexylsulfanyl-isothiazole-4-carboxylic acid amide;
3-Hexylsulfanyl-5-[3-(2-hydroxy-butyl)-ureido]-isothiazole-4-carboxylic acid amide;
3-Benzylsulfanyl-5-[3-(2,3-dihydroxy-propyl)-ureido]-isothiazole-4-carboxylic acid amide;
3-Hexylsulfanyl-5-[3-(5-hydroxy-pentyl)-ureido]-isothiazole-4-carboxylic acid amide;
3-Benzylsulfanyl-5-[3-(2-hydroxy-butyl)-ureido]-isothiazole-4-carboxylic acid amide;
3-(4-Chloro-benzylsulfanyl)-5-[3-(2-hydroxy-ethyl)-ureido]-isothiazole-4-carboxylic acid amide;
3-(4-Chloro-benzylsulfanyl)-5-(3,3-dimethyl-ureido)-isothiazole-4-carboxylic acid amide;
3-Benzylsulfanyl-5-[3-(5-hydroxy-pentyl)-ureido]-isothiazole-4-carboxylic acid amide;
1-(4-Cyano-3-pentylsulfanyl-isothiazol-5-yl)-3-methyl-urea;
5-(3,3-Dimethyl-ureido)-3-(2,4,6-trimethyl-benzyloxy)-isothiazole-4-carboxylic acid amide;
5-(3,3-Dimethyl-ureido)-3-(2-trifluoromethyl-benzyloxy)-isothiazole-4-carboxylic acid amide;
5-(3,3-Dimethyl-ureido)-3-(4-trifluoromethyl-benzyloxy)-isothiazole-4-carboxylic acid amide;
3-(2,4-Dimethyl-benzylsulfanyl)-5-(3,3-dimethyl-ureido)-isothiazole-4-carboxylic acid amide;
5-(3,3-Dimethyl-ureido)-3-(2-fluoro-benzylsulfanyl)-isothiazole-4-carboxylic acid amide;
5-(3,3-Dimethyl-ureido)-3-(3-methyl-benzylsulfanyl)-isothiazole-4-carboxylic acid amide;
5-(3,3-Dimethyl-ureido)-3-(2-fluoro-3-methyl-benzylsulfanyl)-isothiazole-4-carboxylic acid amide;
3-(4-Chloro-benzyloxy)-5-(3,3-dimethyl-ureido)-isothiazole-4-carboxylic acid amide;
3-(2-Chloro-benzylsulfanyl)-5-(3,3-dimethyl-ureido)-isothiazole-4-carboxylic acid amide;
1-Methyl-3-[3-pentylsulfanyl-4-(1H-tetrazol-5-yl)-isothiazol-5-yl]-urea;
5-(3,3-Dimethyl-ureido)-3-(4-fluoro-benzylsulfanyl)-isothiazole-4-carboxylic acid amide;
3-(3-Chloro-benzylsulfanyl)-5-(3,3-dimethyl-ureido)-isothiazole-4-carboxylic acid amide;
3-(2,5-Dimethyl-benzylsulfanyl)-5-(3,3-dimethyl-ureido)-isothiazole-4-carboxylic acid amide;

3-(1-Bromo-naphthalen-2-ylmethylsulfanyl)-5-(3,3-dimethyl-ureido)-isothiazole-4-carboxylic acid amide;
3-(3,4-Dimethyl-benzylsulfanyl)-5-(3,3-dimethyl-ureido)-isothiazole-4-carboxylic acid amide;
3-(Biphenyl-4-ylmethoxy)-5-(3,3-dimethyl-ureido)-isothiazole-4-carboxylic acid amide;
5-(3,3-Dimethyl-ureido)-3-(2-fluoro-benzyloxy)-isothiazole-4-carboxylic acid amide;
3-(2-Chloro-benzyloxy)-5-(3,3-dimethyl-ureido)-isothiazole-4-carboxylic acid amide;
5-(3,3-Dimethyl-ureido)-3-(4-isopropyl-benzyloxy)-isothiazole-4-carboxylic acid amide;
5-(3,3-Dimethyl-ureido)-3-(2,3,4,5,6-pentamethyl-benzyloxy)-isothiazole-4-carboxylic acid amide;
3-(4-Chloro-benzylsulfanyl)-5-[3-(2-dimethylamino-ethyl)-ureido]-isothiazole-4-carboxylic acid amide;
3-(4-Chloro-benzylsulfanyl)-5-[3-(3-dimethylamino-propyl)-ureido]-isothiazole-4-carboxylic acid amide;
3-(4-Chloro-benzylsulfanyl)-5-[3-(3-pyrrolidin-1-yl-propyl)-ureido]-isothiazole-4-carboxylic acid amide;
3-(4-Chloro-benzylsulfanyl)-5-{3-[2-(1H-imidazol-4-yl)-ethyl]-ureido}-isothiazole-4-carboxylic acid amide;
3-(4-Chloro-benzylsulfanyl)-5-{3-[2-(1-methyl-1H-pyrrol-2-yl)-ethyl]-ureido}-isothiazole-4-carboxylic acid amide;
3-(4-Chloro-benzylsulfanyl)-5-[3-(2-morpholin-4-yl-ethyl)-ureido]-isothiazole-4-carboxylic acid amide;
3-(4-Chloro-benzylsulfanyl)-5-{3-[3-(2-oxo-pyrrolidin-1-yl)-propyl]-ureido}-isothiazole-4-carboxylic acid amide;
3-But-2-enyloxy-5-(3,3-dimethyl-ureido)-isothiazole-4-carboxylic acid amide;
5-(3,3-Dimethyl-ureido)-3-(4-methoxy-benzyloxy)-isothiazole-4-carboxylic acid amide;
3-(2,4-Difluoro-benzyloxy)-5-(3,3-dimethyl-ureido)-isothiazole-4-carboxylic acid amide;
5-(3-sec-Butyl-ureido)-3-(4-chloro-benzylsulfanyl)-isothiazole-4-carboxylic acid amide;
3-(4-Chloro-benzylsulfanyl)-5-[3-(2,2-dimethyl-propyl)-ureido]-isothiazole-4-carboxylic acid amide;
3-(4-Chloro-benzylsulfanyl)-5-[3-(1-ethyl-propyl)-ureido]-isothiazole-4-carboxylic acid amide;
3-(4-Chloro-benzylsulfanyl)-5-(3-cyclopropylmethyl-ureido)-isothiazole-4-carboxylic acid amide;
3-(4-Chloro-benzylsulfanyl)-5-[3-(1-methyl-1-phenyl-ethyl)-ureido]-isothiazole-4-carboxylic acid amide;
3-(4-Chloro-benzylsulfanyl)-5-[3-(3,4-difluoro-benzyl)-ureido]-isothiazole-4-carboxylic acid amide;
3-(4-Bromo-2-fluoro-benzyloxy)-5-(3,3-dimethyl-ureido)-isothiazole-4-carboxylic acid amide;
3-(4-tert-Butyl-benzyloxy)-5-(3,3-dimethyl-ureido)-isothiazole-4-carboxylic acid amide;
5-(3-isobutyl-ureido)-3-(4-methyl-benzylsulfanyl)-isothiazole-4-carboxylic acid amide;
5-(3-Butyl-ureido)-3-(4-methyl-benzylsulfanyl)-isothiazole-4-carboxylic acid amide;
5-[3-(3-Hydroxy-propyl)-ureido]-3-(4-methyl-benzylsulfanyl)-isothiazole-4-carboxylic acid amide;
(4-Carbamoyl-3-mercapto-isothiazol-5-yl)-carbamic acid phenyl ester;
5-(3-Butyl-ureido)-3-(3,4-dichloro-benzylsulfanyl)-isothiazole-4-carboxylic acid amide;
3-(3,4-Dichloro-benzylsulfanyl)-5-(3-isobutyl-ureido)-isothiazole-4-carboxylic acid amide;
3-(3,4-Dichloro-benzylsulfanyl)-5-[3-(3-hydroxy-propyl)-ureido]-isothiazole-4-carboxylic acid amide;
4-[4-Carbamoyl-5-(3-isobutyl-ureido)-isothiazol-3-ylsulfanylmethyl]-benzoic acid methyl ester;
4-[5-(3-Butyl-ureido)-4-carbamoyl-isothiazol-3-ylsulfanylmethyl]-benzoic acid methyl ester;
4-{4-Carbamoyl-5-[3-(3-hydroxy-propyl)-ureido]-isothiazol-3-ylsulfanylmethyl}-benzoic acid methyl ester;
3-(3,3-Diphenyl-propylsulfanyl)-5-[3-(3-hydroxy-propyl)-ureido]-isothiazole-4-carboxylic acid amide;
3-(3,3-Diphenyl-propylsulfanyl)-5-(3-isobutyl-ureido)-isothiazole-4-carboxylic acid amide;
5-(3-Butyl-ureido)-3-(3,3-diphenyl-propylsulfanyl)-isothiazole-4-carboxylic acid amide;
5-[3-(2-Dimethylamino-ethyl)-ureido]-3-(3,3-diphenyl-propylsulfanyl)-isothiazole-4-carboxylic acid amide;
3-Hexylsulfanyl-5-[3-(2-methoxy-ethyl)-ureido]-isothiazole-4-carboxylic acid amide;
3-Hexylsulfanyl-5-[3-(2-pyridin-2-yl-ethyl)-ureido]-isothiazole-4-carboxylic acid amide;
3-Hexylsulfanyl-5-[3-(2-pyrrolidin-1-yl-ethyl)-ureido]-isothiazole-4-carboxylic acid amide;
5-(3,3-Dimethyl-ureido)-3-(2-methoxy-benzyloxy)-isothiazole-4-carboxylic acid amide;
3-(2,3-Dichloro-benzyloxy)-5-(3,3-dimethyl-ureido)-isothiazole-4-carboxylic acid amide;
3-Benzylsulfanyl-5-[3-(2-dimethylamino-ethyl)-ureido]-isothiazole-4-carboxylic acid amide;
5-[3-(2-Dimethylamino-ethyl)-ureido]-3-(4-methyl-benzylsulfanyl)-isothiazole-4-carboxylic acid amide;
5-[3-(2-Dimethylamino-ethyl)-ureido]-3-(4-methoxy-benzylsulfanyl)-isothiazole-4-carboxylic acid amide;
5-[3-(2-Dimethylamino-ethyl)-ureido]-3-(3-methoxy-benzylsulfanyl)-isothiazole-4-carboxylic acid amide;
5-[3-(2-Dimethylamino-ethyl)-ureido]-3-(2-methyl-benzylsulfanyl)-isothiazole-4-carboxylic acid amide;
5-[3-(2-Dimethylamino-ethyl)-ureido]-3-(2-methoxy-benzylsulfanyl)-isothiazole-4-carboxylic acid amide;
3-{4-Carbamoyl-5-[3-(2-dimethylamino-ethyl)-ureido]-isothiazol-3-ylsulfanylmethyl}-benzoic acid methyl ester;
3-Benzylsulfanyl-5-[3-(3-pyrrolid in-1-yl-propyl)-ureido]-isothiazole-4-carboxylic acid amide;
3-(4-Methyl-benzylsulfanyl)-5-[3-(3-pyrrolidin-1-yl-propyl)-ureido]-isothiazole-4-carboxylic acid amide;
3-(4-Methoxy-benzylsulfanyl)-5-[3-(3-pyrrolidin-1-yl-propyl)-ureido]-isothiazole-4-carboxylic acid amide;
3-(3-Methoxy-benzylsulfanyl)-5-[3-(3-pyrrolidin-1-yl-propyl)-ureido]-isothiazole-4-carboxylic acid amide;
3-(3-Methoxy-benzylsulfanyl)-5-[3-(3-pyrrolidin-1-yl-propyl)-ureido]-isothiazole-4-carboxylic acid amide;
4-{4-Carbamoyl-5-[3-(3-pyrrolidin-1-yl-propyl)-ureido]-isothiazol-3-ylsulfanylmethyl}-benzoic acid methyl ester;
3-(2-Chloro-benzylsulfanyl)-5-[3-(3-pyrrolidin-1-yl-propyl)-ureido]-isothiazole-4-carboxylic acid amide;
3-(2-Fluoro-benzylsulfanyl)-5-[3-(3-pyrrolidin-1-yl-propyl)-ureido]-isothiazole-4-carboxylic acid amide;
5-(3-Isobutyl-ureido)-3-(2-methyl-benzylsulfanyl)-isothiazole-4-carboxylic acid amide;
5-(3-Isobutyl-ureido)-3-(3-methoxy-benzylsulfanyl)-isothiazole-4-carboxylic acid amide;
5-(3-Isobutyl-ureido)-3-(4-methoxy-benzylsulfanyl)-isothiazole-4-carboxylic acid amide;
5-(3-Isobutyl-ureido)-3-(3-methyl-benzylsulfanyl)-isothiazole-4-carboxylic acid amide;
3-(2-Fluoro-benzylsulfanyl)-5-(3-isobutyl-ureido)-isothiazole-4-carboxylic acid amide;
3-(4-Fluoro-benzylsulfanyl)-5-(3-isobutyl-ureido)-isothiazole-4-carboxylic acid amide;
3-(2-Fluoro-3-methyl-benzylsulfanyl)-5-(3-isobutyl-ureido)-isothiazole-4-carboxylic acid amide;

3-(2,4-Difluoro-benzylsulfanyl)-5-(3-isobutyl-ureido)-isothiazole-4-carboxylic acid amide;
3-(5-Chloro-thiophen-2-ylmethylsulfanyl)-5-(3-isobutyl-ureido)-isothiazole-4-carboxylic acid amide;
3-(Benzo[1,3]dioxol-5-ylmethylsulfanyl)-5-(3-isobutyl-ureido)-isothiazole-4-carboxylic acid amide;
5-(3-Cyclopropylmethyl-ureido)-3-(3,4-dimethyl-benzylsulfanyl)-isothiazole-4-carboxylic acid amide;
3-(3,4-Dimethyl-benzylsulfanyl)-5-(3-isobutyl-ureido)-isothiazole-4-carboxylic acid amide;
3-(4-Bromo-2-fluoro-benzylsulfanyl)-5-(3-isobutyl-ureido)-isothiazole-4-carboxylic acid amide;
3-(2,4-Dimethyl-benzylsulfanyl)-5-(3-isobutyl-ureido)-isothiazole-4-carboxylic acid amide;
3-(3,4-Dimethyl-benzylsulfanyl)-5-[3-(3-pyrrolidin-1-yl-propyl)-ureido]-isothiazole-4-carboxylic acid amide;
3-(4-Bromo-2-fluoro-benzylsulfanyl)-5-[3-(3-pyrrolidin-1-yl-propyl)-ureido]-isothiazole-4-carboxylic acid amide;
5-(3-Cyclopropylmethyl-ureido)-3-(4-methyl-benzylsulfanyl)-isothiazole-4-carboxylic acid amide;
3-(3,4-Dimethyl-benzylsulfanyl)-5-[3-(2-morpholin-4-yl-ethyl)-ureido]-isothiazole-4-carboxylic acid amide;
5-[3-(2,2-Dimethyl-propyl)-ureido]-3-(4-methyl-benzylsulfanyl)-isothiazole-4-carboxylic acid amide;
5-(3-Cyclopropylmethyl-ureido)-3-(3,4-dichloro-benzylsulfanyl)-isothiazole-4-carboxylic acid amide;
5-(3-Cyclopropylmethyl-ureido)-3-(3-methoxy-benzylsulfanyl)-isothiazole-4-carboxylic acid amide;
3-(4-Bromo-2-fluoro-benzylsulfanyl)-5-[3-(3,4-difluoro-benzyl)-ureido]-isothiazole-4-carboxylic acid amide;
5-[3-(3,4-Difluoro-benzyl)-ureido]-3-(3,3-diphenyl-propylsulfanyl)-isothiazole-4-carboxylic acid amide;
5-[3-(3,4-Difluoro-benzyl)-ureido]-3-(4-methoxy-benzylsulfanyl)-isothiazole-4-carboxylic acid amide;
5-[3-(3,4-Difluoro-benzyl)-ureido]-3-(3,4-dimethyl-benzylsulfanyl)-isothiazole-4-carboxylic acid amide;
3-(3-Methyl-benzylsulfanyl)-5-[3-(3-pyrrolidin-1-yl-propyl)-ureido]-isothiazole-4-carboxylic acid amide;
5-[3-(2-Dimethylamino-ethyl)-ureido]-3-(3-methyl-benzylsulfanyl)-isothiazole-4-carboxylic acid amide;
5-[3-(2-Dimethylamino-ethyl)-ureido]-3-(3,4-dimethyl-benzylsulfanyl)-isothiazole-4-carboxylic acid amide;
3-(4-Bromo-2-fluoro-benzylsulfanyl)-5-[3-(3-hydroxy-propyl)-ureido]-isothiazole-4-carboxylic acid amide;
3-{4-Carbamoyl-5-[3-(3,4-difluoro-benzyl)-ureido]-isothiazol-3-ylsulfanylmethyl}-benzoic acid methyl ester;
3-{4-Carbamoyl-5-[3-(3-hydroxy-propyl)-ureido]-isothiazol-3-ylsulfanylmethyl}-benzoic acid methyl ester;
5-[3-(3,4-Difluoro-benzyl)-ureido]-3-phenethylsufanyl-isothiazole-4-carboxylic acid amide;
5-[3-(3,4-Difluoro-benzyl)-ureido]-3-(4-methyl-benzylsulfanyl)-isothiazole-4-carboxylic acid amide;
5-[3-(3,4-Difluoro-benzyl)-ureido]-3-(2,4-dimethyl-benzylsulfanyl)-isothiazole-4-carboxylic acid amide;
3-(4-tert-Butyl-benzylsulfanyl)-5-(3,3-dimethyl-ureido)-isothiazole-4-carboxylic acid amide;
3-(4-Methyl-benzylsulfanyl)-5-[3-(2-phenyl-propyl)-ureido]-isothiazole-4-carboxylic acid amide;
5-[3-(1,2-Dimethyl-propyl)-ureido]-3-(4-methyl-benzylsulfanyl)-isothiazole-4-carboxylic acid amide;
5-[3-(3,5-Difluoro-benzyl)-ureido]-3-(4-methyl-benzylsulfanyl)-isothiazole-4-carboxylic acid amide;
5-{3-[1-(4-Fluoro-phenyl)-ethyl]-ureido}-3-(4-methyl-benzylsulfanyl)-isothiazole-4-carboxylic acid amide;
5-[3-(3-Fluoro-benzyl)-ureido]-3-(4-methyl-benzylsulfanyl)-isothiazole-4-carboxylic acid amide;
5-[3-(4-Fluoro-2-trifluoromethyl-benzyl)-ureido]-3-(4-methyl-benzylsulfanyl)-isothiazole-4-carboxylic acid amide;
5-[3-(3-Chloro-4-fluoro-benzyl)-ureido]-3-(4-methyl-benzylsulfanyl)-isothiazole-4-carboxylic acid amide;
3-(4-Bromo-2-fluoro-benzyloxy)-5-(3-isobutyl-ureido)-isothiazole-4-carboxylic acid amide;
3-(4-Bromo-2-fluoro-benzyloxy)-5-(3-butyl-ureido)-isothiazole-4-carboxylic acid amide;
3-(4-Bromo-2-fluoro-benzyloxy)-5-[3-(2,2-dimethyl-propyl)-ureido]-isothiazole-4-carboxylic acid amide;
3-(4-Bromo-2-fluoro-benzyloxy)-5-(3-furan-2-ylmethyl-ureido)-isothiazole-4-carboxylic acid amide;
5-(3-Allyl-ureido)-3-(4-bromo-2-fluoro-benzyloxy)-isothiazole-4-carboxylic acid amide;
3-(4-Bromo-2-fluoro-benzyloxy)-5-(3-cyclobutyl-ureido)-isothiazole-4-carboxylic acid amide;
3-(4-Bromo-2-fluoro-benzyloxy)-5-[3-(3,3-dimethyl-butyl)-ureido]-isothiazole-4-carboxylic acid amide;
3-(4-Bromo-2-fluoro-benzyloxy)-5-(3-cyclopropylmethyl-ureido)-isothiazole-4-carboxylic acid amide;
3-(4-Bromo-2-fluoro-benzyloxy)-5-[3-(3-phenyl-propyl)-ureido]-isothiazole-4-carboxylic acid amide;
5-[3-(2-Isopropylamino-ethyl)-ureido]-3-(4-methyl-benzyloxy)-isothiazole-4-carboxylic acid amide;
5-(3-Cyclohexylmethyl-ureido)-3-(4-methyl-benzyloxy)-isothiazole-4-carboxylic acid amide;
5-(3-Isobutyl-ureido)-3-(4-methyl-benzyloxy)-isothiazole-4-carboxylic acid amide;
5-[3-(3-Dimethylamino-propyl)-ureido]-3-(4-methyl-benzyloxy)-isothiazole-4-carboxylic acid amide;
3-(5-Chloro-thiophen-2-ylmethylsulfanyl)-5-[3-(3,4-difluoro-benzyl)-ureido]-isothiazole-4-carboxylic acid amide;
3-(5-Chloro-thiophen-2-ylmethylsulfanyl)-5-(3-cyclopropylmethyl-ureido)-isothiazole-4-carboxylic acid amide;
3-(5-Chloro-thiophen-2-ylmethylsulfanyl)-5-[3-(2-morpholin-4-yl-ethyl)-ureido]-isothiazole-4-carboxylic acid amide;
3-(5-Chloro-thiophen-2-ylmethylsulfanyl)-5-[3-(3-pyrrolidin-1-yl-propyl)-ureido]-isothiazole-4-carboxylic acid amide;
5-[3-(3,4-Difluoro-benzyl)-ureido]-3-(5-methyl-thiophen-2-ylmethylsulfanyl)-isothiazole-4-carboxylic acid amide;
3-(5-Chloro-thiophen-2-ylmethoxy)-5-(3-cyclopropylmethyl-ureido)-isothiazole-4-carboxylic acid amide;
5-(3-Isobutyl-ureido)-3-(5-methyl-thiophen-2-ylmethylsulfanyl)-isothiazole-4-carboxylic acid amide;
3-(5-Chloro-thiophen-2-ylmethoxy)-5-[3-(3,4-difluoro-benzyl)-ureido]-isothiazole-4-carboxylic acid amide;
5-(3-Cyclopropylmethyl-ureido)-3-(5-methyl-thiophen-2-ylmethylsulfanyl)-isothiazole-4-carboxylic acid amide;
3-(5-Methyl-thiophen-2-ylmethylsulfanyl)-5-[3-(2-morpholin-4-yl-ethyl)-ureido]-isothiazole-4-carboxylic acid amide;
3-(5-Methyl-thiophen-2-ylmethylsulfanyl)-5-[3-(3-pyrrolidin-1-yl-propyl)-ureido]-isothiazole-4-carboxylic acid amide;
3-(4-Chloro-benzyloxy)-5-[3-(3-hydroxy-propyl)-ureido]-isothiazole-4-carboxylic acid amide
3-(4-Bromo-2-fluoro-benzyloxy)-5-[3-(3,4-difluoro-benzyl)-ureido]-isothiazole-4-carboxylic acid amide;
3-(4-Bromo-2-fluoro-benzyloxy)-5-[3-(2-dimethylamino-ethyl)-ureido]-isothiazole-4-carboxylic acid amide;
3-(4-Bromo-2-fluoro-benzyloxy)-5-[3-(3-dimethylamino-propyl)-ureido]-isothiazole-4-carboxylic acid amide;

3-(4-Chloro-2-fluoro-benzyloxy)-5-(3-furan-2-ylmethyl-ureido)-isothiazole-4-carboxylic acid amide;

3-(4-Chloro-2-fluoro-benzyloxy)-5-[3-(2-morpholin-4-yl-ethyl)-ureido]-isothiazole-4-carboxylic acid amide;

3-(2,3-Dichloro-benzyloxy)-5-[3-(2-morpholin-4-yl-ethyl)-ureido]-isothiazole-4-carboxylic acid amide;

3-(2,3-Dichloro-benzyloxy)-5-[3-(3-morpholin-4-yl-propyl)-ureido]-isothiazole-4-carboxylic acid amide;

3-(2,3-Dichloro-benzyloxy)-5-[3-(3-hydroxy-propyl)-ureido]-isothiazole-4-carboxylic acid amide;

3-(2,3-Dichloro-benzyloxy)-5-[3-(2-pyrrolidin-1-yl-ethyl)-ureido]-isothiazole-4-carboxylic acid amide;

3-(2,3-Dichloro-benzyloxy)-5-[3-(3-pyrrolidin-1-yl-propyl)-ureido]-isothiazole-4-carboxylic acid amide;

3-(2,3-Dichloro-benzyloxy)-5-{3-[2-(1H-imidazol-4-yl)-ethyl]-ureido}-isothiazole-4-carboxylic acid amide;

3-(2,3-Dichloro-benzyloxy)-5-[3-(1-ethyl-pyrrolidin-2-ylmethyl)-ureido]-isothiazole-4-carboxylic acid amide;

3-(2,3-Dichloro-benzyloxy)-5-[3-(2-isopropylamino-ethyl)-ureido]-isothiazole-4-carboxylic acid amide;

3-(2,3-Dichloro-benzyloxy)-5-[3-(3-diethylamino-2-hydroxy-propyl)-ureido]-isothiazole-4-carboxylic acid amide;

3-(4-Chloro-2-fluoro-benzyloxy)-5-[3-(3-morpholin-4-yl-propyl)-ureido]-isothiazole-4-carboxylic acid amide;

3-(4-Chloro-2-fluoro-benzyloxy)-5-[3-(2-pyrrolidin-1-yl-ethyl)-ureido]-isothiazole-4-carboxylic acid amide;

3-(4-Chloro-2-fluoro-benzyloxy)-5-[3-(3-pyrrolidin-1-yl-propyl)-ureido]-isothiazole-4-carboxylic acid amide;

3-(4-Chloro-2-fluoro-benzyloxy)-5-[3-(3-imidazol-1-yl-propyl)-ureido]-isothiazole-4-carboxylic acid amide;

3-(4-Chloro-2-fluoro-benzyloxy)-5-[3-(3-hydroxy-propyl)-ureido]-isothiazole-4-carboxylic acid amide;

3-(4-Chloro-2-fluoro-benzyloxy)-5-[3-(3,4-difluoro-benzyl)-ureido]-isothiazole-4-carboxylic acid amide;

3-(4-Chloro-2-fluoro-benzyloxy)-5-[3-(2-hydroxy-propyl)-ureido]-isothiazole-4-carboxylic acid amide;

5-(3-Cyclopropylmethyl-ureido)-3-(2,3-dichloro-benzyloxy)-isothiazole-4-carboxylic acid amide;

3-(4-Bromo-2-fluoro-benzyloxy)-5-[3-(3-isopropylamino-propyl)-ureido]-isothiazole-4-carboxylic acid amide;

3-(4-Bromo-2-fluoro-benzyloxy)-5-[3-(2-sec-butylamino-ethyl)-ureido]-isothiazole-4-carboxylic acid amide;

3-(4-Bromo-2-fluoro-benzyloxy)-5-[3-(2-hydroxy-propyl)-ureido]-isothiazole-4-carboxylic acid amide;

3-(4-Bromo-2-fluoro-benzyloxy)-5-[3-(2-hydroxy-propyl)-ureido]-isothiazole-4-carboxylic acid amide;

3-(2,3-Difluoro-benzyloxy)-5-[3-(2-morpholin-4-yl-ethyl)-ureido]-isothiazole-4-carboxylic acid amide;

3-(2,3-Difluoro-benzyloxy)-5-[3-(3-morpholin-4-yl-propyl)-ureido]-isothiazole-4-carboxylic acid amide;

3-(2,3-Difluoro-benzyloxy)-5-(3-isobutyl-ureido)-isothiazole-4-carboxylic acid amide;

3-(2,3-Difluoro-benzyloxy)-5-[3-(2-pyrrolidin-1-yl-ethyl)-ureido]-isothiazole-4-carboxylic acid amide;

3-(2,3-Difluoro-benzyloxy)-5-[3-(3-pyrrolidin-1-yl-propyl)-ureido]-isothiazole-4-carboxylic acid amide;

3-(2-Fluoro-3-methyl-benzyloxy)-5-[3-(2-morpholin-4-yl-ethyl)-ureido]-isothiazole-4-carboxylic acid amide;

3-(2-Fluoro-3-methyl-benzyloxy)-5-(3-isobutyl-ureido)-isothiazole-4-carboxylic acid amide;

3-(2-Fluoro-benzyloxy)-5-[3-(2-hydroxy-propyl)-ureido]-isothiazole-4-carboxylic acid amide;

3-(2-Fluoro-benzyloxy)-5-[3-(2-hydroxy-propyl)-ureido]-isothiazole-4-carboxylic acid amide;

5-[3-(2-Dimethylamino-propyl)-ureido]-3-(2-fluoro-3-methyl-benzyloxy)-isothiazole-4-carboxylic acid amide;

3-(2-Fluoro-3-methyl-benzyloxy)-5-[3-(2-pyrrolidin-1-yl-ethyl)-ureido]-isothiazole-4-carboxylic acid amide;

3-(2-Fluoro-3-methyl-benzyloxy)-5-[3-(3-pyrrolidin-1-yl-propyl)-ureido]-isothiazole-4-carboxylic acid amide;

3-(2,3-Difluoro-benzyloxy)-5-[3-(2-dimethylamino-propyl)-ureido]-isothiazole-4-carboxylic acid amide;

3-(2-Fluoro-3-methyl-benzyloxy)-5-[3-(3-morpholin-4-yl-propyl)-ureido]-isothiazole-4-carboxylic acid amide;

3-(4-Bromo-2-fluoro-benzyloxy)-5-[3-(5-methyl-furan-2-ylmethyl)-ureido]-isothiazole-4-carboxylic acid amide;

3-(3-Fluoro-2,4-dimethyl-benzyloxy)-5-(3-isobutyl-ureido)-isothiazole-4-carboxylic acid amide;

3-(4-Chloro-2-fluoro-benzyloxy)-5-[3-(3-hydroxy-2-methyl-propyl)-ureido]-isothiazole-4-carboxylic acid amide;

3-(4-Chloro-2-fluoro-benzyloxy)-5-[3-(2-methyl-3-morpholin-4-yl-propyl)-ureido]-isothiazole-4-carboxylic acid amide;

3-(2,3-Dichloro-benzyloxy)-5-[3-(3-hydroxy-2-methyl-propyl)-ureido]-isothiazole-4-carboxylic acid amide;

3-(2,3-Dichloro-benzyloxy)-5-[3-(2-methyl-3-morpholin-4-yl-propyl)-ureido]-isothiazole-4-carboxylic acid amide;

3-(3-Fluoro-4-methyl-benzyloxy)-5-[3-(3-hydroxy-2-methyl-propyl)-ureido]-isothiazole-4-carboxylic acid amide;

3-(3-Fluoro-4-methyl-benzyloxy)-5-[3-(2-methyl-3-morpholin-4-yl-propyl)-ureido]-isothiazole-4-carboxylic acid amide;

3-(3,4-Dichloro-benzyloxy)-5-[3-(3-hydroxy-2-methyl-propyl)-ureido]-isothiazole-4-carboxylic acid amide;

3-(3,4-Dichloro-benzyloxy)-5-[3-(2-methyl-3-morpholin-4-yl-propyl)-ureido]-isothiazole-4-carboxylic acid amide;

3-(2,3-Dichloro-benzyloxy)-5-[3-(3-imidazol-1-yl-propyl)-ureido]-isothiazole-4-carboxylic acid amide;

3-(2,3-Difluoro-benzyloxy)-5-[3-(3-imidazol-1-yl-propyl)-ureido]-isothiazole-4-carboxylic acid amide;

3-(3-Fluoro-4-methyl-benzyloxy)-5-[3-(3-imidazol-1-yl-propyl)-ureido]-isothiazole-4-carboxylic acid amide;

3-(4-Chloro-benzyloxy)-5-[3-(2-morpholin-4-yl-ethyl)-ureido]-isothiazole-4-carboxylic acid amide;

3-(4-Chloro-benzyloxy)-5-[3-(3-morpholin-4-yl-propyl)-ureido]-isothiazole-4-carboxylic acid amide;

3-(4-Chloro-benzyloxy)-5-[3-(3-imidazol-1-yl-propyl)-ureido]-isothiazole-4-carboxylic acid amide;

3-(2,5-Difluoro-benzyloxy)-5-[3-(3-hydroxy-2-methyl-propyl)-ureido]-isothiazole-4-carboxylic acid amide;

3-(2,5-Difluoro-benzyloxy)-5-[3-(2-morpholin-4-yl-ethyl)-ureido]-isothiazole-4-carboxylic acid amide;

3-(2,5-Difluoro-benzyloxy)-5-[3-(3-imidazol-1-yl-propyl)-ureido]-isothiazole-4-carboxylic acid amide;

3-(2,5-Difluoro-benzyloxy)-5-[3-(2-methyl-3-morpholin-4-yl-propyl)-ureido]-isothiazole-4-carboxylic acid amide;

3-(4-Bromo-2-fluoro-benzyloxy)-5-[3-(2-isopropylamino-ethyl)-ureido]-isothiazole-4-carboxylic acid amide;

3-(3-Fluoro-2,4-dimethyl-benzyloxy)-5-[3-(2-isopropylamino-ethyl)-ureido]-isothiazole-4-carboxylic acid amide;

3-(3-Fluoro-2,4-dimethyl-benzyloxy)-5-[3-(3-isopropylamino-propyl)-ureido]-isothiazole-4-carboxylic acid amide;

5-[3-(2-sec-Butylamino-ethyl)-ureido]-3-(3-fluoro-2,4-dimethyl-benzyloxy)-isothiazole-4-carboxylic acid amide;

3-(3-Fluoro-2,4-dimethyl-benzyloxy)-5-[3-(2-hydroxy-propyl)-ureido]-isothiazole-4-carboxylic acid amide;

3-(3-Fluoro-2,4-dimethyl-benzyloxy)-5-[3-(2-hydroxy-propyl)-ureido]-isothiazole-4-carboxylic acid amide;

5-[3-(2-sec-Butylamino-ethyl)-ureido]-3-(2-fluoro-4-methyl-benzyloxy)-isothiazole-4-carboxylic acid amide;

3-(2-Fluoro-4-methyl-benzyloxy)-5-[3-(3-isopropy-lamino-propyl)-ureido]-isothiazole-4-carboxylic acid amide;
3-(2-Fluoro-4-methyl-benzyloxy)-5-[3-(2-isopropy-lamino-ethyl)-ureido]-isothiazole-4-carboxylic acid amide;
3-(2-Fluoro-4-methyl-benzyloxy)-5-[3-(2-hydroxy-pro-pyl)-ureido]-isothiazole-4-carboxylic acid amide;
3-(2-Fluoro-4-methyl-benzyloxy)-5-[3-(3-imidazol-1-yl-propyl)-ureido]-isothiazole-4-carboxylic acid amide;
3-(2,4-Dimethyl-benzyloxy)-5-[3-(3-imidazol-1-yl-pro-pyl)-ureido]-isothiazole-4-carboxylic acid amide;
5-[3-(3-Imidazol-1-yl-propyl)-ureido]-3-(4-methyl-ben-zyloxy)-isothiazole-4-carboxylic acid amide;
3-(2-Fluoro-benzyloxy)-5-[3-(3-imidazol-1-yl-propyl)-ureido]-isothiazole-4-carboxylic acid amide;
3-(2-Fluoro-4-methyl-benzyloxy)-5-[3-(2-hydroxy-pro-pyl)-ureido]-isothiazole-4-carboxylic acid amide;
5-[3-(3,3-Dimethyl-butyl)-ureido]-3-(2-fluoro-4-methyl-benzyloxy)-isothiazole-4-carboxylic acid amide;
5-(3-Cyclopropylmethyl-ureido)-3-(2-fluoro-4-methyl-benzyloxy)-isothiazole-4-carboxylic acid amide;
5-[3-(2,2-Dimethyl-propyl)-ureido]-3-(2-fluoro-4-me-thyl-benzyloxy)-isothiazole-4-carboxylic acid amide;
3-(3-Fluoro-2,4-dimethyl-benzyloxy)-5-[3-(3-imidazol-1-yl-propyl)-ureido]-isothiazole-4-carboxylic acid amide;
3-(2-Fluoro-4,6-dimethyl-benzyloxy)-5-[3-(3-imidazol-1-yl-propyl)-ureido]-isothiazole-4-carboxylic acid amide;
3-(4-Chloro-2-fluoro-benzyloxy)-5-{3-[2-(1H-imidazol-4-yl)-ethyl]-ureido}-isothiazole-4-carboxylic acid amide;
3-(2,3-Dichloro-benzyloxy)-5-[3-(3-imidazol-1-yl-2-me-thyl-propyl)-ureido]-isothiazole-4-carboxylic acid amide;
3-(2,3-Dichloro-benzyloxy)-5-[3-(2-methyl-3-pyrrolidin-1-yl-propyl)-ureido]-isothiazole-4-carboxylic acid amide;
3-(4-Chloro-2-fluoro-benzyloxy)-5-[3-(2-hydroxy-3-morpholin-4-yl-propyl)-ureido]-isothiazole-4-carboxylic acid amide;
3-(4-Chloro-2-fluoro-benzyloxy)-5-[3-(3-imidazol-1-yl-2-methyl-propyl)-ureido]-isothiazole-4-carboxylic acid amide;
3-(2,3-Dichloro-benzyloxy)-5-[3-(2-methyl-3-piperidin-1-yl-propyl)-ureido]-isothiazole-4-carboxylic acid amide;
3-(2,3-Dichloro-benzyloxy)-5-[3-(2-hydroxy-3-morpho-lin-4-yl-propyl)-ureido]-isothiazole-4-carboxylic acid amide;
3-(5-Chloro-thiophen-2-ylmethoxy)-5-[3-(3-morpholin-4-yl-propyl)-ureido]-isothiazole-4-carboxylic acid amide;
3-(5-Chloro-thiophen-2-ylmethoxy)-5-[3-(3-imidazol-1-yl-propyl)-ureido]-isothiazole-4-carboxylic acid amide;
3-(5-Chloro-thiophen-2-ylmethoxy)-5-(3-furan-2-ylm-ethyl-ureido)-isothiazole-4-carboxylic acid amide;
3-(5-Chloro-thiophen-2-ylmethoxy)-5-[3-(3-hydroxy-2-methyl-propyl)-ureido]-isothiazole-4-carboxylic acid amide;
3-(4-Bromo-2-fluoro-benzyloxy)-5-[3-(3-imidazol-1-yl-propyl)-ureido]-isothiazole-4-carboxylic acid amide;
3-(2-Fluoro-4-methyl-benzyloxy)-5-[3-(3-morpholin-4-yl-propyl)-ureido]-isothiazole-4-carboxylic acid amide;
3-(2,4-Dimethyl-benzyloxy)-5-[3-(3-morpholin-4-yl-pro-pyl)-ureido]-isothiazole-4-carboxylic acid amide;
3-(4-Methyl-benzyloxy)-5-[3-(3-morpholin-4-yl-propyl)-ureido]-isothiazole-4-carboxylic acid amide;
3-(2-Fluoro-benzyloxy)-5-[3-(3-morpholin-4-yl-propyl)-ureido]-isothiazole-4-carboxylic acid amide;
3-(2,3-Difluoro-4-methyl-benzyloxy)-5-[3-(3-imidazol-1-yl-propyl)-ureido]-isothiazole-4-carboxylic acid amide;
3-(2,3-Difluoro-4-methyl-benzyloxy)-5-[3-(3-morpholin-4-yl-propyl)-ureido]-isothiazole-4-carboxylic acid amide;

3-(2,3-Difluoro-4-methyl-benzyloxy)-5-[3-(2-hydroxy-3-morpholin-4-yl-propyl)-ureido]-isothiazole-4-carboxylic acid amide;
3-(2,3-Difluoro-4-methyl-benzyloxy)-5-[3-(3-imidazol-1-yl-2-methyl-propyl)-ureido]-isothiazole-4-carboxylic acid amide;
3-(2,3-Difluoro-4-methyl-benzyloxy)-5-[3-(2-methyl-3-morpholin-4-yl-propyl)-ureido]-isothiazole-4-carboxylic acid amide;
3-(2,3-Difluoro-4-methyl-benzyloxy)-5-[3-(3-hydroxy-2-methyl-propyl)-ureido]-isothiazole-4-carboxylic acid amide;
3-(2,3-Difluoro-4-methyl-benzyloxy)-5-[3-(2-hydroxy-propyl)-ureido]-isothiazole-4-carboxylic acid amide;
3-(2,3-Difluoro-4-methyl-benzyloxy)-5-(3-furan-2-ylm-ethyl-ureido)-isothiazole-4-carboxylic acid amide;
3-(2,3-Difluoro-4-methyl-benzyloxy)-5-{3-[3-(2,6-dim-ethyl-morpholin-4-yl)-2-methyl-propyl]-ureido}-isothiaz-ole-4-carboxylic acid amide;
3-(2,3-Difluoro-4-methyl-benzyloxy)-5-{3-[2-(3H-imi-dazol-4-yl)-ethyl]-ureido}-isothiazole-4-carboxylic acid amide;
3-(2,3-Difluoro-4-methyl-benzyloxy)-5-[3-(3-hydroxy-propyl)-ureido]-isothiazole-4-carboxylic acid amide;
3-(4-Chloro-2-fluoro-benzyloxy)-5-[3-(3-isopropy-lamino-propyl)-ureido]-isothiazole-4-carboxylic acid amide;
3-(2,3-Dichloro-benzyloxy)-5-[3-(2-hydroxy-propyl)-ureido]-isothiazole-4-carboxylic acid amide;
3-(5-Chloro-thiophen-2-ylmethoxy)-5-[3-(2-hydroxy-propyl)-ureido]-isothiazole-4-carboxylic acid amide;
3-(2-Fluoro-4-methyl-benzyloxy)-5-[3-(3-phenyl-pro-pyl)-ureido]-isothiazole-4-carboxylic acid amide;
5-(3-Cyclobutyl-ureido)-3-(2-fluoro-4-methyl-benzy-loxy)-isothiazole-4-carboxylic acid amide;
5-[3-(2,3-Difluoro-benzyl)-ureido]-3-(2-fluoro-4-methyl-benzyloxy)-isothiazole-4-carboxylic acid amide;
3-(2-Fluoro-4-methyl-benzyloxy)-5-(3-isobutyl-ureido)-isothiazole-4-carboxylic acid amide;
5-(3-Allyl-ureido)-3-(2-fluoro-4-methyl-benzyloxy)-isothiazole-4-carboxylic acid amide;
3-(4-Bromo-2-fluoro-benzyloxy)-5-[3-(3-morpholin-4-yl-propyl)-ureido]-isothiazole-4-carboxylic acid amide;
3-(3-Fluoro-2,4-dimethyl-benzyloxy)-5-[3-(3-morpholin-4-yl-propyl)-ureido]-isothiazole-4-carboxylic acid amide;
3-(2-Fluoro-4,6-dimethyl-benzyloxy)-5-[3-(3-morpholin-4-yl-propyl)-ureido]-isothiazole-4-carboxylic acid amide;
3-(2-Fluoro-4,6-dimethyl-benzyloxy)-5-[3-(2-methyl-3-morpholin-4-yl-propyl)-ureido]-isothiazole-4-carboxylic acid amide;
5-{3-[3-(2,6-Dimethyl-morpholin-4-yl)-2-methyl-pro-pyl]-ureido}-3-(2-fluoro-4,6-dimethyl-benzyloxy)-isothiaz-ole-4-carboxylic acid amide;
3-(2-Fluoro-4,6-dimethyl-benzyloxy)-5-[3-(2-hydroxy-3-morpholin-4-yl-propyl)-ureido]-isothiazole-4-carboxylic acid amide;
3-(2-Fluoro-4,6-dimethyl-benzyloxy)-5-[3-(3-imidazol-1-yl-2-methyl-propyl)-ureido]-isothiazole-4-carboxylic acid amide;
3-(2-Fluoro-4,6-dimethyl-benzyloxy)-5-{3-[2-(1H-imi-dazol-4-yl)-ethyl]-ureido}-isothiazole-4-carboxylic acid amide;
3-(2-Fluoro-4,6-dimethyl-benzyloxy)-5-[3-(3-isopropy-lamino-propyl)-ureido]-isothiazole-4-carboxylic acid amide;
3-(2-Fluoro-4,6-dimethyl-benzyloxy)-5-[3-(3-hydroxy-propyl)-ureido]-isothiazole-4-carboxylic acid amide;
3-(4-Bromo-2-fluoro-benzyloxy)-5-[3-(4-morpholin-4-yl-butyl)-ureido]-isothiazole-4-carboxylic acid amide;

3-(4-Chloro-2-fluoro-benzyloxy)-5-[3-(4-morpholin-4-yl-butyl)-ureido]-isothiazole-4-carboxylic acid amide;

3-(4-Chloro-2-fluoro-benzyloxy)-5-(3-morpholin-2-ylmethyl-ureido)-isothiazole-4-carboxylic acid amide;

3-(2,3-Dichloro-benzyloxy)-5-(3-morpholin-2-ylmethyl-ureido)-isothiazole-4-carboxylic acid amide;

2-Aminomethyl-morpholine-4-carboxylic acid [4-carbamoyl-3-(2, 3-dichloro-benzyloxy)-isothiazol-5-yl]-amide;

3-(2-Fluoro-4-methyl-benzyloxy)-5-13-(2-morpholin-4-yl-ethyl)-ureido]-isothiazole-4-carboxylic acid amide;

3-(2-Fluoro-4-methyl-benzyloxy)-5-[3-(2-methyl-3-morpholin-4-yl-propyl)-ureido]-isothiazole-4-carboxylic acid amide;

5-{3-[3-(2,6-Dimethyl-morpholin-4-yl)-2-methyl-propyl]-ureido}-3-(2-fluoro-4-methyl-benzyloxy)-isothiazole-4-carboxylic acid amide;

3-(2-Fluoro-4-methyl-benzyloxy)-5-[3-(2-hydroxy-3-morpholin-4-yl-propyl)-ureido]-isothiazole-4-carboxylic acid amide;

3-(2-Fluoro-4-methyl-benzyloxy)-5-[3-(4-morpholin-4-yl-butyl)-ureido]-isothiazole-4-carboxylic acid amide;

3-(2,4-Dimethyl-benzyloxy)-5-[3-(2-hydroxy-3-morpholin-4-yl-propyl)-ureido]-isothiazole-4-carboxylic acid amide;

3-(2,4-Dimethyl-benzyloxy)-5-[3-(2-methyl-3-morpholin-4-yl-propyl)-ureido]-isothiazole-4-carboxylic acid amide;

3-(2,4-Dimethyl-benzyloxy)-5-[3-(2-morpholin-4-yl-ethyl)-ureido]-isothiazole-4-carboxylic acid amide;

3-(2,4-Dimethyl-benzyloxy)-5-[3-(4-morpholin-4-yl-butyl)-ureido]-isothiazole-4-carboxylic acid amide;

3-(4-Bromo-2-fluoro-benzyloxy)-5-[3-(2-methyl-allyl)-ureido]-isothiazole-4-carboxylic acid amide;

3-(4-Bromo-2-fluoro-benzyloxy)-5-[3-(3-cyclohexylamino-propyl)-ureido]-isothiazole-4-carboxylic acid amide;

3-(4-Bromo-2-fluoro-benzyloxy)-5-[3-(4-dimethylamino-butyl)-ureido]-isothiazole-4-carboxylic acid amide;

3-(4-Bromo-2-fluoro-benzyloxy)-5-[3-(3-dimethylamino-2,2-dimethyl-propyl)-ureido]-isothiazole-4-carboxylic acid amide;

3-(2,5-Difluoro-4-methyl-benzyloxy)-5-[3-(3-imidazol-1-yl-propyl)-ureido]-isothiazole-4-carboxylic acid amide;

3-(2,5-Difluoro-4-methyl-benzyloxy)-5-[3-(3-morpholin-4-yl-propyl)-ureido]-isothiazole-4-carboxylic acid amide;

3-(2,5-Difluoro-4-methyl-benzyloxy)-5-[3-(2-hydroxy-3-morpholin-4-yl-propyl)-ureido]-isothiazole-4-carboxylic acid amide;

3-(2,5-Difluoro-4-methyl-benzyloxy)-5-[3-(3-imidazol-1-yl-2-methyl-propyl)-ureido]-isothiazole-4-carboxylic acid amide;

3-(2,5-Difluoro-4-methyl-benzyloxy)-5-[3-(3-hydroxy-2-methyl-propyl)-ureido]-isothiazole-4-carboxylic acid amide;

3-(2,5-Difluoro-4-methyl-benzyloxy)-5-[3-(2-hydroxy-propyl)-ureido]-isothiazole-4-carboxylic acid amide;

3-(2,5-Difluoro-4-methyl-benzyloxy)-5-(3-furan-2-ylmethyl-ureido)-isothiazole-4-carboxylic acid amide;

3-(2,5-Difluoro-4-methyl-benzyloxy)-5-{3-[2-(1H-imidazol-4-yl)-ethyl]-ureido}-isothiazole-4-carboxylic acid amide;

3-(2,5-Difluoro-4-methyl-benzyloxy)-5-[3-(3-hydroxy-propyl)-ureido]-isothiazole-4-carboxylic acid amide;

3-(2,5-Difluoro-4-methyl-benzyloxy)-5-[3-(3-isopropylamino-propyl)-ureido]-isothiazole-4-carboxylic acid amide;

5-(3-{3-[Bis-(2-hydroxy-ethyl)-amino]-propyl}-ureido)-3-(4-bromo-2-fluoro-benzyloxy)-isothiazole-4-carboxylic acid amide;

3-(4-Bromo-2-fluoro-benzyloxy)-5-[3-(3-diethylamino-2-hydroxy-propyl)-ureido]-isothiazole-4-carboxylic acid amide;

3-(4-Bromo-2-fluoro-benzyloxy)-5-[3-(3-hydroxy-propyl)-ureido]-isothiazole-4-carboxylic acid amide;

3-(4-Bromo-2-fluoro-benzyloxy)-5-[3-(2-hydroxy-3,3-dimethyl-butyl)-ureido]-isothiazole-4-carboxylic acid amide;

3-(4-Bromo-2-fluoro-benzyloxy)-5-[3-(2,3-dihydroxy-propyl)-ureido]-isothiazole-4-carboxylic acid amide;

3-(4-Bromo-2-fluoro-benzyloxy)-5-[3-(3-hydroxy-2-methyl-propyl)-ureido]-isothiazole-4-carboxylic acid amide;

3-(2,3-Difluoro-4-methyl-benzyloxy)-5-[3-(4-morpholin-4-yl-butyl)-ureido]-isothiazole-4-carboxylic acid amide;

3-(2,3-Difluoro-4-methyl-benzyloxy)-5-3-[2-(-methyl-pyrrolidin-2-yl)-ethyl]-ureido}-isothiazole-4-carboxylic acid amide;

3-(2,3-Difluoro-4-methyl-benzyloxy)-5-{3-[3-(2-oxo-pyrrolidin-1-yl)-propyl]-ureido}-isothiazole-4-carboxylic acid amide;

3-(2,3-Difluoro-4-methyl-benzyloxy)-5-[3-(2-hydroxy-butyl)-ureido]-isothiazole-4-carboxylic acid amide;

5-(3-Cyclopropylmethyl-ureido)-3-(2,3-difluoro-4-methyl-benzyloxy)-isothiazole-4-carboxylic acid amide;

3-(2,3-Difluoro-4-methyl-benzyloxy)-5-(3-[3-(4-methyl-piperazin-yl)-propyl]-ureido}-isothiazole-4-carboxylic acid amide;

3-(2,5-Difluoro-4-methyl-benzyloxy)-5-[3-(2-methyl-3-morpholin-4-yl-propyl)-ureido]-isothiazole-4-carboxylic acid amide;

3-(2,4-Dimethyl-benzyloxy)-5-{3-[3-(2,6-dimethyl-morpholin-4-yl)-2-methyl-propyl]-ureido}-isothiazole-4-carboxylic acid amide;

5-[3-(3-Cyclohexylamino-propyl)-ureido]-3-(2-fluoro-4-methyl-benzyloxy)-isothiazole-4-carboxylic acid amide;

3-(2-Fluoro-4-methyl-benzyloxy)-5-{3-[3-(4-methyl-piperazin-1-yl)-propyl]-ureido}-isothiazole-4-carboxylic acid amide;

3-(2-Fluoro-4-methyl-benzyloxy)-5-{3-[2-(1H-imidazol-4-yl)-ethyl]-ureido}-isothiazole-4-carboxylic acid amide;

3-(2-Fluoro-4-methyl-benzyloxy)-5-[3-(2-methyl-allyl)-ureido]-isothiazole-4-carboxylic acid amide;

3-(4-Bromo-2-fluoro-benzyloxy)-5-[3-(3-imidazol-1-yl-2-methyl-propyl)-ureido]-isothiazole-4-carboxylic acid amide;

3-(4-Bromo-2-fluoro-benzyloxy)-5-{3-[3-(2,6-dimethyl-morpholin-4-yl)-2-methyl-propyl]-ureido}-isothiazole-4-carboxylic acid amide 5-(3-Allyl-ureido)-3-(2-fluoro-4,6-dimethyl-benzyloxy)-isothiazole-4-carboxylic acid amide;

3-(4-Bromo-2-fluoro-benzyloxy)-5-{3-[3-(2-methyl-piperidin-1-yl)-propyl]-ureido}-isothiazole-4-carboxylic acid amide;

3-(4-Bromo-2-fluoro-benzyloxy)-5-[3-(2-methyl-3-piperidin-1-yl-propyl)-ureido]-isothiazole-4-carboxylic acid amide;

3-(4-Bromo-2-fluoro-benzyloxy)-5-[3-(2-methyl-3-pyrrolidin-1-yl-propyl)-ureido]-isothiazole-4-carboxylic acid amide;

3-(4-Bromo-2-fluoro-benzyloxy)-5-[3-(4-pyrrolidin-1-yl-butyl)-ureido]-isothiazole-4-carboxylic acid amide;

3-(4-Bromo-2-fluoro-benzyloxy)-5-[3-(3-pyrrolidin-1-yl-propyl)-ureido]-isothiazole-4-carboxylic acid amide;

3-(4-Bromo-2-fluoro-benzyloxy)-5-{3-[3-(4-methyl-piperazin-1-yl)-propyl]-ureido}-isothiazole-4-carboxylic acid amide;

3-(2,5-Difluoro-4-methyl-benzyloxy)-5-[3-(4-morpholin-4-yl-butyl)-ureido]-isothiazole-4-carboxylic acid amide;

3-(2,3-Difluoro-4-methyl-benzyloxy)-5-[3-(2-morpholin-4-yl-ethyl)-ureido]-isothiazole-4-carboxylic acid amide;

3-(2,3-Difluoro-4-methyl-benzyloxy)-5-{3-[2-(1-methyl-1H-pyrrol-2-yl)-ethyl]-isothiazole-4-carboxylic acid amide;

3-(2,3-Difluoro-4-methyl-benzyloxy)-5-[3-(2,3-dihydroxy-propyl)-ureido]-isothiazole-4-carboxylic acid amide;

3-(2,3-Difluoro-4-methyl-benzyloxy)-5-(3-isobutyl-ureido)-isothiazole-4-carboxylic acid amide;

5-(3-Allyl-ureido)-3-(2,3-difluoro-4-methyl-benzyloxy)-isothiazole-4-carboxylic acid amide;

5-(3-Cyclohexylmethyl-ureido)-3-(2,3-difluoro-4-methyl-benzyloxy)-isothiazole-4-carboxylic acid amide;

3-(2,3-Difluoro-4-methyl-benzyloxy)-5-[3-(2-piperidin-1-yl-ethyl)-ureido]-isothiazole-4-carboxylic acid amide;

3-(2,3-Difluoro-4-methyl-benzyloxy)-5-[3-(2-methyl-3-piperidin-1-yl-propyl)-ureido]-isothiazole-4-carboxylic acid amide;

3-(2,5-Difluoro-4-methyl-benzyloxy)-5-13-[3-(2,6-dimethyl-morpholin-4-yl)-2-methyl-propyl]-ureido}-isothiazole-4-carboxylic acid amide;

3-(5-Chloro-thiophen-2-ylmethoxy)-5-[3-(3-isopropylamino-propyl)-ureido]-isothiazole-4-carboxylic acid amide;

3-(2-Fluoro-4-methyl-benzyloxy)-5-{3-[2-(3-methyl-3H-imidazol-4-yl)-ethyl]-ureido}-isothiazole-4-carboxylic acid amide;

3-(2-Fluoro-4-methyl-benzyloxy)-5-[3-(2-pyrrolidin-1-yl-ethyl)-ureido]-isothiazole-4-carboxylic acid amide;

3-(2-Fluoro-4-methyl-benzyloxy)-5-[3-(2-methyl-3-pyrrolidin-1-yl-propyl)-ureido]-isothiazole-4-carboxylic acid amide;

5-[3-(1-Benzyl-pyrrolidin-3-yl)-ureido]-3-(2-fluoro-4-methyl-benzyloxy)-isothiazole-4-carboxylic acid amide;

5-[3-(1-Ethyl-pyrrolidin-2-ylmethyl)-ureido]-3-(2-fluoro-4-methyl-benzyloxy)-isothiazole-4-carboxylic acid amide;

3-(2-Fluoro-4-methyl-benzyloxy)-5-[3-(3-hydroxy-propyl)-ureido]-isothiazole-4-carboxylic acid amide;

5-[3-(3-Dimethylamino-2,2-dimethyl-propyl)-ureido]-3-(2-fluoro-4-methyl-benzyloxy)-isothiazole-4-carboxylic acid amide;

3-(2-Fluoro-4-methyl-benzyloxy)-5-[3-(2-methyl-3-piperidin-1-yl-propyl)-ureido]-isothiazole-4-carboxylic acid amide;

3-(2-Fluoro-4-methyl-benzyloxy)-5-{3-[2-(1-methyl-pyrrolidin-2-yl)-ethyl]-ureido}-isothiazole-4-carboxylic acid amide;

3-(2-Fluoro-4-methyl-benzyloxy)-5-[3-(3-pyrrolidin-1-yl-propyl)-ureido]-isothiazole-4-carboxylic acid amide;

3-(2-Fluoro-4-methyl-benzyloxy)-5-[3-(4-pyrrolidin-1-yl-butyl)-ureido]-isothiazole-4-carboxylic acid amide;

3-(2-Fluoro-4-methyl-benzyloxy)-5-[3-(3-methyl-butyl)-ureido]-isothiazole-4-carboxylic acid amide;

3-(2,3-Difluoro-4-methyl-benzyloxy)-5-(3-morpholin-2-ylmethyl-ureido)-isothiazole-4-carboxylic acid amide;

2-Aminomethyl-morpholine-4-carboxylic acid [4-carbamoyl-3-(2,3-difluoro-4-methyl-benzyloxy)-isothiazol-5-yl]-amide;

3-(2,3-Dichloro-benzyloxy)-5-[3-(3-isopropylamino-propyl)-ureido]-isothiazole-4-carboxylic acid amide;

3-(2,3-Difluoro-4-methyl-benzyloxy)-5-(3-isopropylamino-propyl)-ureido]-isothiazole-4-carboxylic acid amide;

5-[3-(3-Cyclohexylamino-propyl)-ureido]-3-(2,3-difluoro-4-methyl-benzyloxy)-isothiazole-4-carboxylic acid amide;

3-(2,3-Difluoro-4-iodo-benzyloxy)-5-[3-(3-imidazol-1-yl-propyl)-ureido]-isothiazole-4-carboxylic acid amide;

3-(2-Fluoro-4-methyl-benzyloxy)-5-[3-(3-imidazol-1-yl-2-methyl-propyl)-ureido]-isothiazole-4-carboxylic acid amide;

3-(2-Fluoro-4-methyl-benzyloxy)-5-(3-furan-2-ylmethyl-ureido)-isothiazole-4-carboxylic acid amide;

5-(3-{3-[Bis-(2-hydroxy-ethyl)-amino]-propyl}-ureido)-3-(2-fluoro-4-methyl-benzyloxy)-isothiazole-4-carboxylic acid amide;

5-[3-(3-Diethylamino-2-hydroxy-propyl)-ureido]-3-(2-fluoro-4-methyl-benzyloxy)-isothiazole-4-carboxylic acid amide;

3-(4-Bromo-2-fluoro-benzyloxy)-5-{3-[3-(2-oxo-pyrrolidin-1-yl)-propyl]-ureido}-isothiazole-4-carboxylic acid amide;

3-(4-Bromo-2-fluoro-benzyloxy)-5-[3-(2-hydroxy-butyl)-ureido]-isothiazole-4-carboxylic acid amide;

3-(4-Bromo-2-fluoro-benzyloxy)-5-(3-methyl-ureido)-isothiazole-4-carboxylic acid amide;

5-[3-(2-Dimethylamino-ethyl)-ureido]-3-(2-fluoro-4-methyl-benzyloxy)-isothiazole-4-carboxylic acid amide;

5-[3-(3-Dimethylamino-propyl)-ureido]-3-(2-fluoro-4-methyl-benzyloxy)-isothiazole-4-carboxylic acid amide;

3-(4-Bromo-2-fluoro-benzyloxy)-5-(3-ethyl-ureido)-isothiazole-4-carboxylic acid amide;

3-(2-Fluoro-4-methyl-benzyloxy)-5-(3-methyl-ureido)-isothiazole-4-carboxylic acid amide;

3-(4-Bromo-2-fluoro-benzyloxy)-5-(3-propyl-ureido)-isothiazole-4-carboxylic acid amide;

3-(2-Fluoro-4-methyl-benzyloxy)-5-[3-(3-hydroxy-2-methyl-propyl)-ureido]-isothiazole-4-carboxylic acid amide;

3-(2-Fluoro-4-methyl-benzyloxy)-5-[3-(2-hydroxy-butyl)-ureido]-isothiazole-4-carboxylic acid amide;

3-(2-Fluoro-4-methyl-benzyloxy)-5-{3-[2-(1-methyl-1H-pyrrol-2-yl)-ethyl]-ureido}-isothiazole-4-carboxylic acid amide;

3-(4-Ethyl-2,3-difluoro-benzyloxy)-5-[3-(3-imidazol-1-yl-propyl)-ureido]-isothiazole-4-carboxylic acid amide;

3-(4-Ethyl-2,3-difluoro-benzyloxy)-5-[3-(3-hydroxy-propyl)-ureido]-isothiazole-4-carboxylic acid amide;

3-(4-Ethyl-2,3-difluoro-benzyloxy)-5-[3-(3-hydroxy-2-methyl-propyl)-ureido]-isothiazole-4-carboxylic acid amide;

3-(4-Ethyl-2,3-difluoro-benzyloxy)-5-[3-(3-morpholin-4-yl-propyl)-ureido]-isothiazole-4-carboxylic acid amide;

3-(4-Ethyl-2,3-difluoro-benzyloxy)-5-[3-(4-morpholin-4-yl-butyl)-ureido]-isothiazole-4-carboxylic acid amide;

3-(4-Ethyl-2,3-difluoro-benzyloxy)-5-[3-(3-imidazol-1-yl-2-methyl-propyl)-ureido]-isothiazole-4-carboxylic acid amide;

3-(4-Ethyl-2,3-difluoro-benzyloxy)-5-{3-[2-(1H-imidazol-4-yl)-ethyl]-ureido}-isothiazole-4-carboxylic acid amide;

3-(4-Ethyl-2,3-difluoro-benzyloxy)-5-{3-[3-(4-methyl-piperazin-1-yl)-propyl]-ureido}-isothiazole-4-carboxylic acid amide;

3-(4-Ethyl-2,3-difluoro-benzyloxy)-5-(3-furan-2-ylmethyl-ureido)-isothiazole-4-carboxylic acid amide;

3-(4-Ethyl-2,3-difluoro-benzyloxy)-5-[3-(3-isopropylamino-propyl)-ureido]-isothiazole-4-carboxylic acid amide;

5-{3-[3-(2,6-Dimethyl-morpholin-4-yl)-2-methyl-propyl]-ureido}-3-(4-ethyl-2,3-difluoro-benzyloxy)-isothiazole-4-carboxylic acid amide;

3-(4-Ethyl-2,3-difluoro-benzyloxy)-5-[3-(2-hydroxy-propyl)-ureido]-isothiazole-4-carboxylic acid amide;

5-[3-(4-Dimethylamino-butyl)-ureido]-3-(2-fluoro-4-methyl-benzyloxy)-isothiazole-4-carboxylic acid amide;

3-(4-Bromo-2-fluoro-benzyloxy)-5-[3-(3-dibutylamino-propyl)-ureido]-isothiazole-4-carboxylic acid amide;

3-(4-Bromo-2-fluoro-benzyloxy)-5-[3-(3-diethylamino-propyl)-ureido]-isothiazole-4-carboxylic acid amide;

3-(4-Bromo-2-fluoro-benzyloxy)-5-[3-(6-dimethylamino-hexyl)-ureido]-isothiazole-4-carboxylic acid amide;

3-(2-Fluoro-4-methyl-benzyloxy)-5-{3-[3-(2-methyl-piperidin-1-yl)-propyl]-ureido}-isothiazole-4-carboxylic acid amide;

5-[3-(3-Dibutylamino-propyl)-ureido]-3-(2-fluoro-4-methyl-benzyloxy)-isothiazole-4-carboxylic acid amide;

3-(2,5-Difluoro-4-methyl-benzyloxy)-5-(3-isobutyl-ureido)-isothiazole-4-carboxylic acid amide;

5-(3-Cyclopropylmethyl-ureido)-3-(2,5-difluoro-4-methyl-benzyloxy)-isothiazole-4-carboxylic acid amide;

3-(2,5-Difluoro-4-methyl-benzyloxy)-5-{3-[2-(1-methyl-1H-pyrrol-2-yl)-ethyl]-isothiazole-4-carboxylic acid amide;

5-[3-(3-Cyclohexylamino-propyl)-ureido]-3-(2,5-difluoro-4-methyl-benzyloxy)-isothiazole-4-carboxylic acid amide;

3-(2,5-Difluoro-4-methyl-benzyloxy)-5-[3-(4-pyrrolidin-1-yl-butyl)-ureido]-isothiazole-4-carboxylic acid amide;

3-(2,5-Difluoro-4-methyl-benzyloxy)-5-{3-[2-(1-methyl-pyrrolidin-2-yl)-ethyl]-ureido}-isothiazole-4-carboxylic acid amide;

3-(2,5-Difluoro-4-methyl-benzyloxy)-5-[3-(2,3-dihydroxy-propyl)-ureido]-isothiazole-4-carboxylic acid amide;

3-(2,5-Difluoro-4-methyl-benzyloxy)-5-(3-morpholin-2-ylmethyl-ureido)-isothiazole-4-carboxylic acid amide;

2-Aminomethyl-morpholine-4-carboxylic acid [4-carbamoyl-3-(2,5-difluoro-4-methyl-benzyloxy)-isothiazol-5-yl]-amide;

5-(3-Allyl-ureido)-3-(2,5-difluoro-4-methyl-benzyloxy)-isothiazole-4-carboxylic acid amide;

3-(2,5-Difluoro-4-methyl-benzyloxy)-5-[3-(tetrahydro-furan-2-ylmethyl)-ureido]-isothiazole-4-carboxylic acid amide;

3-(2,5-Difluoro-4-methyl-benzyloxy)-5-(3-[3-(4-methyl-piperazin-1-yl)-propyl]-ureido}-isothiazole-4-carboxylic acid amide;

5-[3-(3-Cyclohexylamino-propyl)-ureido]-3-(4-ethyl-2,3-difluoro-benzyloxy)-isothiazole-4-carboxylic acid amide;

3-(4-Ethyl-2,3-difluoro-benzyloxy)-5-(3-isobutyl-ureido)-isothiazole-4-carboxylic acid amide;

5-(3-Cyclopropylmethyl-ureido)-3-(4-ethyl-2,3-difluoro-benzyloxy)-isothiazole-4-carboxylic acid amide;

3-(4-Ethyl-2,3-difluoro-benzyloxy)-5-[3-(4-pyrrolidin-1-yl-butyl)-ureido]-isothiazole-4-carboxylic acid amide;

5-(3-Allyl-ureido)-3-(4-ethyl-2,3-difluoro-benzyloxy)-isothiazole-4-carboxylic acid amide;

5-[3-(3-Diethylamino-propyl)-ureido]-3-(2-fluoro-4-methyl-benzyloxy)-isothiazole-4-carboxylic acid amide;

5-[3-(6-Dimethylamino-hexyl)-ureido]-3-(2-fluoro-4-methyl-benzyloxy)-isothiazole-4-carboxylic acid amide;

3-(2,6-Difluoro-4-methyl-benzyloxy)-5-[3-(3-imidazol-1-yl-propyl)-ureido]-isothiazole-4-carboxylic acid amide;

3-(2,6-Difluoro-4-methyl-benzyloxy)-5-[3-(2-morpholin-4-yl-ethyl)-ureido]-isothiazole-4-carboxylic acid amide;

3-(2-Fluoro-4-methoxy-benzyloxy)-5-[3-(3-imidazol-1-yl-propyl)-ureido]-isothiazole-4-carboxylic acid amide;

3-(2-Fluoro-4-methoxy-benzyloxy)-5-[3-(2-morpholin-4-yl-ethyl)-ureido]-isothiazole-4-carboxylic acid amide;

3-(2-Fluoro-4-methoxy-benzyloxy)-5-[3-(3-morpholin-4-yl-propyl)-ureido]-isothiazole-4-carboxylic acid amide;

3-(2-Fluoro-4-methoxy-benzyloxy)-5-[3-(4-morpholin-4-yl-butyl)-ureido]-isothiazole-4-carboxylic acid amide;

5-(3-{3-[Bis-(2-hydroxy-ethyl)-amino]-propyl}-ureido)-3-(2-fluoro-4-methoxy-benzyloxy)-isothiazole-4-carboxylic acid amide;

3-(2-Fluoro-4-methoxy-benzyloxy)-5-{3-[3-(4-methyl-piperazin-1-yl)-propyl]-ureido}-isothiazole-4-carboxylic acid amide;

5-[3-(3-Dimethylamino-propyl)-ureido]-3-(2-fluoro-4-methoxy-benzyloxy)-isothiazole-4-carboxylic acid amide;

5-[3-(4-Dimethylamino-butyl)-ureido]-3-(2-fluoro-4-methoxy-benzyloxy)-isothiazole-4-carboxylic acid amide;

3-(2-Fluoro-4-methoxy-benzyloxy)-5-[3-(3-isopropylamino-propyl)-ureido]-isothiazole-4-carboxylic acid amide;

5-[3-(3-Cyclohexylamino-propyl)-ureido]-3-(2-fluoro-4-methoxy-benzyloxy)-isothiazole-4-carboxylic acid amide;

3-(4-Ethyl-2,5-difluoro-benzyloxy)-5-[3-(3-imidazol-1-yl-propyl)-ureido]-isothiazole-4carboxylic acid amide;

3-(2-Fluoro-4-methoxy-benzyloxy)-5-[3-(3-hydroxy-propyl)-ureido]-isothiazole-4-carboxylic acid amide;

3-(4-Ethyl-2,5-difluoro-benzyloxy)-5-[3-(4-morpholin-4-yl-butyl)-ureido]-isothiazole-4-carboxylic acid amide;

3-(4-Ethyl-2,5-difluoro-benzyloxy)-5-[3-(3-imidazol-1-yl-2-methyl-propyl)-ureido]-isothiazole-4-carboxylic acid amide;

3-(4-Ethyl-2,5-difluoro-benzyloxy)-5-[3-(3-hydroxy-2-methyl-pr opyl)-ureido]-isothiazole-4-carboxylic acid amide;

3-(4-Ethyl-2,5-difluoro-benzyloxy)-5-[3-(3-morpholin-4-yl-propyl)-ureido]-isothiazole-4-carboxylic acid amide;

3-(4-Ethyl-2,5-difluoro-benzyloxy)-5-[3-(2-hydroxy-propyl)-ureido]-isothiazole-4-carboxylic acid amide;

3-(4-Ethyl-2,5-difluoro-benzyloxy)-5-(3-furan-2-ylmethyl-ureido)-isothiazole-4-carboxylic acid amide;

3-(4-Ethyl-2,5-difluoro-benzyloxy)-5-{3-[2-(3H-imidazol-4-yl)-ethyl]-ureido}-isothiazole-4-carboxylic acid amide;

3-(4-Ethyl-2,5-difluoro-benzyloxy)-5-[3-(3-hydroxy-propyl)-ureido]-isothiazole-4-carboxylic acid amide;

3-(4-Ethyl-2,5-difluoro-benzyloxy)-5-[3-(4-pyrrolidin-1-yl-butyl)-ureido]-isothiazole-4-carboxylic acid amide;

3-(4-Ethyl-2,5-difluoro-benzyloxy)-5-(3-isobutyl-ureido)-isothiazole-4-carboxylic acid amide;

5-[3-(2,3-Dihydroxy-propyl)-ureido]-3-(4-ethyl-2,3-difluoro-benzyloxy)-isothiazole-4-carboxylic acid amide;

3-(2-Fluoro-4-methyl-benzyloxy)-5-(3-morpholin-2-ylmethyl-ureido)-isothiazole-4-carboxylic acid amide;

2-Aminomethyl-morpholine-4-carboxylic acid [4-carbamoyl-3-(2-fluoro-4-methyl-benzyloxy)-isothiazol-5-yl]-amide;

3-(2-Fluoro-4-methyl-benzyloxy)-5-(3-{3-[4-(2-hydroxy-ethyl)-piperazin-1-yl]-propyl}-ureido)-isothiazole-4-carboxylic acid amide;

3-(2-Fluoro-4-methyl-benzyloxy)-5-{3-[3-(2-oxo-pyrrolidin-1-yl)-propyl]-ureido}-isothiazole-4-carboxylic acid amide;

5-[3-(3-Diethylamino-2-hydroxy-propyl)-ureido]-3-(2,5-difluoro-4-methyl-benzyloxy)-isothiazole-4-carboxylic acid amide;

3-(2,5-Difluoro-4-methyl-benzyloxy)-5-[3-(2-morpholin-4-yl-ethyl)-ureido]-isothiazole-4-carboxylic acid amide;

5-(3-{3-[Bis-(2-hydroxy-ethyl)-amino]-propyl}-ureido)-3-(2,5-difluoro-4-methyl-benzyloxy)-isothiazole-4-carboxylic acid amide;

3-(4-Chloro-2,5-difluoro-benzyloxy)-5-[3-(3-imidazol-1-yl-propyl)-ureido]-isothiazole-4-carboxylic acid amide;

3-(4-Chloro-2,5-difluoro-benzyloxy)-5-{3-[3-(4-methyl-piperazin-1-yl)-propyl]-ureido}-isothiazole-4-carboxylic acid amide;

3-(4-Chloro-2,5-difluoro-benzyloxy)-5-[3-(2-morpholin-4-yl-ethyl)-ureido]-isothiazole-4-carboxylic acid amide;

3-(4-Chloro-2,5-difluoro-benzyloxy)-5-[3-(4-morpholin-4-yl-butyl)-ureido]-isothiazole-4-carboxylic acid amide;

3-(4-Chloro-2,5-difluoro-benzyloxy)-5-[3-(4-pyrrolidin-1-yl-butyl)-ureido]-isothiazole-4-carboxylic acid amide;

3-(4-Chloro-2,5-difluoro-benzyloxy)-5-(3-cyclopropylmethyl-ureido)-isothiazole-4-carboxylic acid amide;

3-(4-Chloro-2,5-difluoro-benzyloxy)-5-[3-(3-hydroxy-propyl)-ureido]-isothiazole-4-carboxylic acid amide;

5-[3-(6-Dimethylamino-hexyl)-ureido]-3-(2-fluoro-4,6-dimethyl-benzyloxy)-isothiazole-4-carboxylic acid amide;

5-[3-(4-Dimethylamino-butyl)-ureido]-3-(2-fluoro-4,6-dimethyl-benzyloxy)-isothiazole-4-carboxylic acid amide;

3-(2-Fluoro-4,6-dimethyl-benzyloxy)-5-(3-{3-[4-(2-hydroxy-ethyl)-piperazin-1-yl-propyl}-ureido)-isothiazole-4-carboxylic acid amide;

5-[3-(3-tert-Butylamino-propyl)-ureido]-3-(2-fluoro-4,6-dimethyl-benzyloxy)-isothiazole-4-carboxylic acid amide;

5-[3-(6-Dimethylamino-hexyl)-ureido]-3-(2,4,6-trifluoro-benzyloxy)-isothiazole-4-carboxylic acid amide;

3-(4-Ethyl-2,5-difluoro-benzyloxy)-5-[3-(3-isopropylamino-propyl)-ureido]-isothiazole-4-carboxylic acid amide;

5-[3-(3-Cyclohexylamino-propyl)-ureido]-3-(4-ethyl-2,5-difluoro-benzyloxy)-isothiazole-4-carboxylic acid amide;

3-(2-Chloro-4-methyl-benzyloxy)-5-[3-(4-morpholin-4-yl-butyl)-ureido]-isothiazole-4-carboxylic acid amide;

3-(2-Chloro-4-methyl-benzyloxy)-5-[3-(6-dimethylamino-hexyl)-ureido]-isothiazole-4-carboxylic acid amide;

3-(2-Chloro-4-methyl-benzyloxy)-5-[3-(3-imidazol-1-yl-propyl)-ureido]-isothiazole-4-carboxylic acid amide;

3-(2-Chloro-4-methyl-benzyloxy)-5-[3-(2-morpholin-4-yl-ethyl)-ureido]-isothiazole-4-carboxylic acid amide;

3-(2-Chloro-4-methyl-benzyloxy)-5-{3-[3-(4-methyl-piperazin-1-yl)-propyl]-ureido}-isothiazole-4-carboxylic acid amide;

5-[3-(3-Imidazol-1-yl-propyl)-ureido]-3-(2,4,6-trifluoro-benzyloxy)-isothiazole-4-carboxylic acid amide;

5-[3-(4-Dimethylamino-butyl)-ureido]-3-(2,4,6-trifluoro-benzyloxy)-isothiazole-4-carboxylic acid amide;

5-[3-(4-tert-Butylamino-3-hydroxy-butyl)-ureido]-3-(2-fluoro-4,6-dimethyl-benzyloxy)-isothiazole-4-carboxylic acid amide;

3-(2,5-Difluoro-4-methyl-benzyloxy)-5-(3-{4-[4-(;

3-(2,5-Difluoro-4-methyl-benzyloxy)-5-{3-[4-(4-methyl-piperazin-1-yl)-butyl]-ureido}-isothiazole-4-carboxylic acid amide;

3-(2,5-Difluoro-4-methyl-benzyloxy)-5-(3-{4-[4-(3-hydroxy-propyl)-piperazin-1-yl]-butyl}-ureido)-isothiazole-4-carboxylic acid amide;

3-(2,5-Difluoro-4-methyl-benzyloxy)-5-(3-{3-[4-(2-hydroxy-ethyl)-piperazin-1-yl]-propyl}-ureido)-isothiazole-4-carboxylic acid amide;

5-[3-(3-tert-Butylamino-propyl)-ureido]-3-(2-fluoro-4-methyl-benzyloxy)-isothiazole-4-carboxylic acid amide;

3-(2,5-Difluoro-4-methyl-benzyloxy)-5-[3-(6-dimethylamino-hexyl)-ureido]-isothiazole-4-carboxylic acid amide;

3-(2,4-Difluoro-benzyloxy)-5-[3-(3-imidazol-1-yl-propyl)-ureido]-isothiazole-4-carboxylic acid amide;

3-(2,4-Difluoro-benzyloxy)-5-{3-[3-(4-methyl-piperazin-1-yl)-propyl]-ureido}-isothiazole-4-carboxylic acid amide;

3-(2,4-Difluoro-benzyloxy)-5-[3-(3-isopropylamino-propyl)-ureido]-isothiazole-4-carboxylic acid amide;

3-(2,4-Difluoro-benzyloxy)-5-[3-(4-pyrrolidin-1-yl-butyl)-ureido]-isothiazole-4-carboxylic acid amide;

3-(2-Fluoro-4-trifluoromethyl-benzyloxy)-5-[3-(2-morpholin-4-yl-ethyl)-ureido]-isothiazole-4-carboxylic acid amide;

3-(2,4-Difluoro-benzyloxy)-5-[3-(6-dimethylamino-hexyl)-ureido]-isothiazole-4-carboxylic acid amide;

3-(2,4-Difluoro-benzyloxy)-5-[3-(3-hydroxy-propyl)-ureido]-isothiazole-4-carboxylic acid amide;

3-(2,5-Dichloro-benzyloxy)-5-[3-(3-imidazol-1-yl-propyl)-ureido]-isothiazole-4-carboxylic acid amide;

3-(2,5-Dichloro-benzyloxy)-5-[3-(3-isopropylamino-propyl)-ureido]-isothiazole-4-carboxylic acid amide;

3-(2,5-Dichloro-benzyloxy)-5-[3-(4-pyrrolidin-1-yl-butyl)-ureido]-isothiazole-4-carboxylic acid amide;

3-(2,5-Dichloro-benzyloxy)-5-{3-[3-(4-methyl-piperazin-1-yl)-propyl]-ureido}-isothiazole-4-carboxylic acid amide;

3-(2,5-Dichloro-benzyloxy)-5-[3-(6-dimethylamino-hexyl)-ureido]-isothiazole-4-carboxylic acid amide;

3-(2,5-Dichloro-benzyloxy)-5-[3-(3-hydroxy-propyl)-ureido]-isothiazole-4-carboxylic acid amide;

3-(2,5-Difluoro-4-methyl-benzyloxy)-5-[3-(5-isopropylamino-pentyl)-ureido]-isothiazole-4-carboxylic acid amide;

5-(3-{3-[Bis-(2-hydroxy-ethyl)-amino]-propyl}-ureido)-3-(4-chloro-2,5-difluoro-benzyloxy)-isothiazole-4-carboxylic acid amide;

3-(4-Chloro-2,5-difluoro-benzyloxy)-5-{3-[4-(4-methyl-piperazin-1-yl)-butyl]-ureido}-isothiazole-4-carboxylic acid amide;

3-(4-Chloro-2,5-difluoro-benzyloxy)-5-(3-{3-[4-(2-hydroxy-ethyl)-piperazin-1-yl]-propyl}-ureido)-isothiazole-4-carboxylic acid amide;

5-{3-[4-(4-Benzyl-piperazin-1-yl)-butyl]-ureido}-3-(4-chloro-2,5-difluoro-benzyloxy-isothiazole-4-carboxylic acid amide;

3-(4-Chloro-2,5-difluoro-benzyloxy)-5-[3-(6-dimethylamino-hexyl)-ureido]-isothiazole-4-carboxylic acid amide;

3-(4-Chloro-2,5-difluoro-benzyloxy)-5-[3-(3-isopropylamino-propyl)-ureido]-isothiazole-4-carboxylic acid amide;

5-[3-(2-Azepan-1-yl-ethyl)-ureido]-3-(2,5-difluoro-4-methyl-benzyloxy)-isothiazole-4-carboxylic acid amide;

5-[3-(1-Aza-bicyclo[2.2.2]oct-4-ylmethyl)-ureido]-3-(2,5-difluoro-4-methyl-benzyloxy)-isothiazole-4-carboxylic acid amide;

5-[3-(4-tert-Butylamino-3-hydroxy-butyl)-ureido]-3-(2,5-difluoro-4-methyl-benzyloxy)-isothiazole-4-carboxylic acid amide;

3-(2,5-Difluoro-4-methyl-benzyloxy)-5-[3-(4-hydroxy-1-methyl-pyrrolidin-2-ylmethyl)-ureido]-isothiazole-4-carboxylic acid amide;

3-(4-Chloro-2,5-difluoro-benzyloxy)-5-[3-(3-diethylamino-2-hydroxy-propyl)-ureido]-isothiazole-4-carboxylic acid amide;

3-(4-Chloro-2,5-difluoro-benzyloxy)-5-[3-(5-isopropylamino-pentyl)-ureido]-isothiazole-4-carboxylic acid amide;

3-(4-Chloro-2,5-difluoro-benzyloxy)-5-(3-{4-[4-(2-hydroxy-ethyl)-piperazin-1-yl]-butyl}-ureido)-isothiazole-4-carboxylic acid amide;

3-(4-Chloro-2,5-difluoro-benzyloxy)-5-[3-(3-hydroxy-2-methyl-propyl)-ureido]-isothiazole-4-carboxylic acid amide;

2-Aminomethyl-morpholine-4-carboxylic acid [4-carbamoyl-3-(4-chloro-2,5-difluoro-benzyloxy)-isothiazol-5-yl]-amide;

3-(4-Chloro-2,5-difluoro-benzyloxy)-5-(3-morpholin-2-ylmethyl-ureido)-isothiazole-4-carboxylic acid amide;

3-(4-Chloro-2,5-difluoro-benzyloxy)-5-{3-[2-(1-methyl-pyrrolidin-2-yl)-ethyl]-ureido}-isothiazole-4-carboxylic acid amide;

3-(4-Chloro-2,5-difluoro-benzyloxy)-5-(3-{4-[4-(3-hydroxy-propyl)-piperazin-1-yl]-butyl}-ureido)-isothiazole-4-carboxylic acid amide;

3-(2-Fluoro-4-methyl-benzyloxy)-5-[3-(5-isopropylamino-pentyl)-ureido]-isothiazole-4-carboxylic acid amide;

3-(3-Fluoro-2,4-dimethyl-benzyloxy)-5-[3-(2-morpholin-4-y-ethyl)-ureido]-isothiazole-4-carboxylic acid amide;

5-(3-{4-[Bis-(2-hydroxy-ethyl)-amino]-butyl}-ureido)-3-(2,5-difluoro-4-methyl-benzyloxy)-isothiazole-4-carboxylic acid amide;

3-(2,5-Difluoro-4-methyl-benzyloxy)-5-[3-(5-morpholin-4-yl-pentyl)-ureido]-isothiazole-4-carboxylic acid amide;

3-(2,5-Difluoro-4-methyl-benzyloxy)-5-{3-[5-(4-methyl-piperazin-1-yl)-pentyl]-ureido}-isothiazole-4-carboxylic acid amide;

3-(2,5-Difluoro-4-methyl-benzyloxy)-5-(3-{5-[4-(2-hydroxy-ethyl)-piperazin-1-yl]-pentyl}-ureido)-isothiazole-4-carboxylic acid amide;

3-(2,5-Difluoro-4-methyl-benzyloxy)-5-{3-[7-(4-methyl-piperazin-1-yl)-heptyl]-ureido}-isothiazole-4-carboxylic acid amide;

3-(2,5-Difluoro-4-methyl-benzyloxy)-5-{3-[6-(4-methyl-piperazin-1-yl)-hexyl]-ureido}-isothiazole-4-carboxylic acid amide;

3-(2,5-Difluoro-4-methyl-benzyloxy)-5-(3-{6-[4-(2-hydroxy-ethyl)-piperazin-1-yl]-hexyl}-ureido)-isothiazole-4-carboxylic acid amide;

3-(2,5-Difluoro-4-methyl-benzyloxy)-5-(3-{7-[4-(2-hydroxy-ethyl)-piperazin-1-yl]-heptyl}-ureido)-isothiazole-4-carboxylic acid amide;

3-(2,5-Dichloro-4-methyl-benzyloxy)-5-{3-[4-(4-methyl-piperazin-1-yl)-butyl]-ureido}-isothiazole-4-carboxylic acid amide;

3-(2,5-Dichloro-4-methyl-benzyloxy)-5-[3-(6-dimethylamino-hexyl)-ureido]-isothiazole-4-carboxylic acid amide;

3-(2,5-Dichloro-4-methyl-benzyloxy)-5-[3-(4-pyrrolidin-1-yl-butyl)-ureido]-isothiazole-4-carboxylic acid amide;

3-(2,5-Difluoro-4-methyl-benzyloxy)-5-{3-[4-(5-methyl-2,5-diaza-bicyclo[2.2.1]hept-2-yl)-butyl]-ureido}-isothiazole-4-carboxylic acid amide;

3-(2,5-Difluoro-4-methyl-benzyloxy)-5-[3-(octahydro-pyrido[1,2-a]pyrazin-7-ylmethyl)-ureido]-isothiazole-4-carboxylic acid amide;

3-(2-Fluoro-4-methyl-benzyloxy)-5-{3-[7-(4-methyl-piperazin-1-yl)-heptyl]-ureido}-isothiazole-4-carboxylic acid amide;

3-(2-Fluoro-4-methyl-benzyloxy)-5-{3-[6-(4-methyl-piperazin-1-yl)-hexyl]-ureido}-isothiazole-4-carboxylic acid amide;

3-(2-Fluoro-4-methyl-benzyloxy)-5-(3-{7-[4-(2-hydroxy-ethyl)-piperazin-1-yl]-heptyl}-ureido)-isothiazole-4-carboxylic acid amide;

3-(2-Fluoro-4-methyl-benzyloxy)-5-(3-{6-[4-(2-hydroxy-ethyl)-piperazin-1-yl]-hexyl}-ureido)-isothiazole-4-carboxylic acid amide;

3-(2-Fluoro-4-methyl-benzyloxy)-5-(3-{5-[4-(2-hydroxy-ethyl)-piperazin-1-yl]-pentyl}-ureido)-isothiazole-4-carboxylic acid amide;

3-(2-Fluoro-4-methyl-benzyloxy)-5-{3-[5-(4-methyl-piperazin-1-yl)-pentyl]-ureido}-isothiazole-4-carboxylic acid amide;

3-(4-Chloro-2,5-difluoro-benzyloxy)-5-{3-[5-(4-methyl-piperazin-1-yl)-pentyl]-ureido}-isothiazole-4-carboxylic acid amide;

3-(4-Chloro-2,5-difluoro-benzyloxy)-5-(3-{5-[4-(2-hydroxy-ethyl)-piperazin-1-yl]-pentyl}-ureido)-isothiazole-4-carboxylic acid amide;

3-(4-Chloro-2,5-difluoro-benzyloxy)-5-{3-[7-(4-methyl-piperazin-1-yl)-heptyl]-ureido}-isothiazole-4-carboxylic acid amide;

3-(4-Chloro-2,5-difluoro-benzyloxy)-5-(3-{7-[4-(2-hydroxy-ethyl)-piperazin-1-yl]-heptyl}-ureido)-isothiazole-4-carboxylic acid amide;

3-(4-Chloro-2,5-difluoro-benzyloxy)-5-{3-[6-(4-methyl-piperazin-1-yl)-hexyl]-ureido}-isothiazole-4-carboxylic acid amide;

3-(4-Chloro-2,5-difluoro-benzyloxy)-5-{3-[6-(4-propyl-piperazin-1-yl)-hexyl]-ureido}-isothiazole-4-carboxylic acid amide;

5-(3-{5-[4-(2-Hydroxy-ethyl)-piperazin-1-yl]-pentyl}-ureido)-3-(4-methyl-benzyloxy)-isothiazole-4-carboxylic acid amide;

5-(3-{6-[4-(2-Hydroxy-ethyl)-piperazin-1-yl]-hexyl}-ureido)-3-(4-methyl-benzyloxy)-isothiazole-4-carboxylic acid amide;

3-(2,4-Dimethyl-benzyloxy)-5-{3-[5-(4-methyl-piperazin-1-yl)-pentyl]-ureido}-isothiazole-4-carboxylic acid amide;

3-(2,4-Dimethyl-benzyloxy)-5-{3-[7-(4-methyl-piperazin-1-yl)-heptyl]-ureido}-isothiazole-4-carboxylic acid amide;

3-(2,4-Dimethyl-benzyloxy)-5-{3-[6-(4-methyl-piperazin-1-yl)-hexyl]-ureido}-isothiazole-4-carboxylic acid amide;

3-(2,4-Dimethyl-benzyloxy)-5-(3-{7-[4-(2-hydroxy-ethyl)-piperazin-1-yl]-heptyl}-ureido)-isothiazole-4-carboxylic acid amide;

5-(3-{4-[Bis-(2-hydroxy-ethyl)-amino]-butyl}-ureido)-3-(4-chloro-2,5-difluoro-benzyloxy)-isothiazole-4-carboxylic acid amide;

3-(4-Chloro-2,5-difluoro-benzyloxy)-5-[3-(5-morpholin-4-yl-pentyl)-ureido]-isothiazole-4-carboxylic acid amide;

7-{3-[4-Carbamoyl-3-(4-chloro-2,5-difluoro-benzyloxy)-isothiazol-5-yl]-ureidomethyl}-octahydro-pyrido[1,2-a]pyrazine-2-carboxylic acid tert-butyl ester;

3-(4-Chloro-2,5-difluoro-benzyloxy)-5-{3-[4-(5-methyl-2,5-diaza-bicyclo[2.2.1]hept-2-yl)-butyl]-ureido}-isothiazole-4-carboxylic acid amide;

5-[3-(4-tert-Butylamino-3-hydroxy-butyl)-ureido]-3-(4-chloro-2,5-difluoro-benzyloxy)-isothiazole-4-carboxylic acid amide;

3-(4-Chloro-2,5-difluoro-benzyloxy)-5-[3-(octahydro-pyrido [1,2-a]pyrazin-7-ylmethyl)-ureido]-isothiazole-4-carboxylic acid amide;

5-[3-(5-Isopropylamino-pentyl)-ureido]-3-(2,4,5-trifluoro-benzyloxy)-isothiazole-4-carboxylic acid amide;

5-[3-(6-Dimethylamino-hexyl)-ureido]-3-(2,4,5-trifluoro-benzyloxy)-isothiazole-4-carboxylic acid amide;

5-[3-(4-Pyrrolidin-1-yl-butyl)-ureido]-3-(2,4,5-trifluoro-benzyloxy)-isothiazole-4-carboxylic acid amide;

5-(3-{6-[4-(2-Hydroxy-ethyl)-piperazin-1-yl]-hexyl}-ureido)-3-(2,4,5-trifluoro-benzyloxy)-isothiazole-4-carboxylic acid amide;

5-(3-{7-[4-(2-Hydroxy-ethyl)-piperazin-1-yl]-heptyl}-ureido)-3-(2,4,5-trifluoro-benzyloxy)-isothiazole-4-carboxylic acid amide;

5-[3-(2-Morpholin-4-yl-ethyl)-ureido]-3-(2,4,5-trifluoro-benzyloxy)-isothiazole-4-carboxylic acid amide 3-(4-Chloro-2,6-difluoro-benzyloxy)-5-[3-(4-pyrrolidin-1-yl-butyl)-ureido]-isothiazole-4-carboxylic acid amide;

3-(4-Chloro-2,6-difluoro-benzyloxy)-5-{3-[3-(4-methyl-piperazin-1-yl)-propyl]-ureido}-isothiazole-4-carboxylic acid amide;

5-(3-{3-[Bis-(2-hydroxy-ethyl)-amino]-propyl}-ureido)-3-(4-chloro-2,6-difluoro-benzyloxy)-isothiazole-4-carboxylic acid amide;

3-(4-Chloro-2,6-difluoro-benzyloxy)-5-{3-[2-(1-methyl-pyrrolidin-2-yl)-ethyl]-ureido}-isothiazole-4-carboxylic acid amide;

3-(4-Chloro-2,6-difluoro-benzyloxy)-5-(3-{4-[4-(2-hydroxy-ethyl)-piperazin-1-yl]-butyl}-ureido)-isothiazole-4-carboxylic acid amide;

3-(4-Chloro-2,6-difluoro-benzyloxy)-5-[3-(6-dimethylamino-hexyl)-ureido]-isothiazole-4-carboxylic acid amide;

3-(4-Chloro-2,6-difluoro-benzyloxy)-5-(3-{4-[4-(3-hydroxy-propyl)-piperazin-1-yl]-butyl}-ureido)-isothiazole-4-carboxylic acid amide;

3-(4-Chloro-2,6-difluoro-benzyloxy)-5-(3-{5-[4-(2-hydroxy-ethyl)-piperazin-1-yl ]-pentyl}-ureido)-isothiazole-4-carboxylic acid amide;

3-(4-Chloro-2,6-difluoro-benzyloxy)-5-(3-{6-[4-(2-hydroxy-ethyl)-piperazin-1-yl]-hexyl}-ureido)-isothiazole-4-carboxylic acid amide;

3-(4-Chloro-2,6-difluoro-benzyloxy)-5-[3-(5-isopropylamino-pentyl)-ureido]-isothiazole-4-carboxylic acid amide;

3-(4-Chloro-2,6-difluoro-benzyloxy)-5-{3-[4-(4-methyl-piperazin-1-yl)-butyl]-ureido}-isothiazole-4-carboxylic acid amide;

3-(4-Chloro-2,6-difluoro-benzyloxy)-5-{3-[5-(4-methyl-piperazin-1-yl)-pentyl]-ureido}-isothiazole-4-carboxylic acid amide;

5-[3-(4-tert-Butylamino-3-hydroxy-butyl)-ureido]-3-(2-fluoro-4-methyl-benzyloxy)-isothiazole-4-carboxylic acid amide;

3-(2-Fluoro-4-methyl-benzyloxy)-5-{3-[4-(5-methyl-2,5-diaza-bicyclo[2.2.1]hept-2-yl)-butyl]-ureido}-isothiazole-4-carboxylic acid amide;

3-(2-Fluoro-4-methyl-benzyloxy)-5-(3-{4-[4-(2-hydroxy-ethyl)-piperazin-1-yl]-butyl}-ureido)-isothiazole-4-carboxylic acid amide;

3-(2-Fluoro-4-methyl-benzyloxy)-5-[3-(3-isopropylamino-propyl)-ureido]-isothiazole-4-carboxylic acid amide;

3-(2,5-Difluoro-4-methyl-benzyloxy)-5-[3-(4-pyrrolidin-1-yl-butyl)-ureido]-isothiazole-4-carboxylic acid amide;

3-(2,5-Difluoro-4-methyl-benzyloxy)-5-(3-{4-[4-(3-hydroxy-propyl)-piperazin-1-yl]-butyl}-ureido)-isothiazole-4-carboxylic acid amide;

3-(2,5-Difluoro-4-methyl-benzyloxy)-5-[3-(3-isopropylamino-propyl)-ureido]-isothiazole-4-carboxylic acid amide;

3-(2,5-Difluoro-4-methyl-benzyloxy)-5-[3-(6-dimethylamino-hexyl)-ureido]-isothiazole-4-carboxylic acid amide;

3-(2,6-Difluoro-4-methyl-benzyloxy)-5-[3-(6-dimethylamino-hexyl)-ureido]-isothiazole-4-carboxylic acid amide;

3-(2,6-Difluoro-4-methyl-benzyloxy)-5-[3-(5-isopropylamino-pentyl)-ureido]-isothiazole-4-carboxylic acid amide;

5-(3-{3-[Bis-(2-hydroxy-ethyl)-amino]-propyl}-ureido)-3-(2,6-difluoro-4-methyl-benzyloxy)-isothiazole-4-carboxylic acid amide;

5-[3-(4-tert-Butylamino-3-hydroxy-butyl)-ureido]-3-(2,6-difluoro-4-methyl-benzyloxy)-isothiazole-4-carboxylic acid amide;

3-(2,6-Difluoro-4-methyl-benzyloxy)-5-[3-(4-pyrrolidin-1-yl-butyl)-ureido]-isothiazole-4-carboxylic acid amide;

3-(2,6-Difluoro-4-methyl-benzyloxy)-5-(3-{4-[4-(2-hydroxy-ethyl)-piperazin-1-yl]-butyl}-ureido)-isothiazole-4-carboxylic acid amide;

3-(2,6-Difluoro-4-methyl-benzyloxy)-5-(3-{5-[4-(2-hydroxy-ethyl)-piperazin-1-yl]-pentyl}-ureido)-isothiazole-4-carboxylic acid amide;

3-(2,6-Difluoro-4-methyl-benzyloxy)-5-(3-{6-[4-(2-hydroxy-ethyl)-piperazin-1-yl]-hexyl}-ureido)-isothiazole-4-carboxylic acid amide;

4-{3-[4-Carbamoyl-3-(2,5-difluoro-4-methyl-benzyloxy)-isothiazol-5-yl]-ureido}-butyric acid 5-(3-{3-[Bis-(2-hydroxy-ethyl)-amino]-propyl}-ureido)-3-(2-chloro-5-fluoro-4-methyl-benzyloxy)-isothiazole-4-carboxylic acid amide;

3-(2-Chloro-5-fluoro-4-methyl-benzyloxy)-5-[3-(5-isopropylamino-pentyl)-ureido]-isothiazole-4-carboxylic acid amide;

3-(2,6-Difluoro-4-methyl-benzyloxy)-5-[3-(6-dimethylamino-hexyl)-ureido]-isothiazole-4-carboxylic acid amide;

3-(2,6-Difluoro-4-methyl-benzyloxy)-5-[3-(5-isopropylamino-pentyl)-ureido]-isothiazole-4-carboxylic acid amide;

5-(3-{3-[Bis-(2-hydroxy-ethyl)-amino]-propyl}-ureido)-3-(2,6-difluoro-4-methyl-benzyloxy)-isothiazole-4-carboxylic acid amide;

5-[3-(4-tert-Butylamino-3-hydroxy-butyl)-ureido]-3-(2,6-difluoro-4-methyl-benzyloxy)-isothiazole-4-carboxylic acid amide;

3-(2,6-Difluoro-4-methyl-benzyloxy)-5-[3-(4-pyrrolidin-1-yl-butyl)-ureido]-isothiazole-4-carboxylic acid amide;

3-(2,6-Difluoro-4-methyl-benzyloxy)-5-(3-{4-[4-(2-hydroxy-ethyl)-piperazin-1-yl]-butyl}-ureido)-isothiazole-4-carboxylic acid amide;

3-(2,6-Difluoro-4-methyl-benzyloxy)-5-(3-{5-[4-(2-hydroxy-ethyl)-piperazin-1-yl]-pentyl}-ureido)-isothiazole-4-carboxylic acid amide;

3-(2,6-Difluoro-4-methyl-benzyloxy)-5-(3-{6-[4-(2-hydroxy-ethyl)-piperazin-1-yl]-hexyl}-ureido)-isothiazole-4-carboxylic acid amide;

5-[3-(3-tert-Butylamino-propyl)-ureido]-3-(2-fluoro-4-methyl-benzyloxy)-isothiazole-4-carboxylic acid amide;

3-(2,5-Difluoro-4-methyl-benzyloxy)-5-{3-[3-hydroxy-5-(4-methyl-piperazin-1-yl)-pentyl]-ureido}-isothiazole-4-carboxylic acid amide;

3-(2-Chloro-5-fluoro-4-methyl-benzyloxy)-5-[3-(4-pyrrolidin-1-yl-butyl)-ureido]-isothiazole-4-carboxylic acid amide;

3-(2-Chloro-5-fluoro-4-methyl-benzyloxy)-5-{3-[3-(4-methyl-piperazin-1-yl)-propyl]-ureido}-isothiazole-4-carboxylic acid amide;

3-(4-Chloro-2,5-difluoro-benzyloxy)-5-{3-[3-hydroxy-5-(4-methyl-piperazin-1-yl-pentyl]-ureido}-isothiazole-4-carboxylic acid amide;

3-(2,5-Difluoro-4-methyl-benzyloxy)-5-[3-(3-hydroxy-5-pyrrolidin-1-yl-pentyl)-ureido]-isothiazole-4-carboxylic acid amide;

3-(4-Chloro-2,5-difluoro-benzyloxy)-5-[3-(3-hydroxy-5-pyrrolidin-1-yl-pentyl)-ureido]-isothiazole-4-carboxylic acid amide;

3-(4-Chloro-2,6-difluoro-benzyloxy)-5-[3-(3-hydroxy-5-pyrrolidin-1-yl-pentyl)-ureido]-isothiazole-4-carboxylic acid amide;

3-(2-Chloro-5-fluoro-4-methyl-benzyloxy)-5-[3-(6-dimethylamino-hexyl)-ureido]-isothiazole-4-carboxylic acid amide;

3-(2-Chloro-5-fluoro-4-methyl-benzyloxy)-5-(3-{4-[4-(2-hydroxy-ethyl)-piperazin-1-yl]-butyl}-ureido)-isothiazole-4-carboxylic acid amide;

3-(4-Chloro-2,6-difluoro-benzyloxy)-5-{3-[3-hydroxy-5-(4-methyl-piperazin-1-yl)-pentyl]-ureido}-isothiazole-4-carboxylic acid amide;

3-(5-Chloro-2-fluoro-4-methyl-benzyloxy)-5-[3-(4-pyrrolidin-1-yl-butyl)-ureido]-isothiazole-4-carboxylic acid amide;

3-(5-Chloro-2-fluoro-4-methyl-benzyloxy)-5-{3-[3-(4-methyl-piperazin-1-yl)-propyl]-ureido}-isothiazole-4-carboxylic acid amide;

5-(3-{3-[Bis-(2-hydroxy-ethyl)-amino]-propyl}-ureido)-3-(5-chloro-2-fluoro-4-methyl-benzyloxy)-isothiazole-4-carboxylic acid amide;

5-[3-(4-tert-Butylamino-3-hydroxy-butyl)-ureido]-3-(2-fluoro-4,6-dimethyl-benzyloxy)-isothiazole-4-carboxylic acid amide;

3-(5-Chloro-2-fluoro-4-methyl-benzyloxy)-5-[3-(6-dimethylamino-hexyl)-ureido]-isothiazole-4-carboxylic acid amide;

3-(5-Chloro-2-fluoro-4-methyl-benzyloxy)-5-[3-(5-isopropylamino-pentyl)-ureido]-isothiazole-4-carboxylic acid amide;

5-[3-(6-Dimethylamino-hexyl)-ureido]-3-(2,4,6-trifluoro-benzyloxy)-isothiazole-4-carboxylic acid amide;

3-(5-Chloro-2-fluoro-4-methyl-benzyloxy)-5-(3-{4-[4-(2-hydroxy-ethyl)-piperazin-1-yl]-butyl}-ureido)-isothiazole-4-carboxylic acid amide;

3-(5-Chloro-2-fluoro-4-methyl-benzyloxy)-5-{3-[4-(4-methyl-piperazin-1-yl)-butyl]-ureido}-isothiazole-4-carboxylic acid amide;

3-(5-Chloro-2-fluoro-4-methyl-benzyloxy)-5-(3-{4-[4-(3-hydroxy-propyl)-piperazin-1-yl]-butyl}-ureido)-isothiazole-4-carboxylic acid amide;

3-(4-Chloro-2,6-difluoro-benzyloxy)-5-[3-(2-morpholin-4-yl-ethyl)-ureido]-isothiazole-4-carboxylic acid amide;

5-[3-(4-tert-Butylamino-3-hydroxy-butyl)-ureido]-3-(4-chloro-2,6-difluoro-benzyloxy)-isothiazole-4-carboxylic acid amide;

3-(4-Chloro-2,6-difluoro-benzyloxy)-5-{3-[4-(5-methyl-2,5-diaza-bicyclo[2.2.1]hept-2-yl)-butyl]-ureido}-isothiazole-4-carboxylic acid amide;

3-(4-Chloro-2,6-difluoro-benzyloxy)-5-[3-(3-hydroxy-5-isopropylamino-pentyl)-ureido]-isothiazole-4-carboxylic acid amide;

3-(4-Chloro-2,5-difluoro-benzyloxy)-5-[3-(3-hydroxy-5-isopropylamino-pentyl)-ureido]-isothiazole-4-carboxylic acid amide;

3-(5-Chloro-2-fluoro-4-methyl-benzyloxy)-5-(3-{5-[4-(2-hydroxy-ethyl)-piperazin-1-yl]-pentyl}-ureido)-isothiazole-4-carboxylic acid amide;

3-(5-Chloro-2-fluoro-4-methyl-benzyloxy)-5-(3-{6-[4-(2-hydroxy-ethyl)-piperazin-1-yl]-hexyl}-ureido)-isothiazole-4-carboxylic acid amide;

7-{3-[4-Carbamoyl-3-(4-chloro-2,6-difluoro-benzyloxy)-isothiazol-5-yl]-ureidomethyl)}-octahydro-pyrido[1,2-a]pyrazine-2-carboxylic acid tert-butyl ester;

3-(4-Chloro-2,5-difluoro-benzyloxy)-5-[3-(3-hydroxy-5-isopropylamino-pentyl)-ureido]-isothiazole-4-carboxylic acid amide;

3-(4-Chloro-2,6-difluoro-benzyloxy)-5-[3-(octahydro-pyrido[1,2-a]pyrazin-7-ylmethyl)-ureido]-isothiazole-4-carboxylic acid amide;

3-(4-Chloro-2,6-difluoro-benzyloxy)-5-(3-{3-[4-(2-hydroxy-ethyl)-piperazin-1-yl]-propyl}-ureido)-isothiazole-4-carboxylic acid amide;

5-(3-{4-[Bis-(2-hydroxy-ethyl)-amino]-butyl}-ureido)-3-(4-chloro-2,6-difluoro-benzyloxy)-isothiazole-4-carboxylic acid amide;

3-(4-Chloro-2,6-difluoro-benzyloxy)-5-(3-{3-[4-(2-hydroxy-ethyl)-piperazin-1-yl]-propyl}-ureido)-isothiazole-4-carboxylic acid amide;

5-(3-{3-[Bis-(2-hydroxy-ethyl)-amino]-propyl}-ureido)-3-(2,3-dichloro-4-methyl-benzyloxy)-isothiazole-4-carboxylic acid amide;

3-(2,3-Dichloro-4-methyl-benzyloxy)-5-[3-(6-dimethylamino-hexyl)-ureido]-isothiazole-4-carboxylic acid amide;

3-(2,3-Dichloro-4-methyl-benzyloxy)-5-[3-(4-pyrrolidin-1-yl-butyl)-ureido]-isothiazole-4-carboxylic acid amide;

3-(2,3-Dichloro-4-methyl-benzyloxy)-5-(3-{4-[4-(3-hydroxy-propyl)-piperazin-1-yl]-butyl}-ureido)-isothiazole-4-carboxylic acid amide;

5-(3-{4-[Bis-(2-hydroxy-ethyl)-amino]-butyl}-ureido)-3-(2,3-dichloro-4-methyl-benzyloxy)-isothiazole-4-carboxylic acid amide;

3-(2,3-Dichloro-4-methyl-benzyloxy)-5-(3-{5-[4-(2-hydroxy-ethyl)-piperazin-1-yl]-pentyl}-ureido)-isothiazole-4-carboxylic acid amide;

3-(2,3-Dichloro-4-methyl-benzyloxy)-5-(3-{6-[4-(2-hydroxy-ethyl)-piperazin-1-yl]-hexyl}-ureido)-isothiazole-4-carboxylic acid amide;

3-(2,5-Difluoro-4-methyl-benzyloxy)-5-(3-{5-[4-(2-hydroxy-ethyl)-piperazin-1-yl]-pentyl}-ureido)-isothiazole-4-carboxylic acid amide;

3-(2,5-Difluoro-4-methyl-benzyloxy)-5-(3-{6-[4-(2-hydroxy-ethyl)-piperazin-1-yl]-hexyl}-ureido)-isothiazole-4-carboxylic acid amide;

5-(3-{4-[Bis-(2-hydroxy-ethyl)-amino]-butyl}-ureido)-3-(2,5-difluoro-4-methyl-benzyloxy)-isothiazole-4-carboxylic acid amide;

3-(4-Chloro-2,5-difluoro-benzyloxy)-5-{3-[4-(5-methyl-2,5-diaza-bicyclo[2.2.1]hept-2-yl)-butyl]-ureido}-isothiazole-4-carboxylic acid amide;

3-(2,4-Dimethyl-benzyloxy)-5-[3-(5-isopropylamino-pentyl)-ureido]-isothiazole-4-carboxylic acid amide;

3-(4-Ethyl-benzyloxy)-5-(3-{5-[4-(2-hydroxy-ethyl)-piperazin-1-yl]-pentyl}-ureido)-isothiazole-4-carboxylic acid amide;

3-(4-Ethyl-benzyloxy)-5-(3-{6-[4-(2-hydroxy-ethyl)-piperazin-1-yl]-hexyl}-ureido)-isothiazole-4-carboxylic acid amide;

5-[3-(6-Dimethylamino-hexyl)-ureido]-3-(4-ethyl-benzyloxy)-isothiazole-4-carboxylic acid amide;

3-(4-Ethyl-benzyloxy)-5-[3-(5-isopropylamino-pentyl)-ureido]-isothiazole-4-carboxylic acid amide;

3-(2-Fluoro-4-methyl-benzyloxy)-5-(3-{5-[4-(2-hydroxy-ethyl)-piperazin-1-yl]-pentyl}-ureido)-isothiazole-4-carboxylic acid amide;

3-(2-Fluoro-4-methyl-benzyloxy)-5-(3-{6-[4-(2-hydroxy-ethyl)-piperazin-1-yl]-hexyl}-ureido)-isothiazole-4-carboxylic acid amide;

5-[3-(6-Dimethylamino-hexyl)-ureido]-3-(2-fluoro-4-methyl-benzyloxy)-isothiazole-4-carboxylic acid amide;

3-(2-Fluoro-4-methyl-benzyloxy)-5-[3-(5-isopropylamino-pentyl)-ureido]-isothiazole-4-carboxylic acid amide;

3-Heptyloxy-5-(3-{5-[4-(2-hydroxy-ethyl)-piperazin-1-yl]-pentyl}-ureido)-isothiazole-4-carboxylic acid amide;

3-Heptyloxy-5-(3-{6-[4-(2-hydroxy-ethyl)-piperazin-1-yl]-hexyl}-ureido)-isothiazole-4-carboxylic acid amide;

3-(2,5-Difluoro-4-methyl-benzyloxy)-5-{3-[4-(3,4-dihydroxy-pyrrolidin-1-yl)-butyl]-ureido}-isothiazole-4-carboxylic acid amide;

3-(4-Chloro-2,6-difluoro-benzyloxy)-5-{3-[4-(3,4-dihydroxy-pyrrolidin-1-yl)-butyl]-ureido}-isothiazole-4-carboxylic acid amide;

3-(2,5-Difluoro-4-methyl-benzyloxy)-5-[3-(4-pyrrolidin-1-yl-butyl)-ureido]-isothiazole-4-carboxylic acid amide;

3-(4-Chloro-2,6-difluoro-benzyloxy)-5-[3-(4-pyrrolidin-1-yl-butyl)-ureido]-isothiazole-4-carboxylic acid amide 3-(2,5-Difluoro-4-methyl-benzyloxy)-5-[3-(5-isopropylamino-pentyl)-ureido]-isothiazole-4-carboxylic acid amide;

5-[3-(5-Isopropylamino-pentyl)-ureido]-3-(2,4,6-trifluoro-benzyloxy)-isothiazole-4-carboxylic acid amide;

5-(3-{3-[Bis-(2-hydroxy-ethyl)-amino]-propyl}-ureido)-3-(2,4,6-trifluoro-benzyloxy)-isothiazole-4-carboxylic acid amide;

5-[3-(4-tert-Butylamino-3-hydroxy-butyl)-ureido]-3-(2,4,6-trifluoro-benzyloxy)-isothiazole-4-carboxylic acid amide;

5-[3-(4-Pyrrolidin-1-yl-butyl)-ureido]-3-(2,4,6-trifluoro-benzyloxy)-isothiazole-4-carboxylic acid amide;

5-(3-{4-[4-(2-Hydroxy-ethyl)-piperazin-1-yl]-butyl}-ureido)-3-(2,4,6-trifluoro-benzyloxy)-isothiazole-4-carboxylic acid amide;

5-(3-{5-[4-(2-Hydroxy-ethyl)-piperazin-1-yl]-pentyl}-ureido)-3-(2,4,6-trifluoro-benzyloxy)-isothiazole-4-carboxylic acid amide;

5-(3-{6-[4-(2-Hydroxy-ethyl)-piperazin-1-yl]-hexyl}-ureido)-3-(2,4,6-trifluoro-benzyloxy)-isothiazole-4-carboxylic acid amide;

3-(4-Bromo-2-fluoro-benzyloxy)-5-[3-(5-isopropylamino-pentyl)-ureido]-isothiazole-4-carboxylic acid amide;

3-(4-Bromo-2-fluoro-benzyloxy)-5-[3-(4-tert-butylamino-3-hydroxy-butyl)-ureido]-isothiazole-4-carboxylic acid amide;

3-(4-Bromo-2-fluoro-benzyloxy)-5-(3-{4-[4-(2-hydroxy-ethyl)-piperazin-1-yl]-butyl}-ureido)-isothiazole-4-carboxylic acid amide;

3-(4-Bromo-2-fluoro-benzyloxy)-5-(3-{5-[4-(2-hydroxy-ethyl)-piperazin-1-yl]-pentyl}-ureido)-isothiazole-4-carboxylic acid amide;

3-(2-Fluoro-4,6-dimethyl-benzyloxy)-5-[3-(5-isopropylamino-pentyl)-ureido]-isothiazole-4-carboxylic acid amide;

5-(3-{3-[Bis-(2-hydroxy-ethyl)-amino]-propyl}-ureido)-3-(2-fluoro-4,6-dimethyl-benzyloxy)-isothiazole-4-carboxylic acid amide;

3-(2-Fluoro-4,6-dimethyl-benzyloxy)-5-[3-(4-pyrrolidin-1-yl-butyl)-ureido]-isothiazole-4-carboxylic acid amide;

3-(2-Fluoro-4,6-dimethyl-benzyloxy)-5-(3-{4-[4-(2-hydroxy-ethyl)-piperazin-1-yl]-butyl}-ureido)-isothiazole-4-carboxylic acid amide;

3-(2-Fluoro-4,6-dimethyl-benzyloxy)-5-(3-{5-[4-(2-hydroxy-ethyl)-piperazin-1-yl]-pentyl}-ureido)-isothiazole-4-carboxylic acid amide;

3-(2-Fluoro-4,6-dimethyl-benzyloxy)-5-(3-{6-[4-(2-hydroxy-ethyl)-piperazin-1-yl ]-hexyl}-ureido)-isothiazole-4-carboxylic acid amide;

3-[1-(4-Chloro-2,6-difluoro-phenyl)-ethoxy]-5-[3-(4-pyrrolidin-1-yl-butyl)-ureido]-isothiazole-4-carboxylic acid amide;

3-[1-(4-Chloro-2,6-difluoro-phenyl)-ethoxy]-5-(3-{5-[4-(2-hydroxy-ethyl)-piperazin-1-yl]-pentyl}-ureido)-isothiazole-4-carboxylic acid amide;

5-[3-(6-Dimethylamino-hexyl)-ureido]-3-(2,3,6-trifluoro-4-methyl-benzyloxy)-isothiazole-4-carboxylic acid amide;

5-[3-(5-Isopropylamino-pentyl)-ureido]-3-(2,3,6-trifluoro-4-methyl-benzyloxy)-isothiazole-4-carboxylic acid amide;

5-(3-{6-[4-(2-Hydroxy-ethyl)-piperazin-1-yl]-hexyl}-ureido)-3-(2,3,6-trifluoro-4-methyl-benzyloxy)-isothiazole-4-carboxylic acid amide;

5-[3-(4-tert-Butylamino-3-hydroxy-butyl)-ureido]-3-[1-(4-chloro-2,6-difluoro-phenyl)-ethoxy]-isothiazole-4-carboxylic acid amide;

5-(3-{5-[4-(2-Hydroxy-ethyl)-piperazin-1-yl]-pentyl}-ureido)-3-(2,3,6-trifluoro-4-methyl-benzyloxy)-isothiazole-4-carboxylic acid amide;

3-[1-(4-Chloro-2,6-difluoro-phenyl)-ethoxy]-5-[3-(5-isopropylamino-pentyl)-ureido]-isothiazole-4-carboxylic acid amide;

5-[3-(4-tert-Butylamino-3-hydroxy-butyl)-ureido]-3-(2,3,6-trifluoro-4-methyl-benzyloxy)-isothiazole-3-(4-Chloro-2,6-difluoro-benzyloxy)-5-[3-(3-hydroxy-5-pyrrolidin-1-yl-pentyl)-ureido]-isothiazole-4-carboxylic acid amide;

3-(2,5-Difluoro-4-methyl-benzyloxy)-5-{3-[4-(2-hydroxymethyl-pyrrolidin-1-yl)-butyl]-ureido}-isothiazole-4-carboxylic acid amide;

5-(3-{5-[4-(2-Hydroxy-ethyl)-piperazin-1-yl]-pentyl}-ureido)-3-(4-methyl-benzyloxy)-isothiazole-4-carboxylic acid amide;

5-(3-{6-[4-(2-Hydroxy-ethyl)-piperazin-1-yl]-hexyl}-ureido)-3-(4-methyl-benzyloxy)-isothiazole-4-carboxylic acid amide;

5-[3-(6-Dimethylamino-hexyl)-ureido]-3-(4-methyl-benzyloxy)-isothiazole-4-carboxylic acid amide;

5-[3-(6-Dimethylamino-hexyl)-ureido]-3-heptyloxy-isothiazole-4-carboxylic acid amide;

3-Heptyloxy-5-[3-(5-isopropylamino-pentyl)-ureido]-isothiazole-4-carboxylic acid amide;

3-(4-Chloro-2,6-difluoro-benzyloxy)-5-{3-[4-(2-hydroxymethy)-butyl]-ureido}-isothiazole-4-carboxylic acid amide;

3-(5-Chloro-2-fluoro-4-methyl-benzyloxy)-5-{3-[4-(2-hydroxymethyl-pyrrolidin-1-yl)-butyl]-ureido}-isothiazole-4-carboxylic acid amide;

3-(2,5-Difluoro-4-methyl-benzyloxy)-5-{3-[4-(3-hydroxy-pyrrolidin-1-yl)-butyl]-ureido}-isothiazole-4-carboxylic acid amide;

5-[3-(6-Dimethylamino-hexyl)-ureido]-3-(2,3,5,6-tetrafluoro-4-methyl-benzyloxy)-isothiazole-4-carboxylic acid amide;

5-(3-{6-[4-(2-Hydroxy-ethyl)-piperazin-1-yl]-hexyl}-ureido)-3-(2,3,5,6-tetrafluoro-4-methyl-benzyloxy)-isothiazole-4-carboxylic acid amide;

3-(4-Chloro-2,5-difluoro-benzyloxy)-5-{3-[4-(2-hydroxymethyl-pyrrolidin-1-yl)-butyl]-ureido}-isothiazole-4-carboxylic acid amide;

5-[3-(4-Pyrrolidin-1-yl-butyl)-ureido]-3-(2,3,5,6-tetrafluoro-4-methyl-benzyloxy)-isothiazole-4-carboxylic acid amide;

3-(4-Chloro-2,5-difluoro-benzyloxy)-5-{3-[4-(3-hydroxy-pyrrolidin-1-yl)-butyl]-ureido}-isothiazole-4-carboxylic acid amide;

3-(4-Chloro-2,5-difluoro-benzyloxy)-5-{3-[4-(3,4-dihydroxy-pyrrolidin-1-yl)-butyl]-ureido}-isothiazole-4-carboxylic acid amide;

5-[3-(4-tert-Butylamino-3-hydroxy-butyl)-ureido]-3-(2,3,5,6-tetrafluoro-4-methyl-benzyloxy)-isothiazole-4-carboxylic acid amide;

3-(4-Chloro-2,6-difluoro-benzyloxy)-5-{3-[4-(3-hydroxy-pyrrolidin-1-yl)-butyl]-ureido}-isothiazole-4-carboxylic acid amide;

5-[3-(5-Isopropylamino-pentyl)-ureido]-3-(2,3,5,6-tetrafluoro-4-methyl-benzyloxy)-isothiazole-4-carboxylic acid amide;

3-(4-Chloro-2,5-difluoro-benzyloxy)-5-{3-[2-(octahydro-pyrido[1,2-a]pyrazin-7-yl)-ethyl]-ureido}-isothiazole-4-carboxylic acid amide;

3-(2,5-Difluoro-4-methyl-benzyloxy)-5-{3-[6-(4-methyl-piperazin-1-yl)-hexyl]-ureido}-isothiazole-4-carboxylic acid amide;

3-(2-Fluoro-4-methyl-benzyloxy)-5-{3-[3-(4-methyl-piperazin-1-yl)-propyl]-ureido}-isothiazole-4-carboxylic acid amide;

3-(2,5-Difluoro-4-methyl-benzyloxy)-5-[3-(4-piperidin-1-yl-butyl)-ureido]-isothiazole-4-carboxylic acid amide;

3-(4-Chloro-2,6-difluoro-benzyloxy)-5-[3-(4-piperidin-1-yl-butyl)-ureido]-isothiazole-4-carboxylic acid amide;

3-(2,3-Difluoro-4-methyl-benzyloxy)-5-[3-(4-piperidin-1-yl-butyl)-ureido]-isothiazole-4-carboxylic acid amide;

3-(4-Chloro-2,5-difluoro-benzyloxy)-5-[3-(4-piperidin-1-yl-butyl)-ureido]-isothiazole-4-carboxylic acid amide;

3-(4-Bromo-2,6-difluoro-benzyloxy)-5-[3-(6-dimethylamino-hexyl)-ureido]-isothiazole-4-carboxylic acid amide;

3-(4-Bromo-2,6-difluoro-benzyloxy)-5-[3-(5-isopropylamino-pentyl)-ureido]-isothiazole-4-carboxylic acid amide;

3-(4-Bromo-2,6-difluoro-benzyloxy)-5-(3-{6-[4-(2-hydroxy-ethyl)-piperazin-1-yl]-hexyl}-ureido)-isothiazole-4-carboxylic acid amide;

3-(4-Bromo-2,6-difluoro-benzyloxy)-5-(3-{5-[4-(2-hydroxy-ethyl)-piperazin-1-yl]-pentyl}-ureido)-isothiazole-4-carboxylic acid amide;

3-(4-Bromo-2,6-difluoro-benzyloxy)-5-[3-(4-tert-butylamino-3-hydroxy-butyl)-ureido]-isothiazole-4-carboxylic acid amide;

3-(4-Bromo-2,6-difluoro-benzyloxy)-5-[3-(4-pyrrolidin-1-yl-butyl)-ureido]-isothiazole-4-carboxylic acid amide;

3-(4-Chloro-2,6-difluoro-benzyloxy)-5-(3-{4-[4-(2-hydroxy-ethyl)-piperazin-1-yl]-butyl}-ureido)-isothiazole-4-carboxylic acid amide;

3-(2-Fluoro-4-methyl-benzyloxy)-5-[3-(4-hydroxy-5-piperidin-1-yl-pentyl)-ureido]-isothiazole-4-carboxylic acid amide 3-(2,6-Difluoro-4-methyl-benzyloxy)-5-[3-(4-hydroxy-5-piperidin-1-yl-pentyl)-ureido]-isothiazole-4-carboxylic acid amide;

3-(2-Fluoro-4-methyl-benzyloxy)-5-[3-(4-hydroxy-5-isobutylamino-pentyl)-ureido]-isothiazole-4-carboxylic acid amide;

5-[3-(4-tert-Butylamino-3-hydroxy-butyl)-ureido]-3-(2-fluoro-4-methyl-benzyloxy)-isothiazole-4-carboxylic acid amide;

3-(2,3-Difluoro-4-methyl-benzyloxy)-5-{3-[4-(3,4-dihydroxy-pyrrolidin-1-yl)-butyl]-ureido}-isothiazole-4-carboxylic acid amide;

3-(4-Chloro-2,6-difluoro-benzyloxy)-5-{3-[4-(3,4-dihydroxy-pyrrolidin-1-yl)-butyl]-ureido}-isothiazole-4-carboxylic acid amide;

3-(4-Chloro-2,5-difluoro-benzyloxy)-5-{3-[4-(3,4-dihydroxy-pyrrolidin-1-yl)-butyl]-ureido}-isothiazole-4-carboxylic acid amide;

3-(2,5-Difluoro-4-methyl-benzyloxy)-5-{3-[4-(3,4-dihydroxy-pyrrolidin-1-yl)-butyl]-ureido}-isothiazole-4-carboxylic acid amide;

3-(4-Chloro-2,6-difluoro-benzyloxy)-5-{3-[3-(4-methyl-piperazin-1-yl)-propyl]-ureido}-isothiazole-4-carboxylic acid amide;

3-(2,5-Difluoro-4-methyl-benzyloxy)-5-[3-(4-hydroxy-5-morpholin-4-yl-pentyl)-ureido]-isothiazole-4-carboxylic acid amide;

3-(2,5-Difluoro-4-methyl-benzyloxy)-5-[3-(5-hydroxy-6-morpholin-4-yl-hexyl)-ureido]-isothiazole-4-carboxylic acid amide;

3-(4-Chloro-2,6-difluoro-benzyloxy)-5-[3-(5-hydroxy-6-morpholin-4-yl-hexyl)-ureido]-isothiazole-4-carboxylic acid amide;

3-(2,5-Difluoro-4-methyl-benzyloxy)-5-[3-(4-hydroxy-5-piperidin-1-yl-pentyl)-ureido]-isothiazole-4-carboxylic acid amide 3-(4-Chloro-2,6-difluoro-benzyloxy)-5-[3-(4-hydroxy-5-piperidin-1-yl-pentyl)-ureido]-isothiazole-4-carboxylic acid amide;

3-(2,3-Difluoro-4-methyl-benzyloxy)-5-[3-(4-hydroxy-5-piperidin-1-yl-pentyl)-ureido]-isothiazole-4-carboxylic acid amide;

3-(2,5-Difluoro-4-methyl-benzyloxy)-5-{3-[4-(3-hydroxy-piperidin-1-yl)-butyl]-ureido}-isothiazole-4-carboxylic acid amide;

3-(4-Chloro-2,6-difluoro-benzyloxy)-5-{3-[4-(3-hydroxy-piperidin-1-yl)-butyl]-ureido}-isothiazole-4-carboxylic acid amide;

3-(2,3-Difluoro-4-methyl-benzyloxy)-5-(3-[4-(3-hydroxy-piperidin-1-yl)-butyl]-ureido}-isothiazole-4-carboxylic acid amide;

3-(2,6-Difluoro-benzyloxy)-5-{3-[3-(4-methyl-piperazin-1-yl)-propyl]-ureido}-isothiazole-4-carboxylic acid amide;

3-(2,6-Difluoro-benzyloxy)-5-[3-(6-dimethylamino-hexyl)-ureido]-isothiazole-4-carboxylic acid amide;

3-(2,6-Difluoro-4-methyl-benzyloxy)-5-[3-(5-hydroxy-6-morpholin-4-yl-hexyl)-ureido]-isothiazole-4-carboxylic acid amide;

3-(2-Fluoro-4-methyl-benzyloxy)-5-[3-(4-hydroxy-5-morpholin-4-yl-pentyl)-ureido]-isothiazole-4-carboxylic acid amide;

3-(2-Fluoro-4-methyl-benzyloxy)-5-[3-(5-hydroxy-6-morpholin-4-yl-hexyl)-ureido]-isothiazole-4-carboxylic acid amide;

3-(2,6-Difluoro-4-methyl-benzyloxy)-5-[3-(5-hydroxy-6-isobutylamino-hexyl)-ureido]-isothiazole-4-carboxylic acid amide;

3-(2,6-Difluoro-4-methyl-benzyloxy)-5-[3-(5-hydroxy-6-piperidin-1-yl-hexyl)-ureido]-isothiazole-4-carboxylic acid amide;

3-(2,6-Difluoro-4-methyl-benzyloxy)-5-[3-(6-hydroxy-7-morpholin-4-yl-heptyl)-ureido]-isothiazole-4-carboxylic acid amide;

3-(2,6-Difluoro-4-methyl-benzyloxy)-5-[3-(4-hydroxy-5-morpholin-4-yl-pentyl)-ureido]-isothiazole-4-carboxylic acid amide;

3-(2,6-Difluoro-4-methyl-benzyloxy)-5-[3-(7-dimethylamino-6-hydroxy-heptyl)-ureido]-isothiazole-4-carboxylic acid amide 3-(2,6-Difluoro-4-methyl-benzyloxy)-5-[3-(6-hydroxy-7-piperidin-1-yl-heptyl)-ureido]-isothiazole-4-carboxylic acid amide;

3-(4-Chloro-2,6-difluoro-benzyloxy)-5-{3-[4-(2-methoxymethyl-pyrrolidin-1-yl)-butyl]-ureido}-isothiazole-4-carboxylic acid amide;

3-(4-Chloro-2,6-difluoro-benzyloxy)-5-{3-[4-(2-hydroxymethyl-piperidin-1-yl)-butyl]-ureido}-isothiazole-4-carboxylic acid amide;

3-(2,5-Difluoro-4-methyl-benzyloxy)-5-(3-{4-[ethyl-(2-hydroxy-ethyl)-amino]-butyl}-ureido)-isothiazole-4-carboxylic acid amide;

3-(4-Chloro-2,6-difluoro-benzyloxy)-5-(3-{4-[ethyl-(2-hydroxy-ethyl)-amino]-butyl}-ureido)-isothiazole-4-carboxylic acid amide;

3-(2,3-Difluoro-4-methyl-benzyloxy)-5-(3-{4-[ethyl-(2-hydroxy-ethyl)-amino]-butyl}-ureido)-isothiazole-4-carboxylic acid amide;

3-(2,5-Difluoro-4-methyl-benzyloxy)-5-{3-[4-(2-methoxymethyl-pyrrolidin-1-yl)-butyl]-ureido}-isothiazole-4-carboxylic acid amide;

3-(2,5-Difluoro-4-methyl-benzyloxy)-5-{3-[4-(2-hydroxymethyl-piperidin-1-yl)-butyl]-ureido}-isothiazole-4-carboxylic acid amide;

5-[3-(6-Dimethylamino-hexyl)-ureido]-3-(2,3,6-trifluoro-benzyloxy)-isothiazole-4-carboxylic acid amide;

5-{3-[3-(4-Methyl-piperazin-1-yl)-propyl]-ureido}-3-(2,3,6-trifluoro-benzyloxy)-isothiazole-4-carboxylic acid amide;

3-(2,3-Difluoro-4-methyl-benzyloxy)-5-[3-(5-hydroxy-6-piperidin-1-yl-hexyl)-ureido]-isothiazole-4-carboxylic acid amide;

3-(4-Chloro-2-fluoro-benzyloxy)-5-[3-(5-hydroxy-6-piperidin-1-yl-hexyl)-ureido]-isothiazole-4-carboxylic acid amide;

3-(4-Ethyl-2,3-difluoro-benzyloxy)-5-[3-(5-hydroxy-6-piperidin-1-yl-hexyl)-ureido]-isothiazole-4-carboxylic acid amide;

3-(4-Chloro-2,6-difluoro-benzyloxy)-5-[3-(5-hydroxy-6-piperidin-1-yl-hexyl)-ureido]-isothiazole-4-carboxylic acid amide;

3-(4-Chloro-2-fluoro-benzyloxy)-5-[3-(5-hydroxy-6-morpholin-4-yl-hexyl)-ureido]-isothiazole-4-carboxylic acid amide;

3-(4-Chloro-2-fluoro-benzyloxy)-5-[3-(6-hydroxy-7-morpholin-4-ylheptyl)-ureido]-isothiazole-4-carboxylic acid amide;

3-(4-Chloro-2,6-difluoro-benzyloxy)-5-[3-(6-hydroxy-7-morpholin-4-yl-heptyl)-ureido]-isothiazole-4-carboxylic acid amide;

3-(2,5-Difluoro-4-methyl-benzyloxy)-5-[3-(6-hydroxy-7-morpholin-4-yl-heptyl)-ureido]-isothiazole-4-carboxylic acid amide;

3-(2,5-Difluoro-4-methyl-benzyloxy)-5-[3-(5-hydroxy-6-piperidin-1-yl-hexyl)-ureido]-isothiazole-4-carboxylic acid amide;

3-(2,5-Difluoro-4-methyl-benzyloxy)-5-[3-(6-hydroxy-7-piperidin-1-yl-heptyl)-ureido]-isothiazole-4-carboxylic acid amide;

3-(2,5-Difluoro-4-methyl-benzyloxy)-5-[3-(7-dimethylamino-6-hydroxy-heptyl)-ureido]-isothiazole-4-carboxylic acid amide;

3-(4-Chloro-2,6-difluoro-benzyloxy)-5-[3-(6-hydroxy-7-piperidin-1-yl-heptyl)-ureido]-isothiazole-4-carboxylic acid amide;

3-(4-Chloro-2,6-difluoro-benzyloxy)-5-[3-(7-dimethylamino-6-hydroxy-heptyl)-ureido]-isothiazole-4-carboxylic acid amide;

3-(2,5-Difluoro-4-methyl-benzyloxy)-5-[3-(5-hydroxy-6-isobutylamino-hexyl)-ureido]-isothiazole-4-carboxylic acid amide;

3-(4-Chloro-2,6-difluoro-benzyloxy)-5-[3-(5-hydroxy-6-isobutylamino-hexyl)-ureido]-isothiazole-4-carboxylic acid amide;

3-(4-Bromo-2,3,6-trifluoro-benzyloxy)-5-{3-[3-(4-methyl-piperazin-1-yl)-propyl]-ureido}-isothiazole-4-carboxylic acid amide;

3-(4-Bromo-2,3,6-trifluoro-benzyloxy)-5-[3-(6-dimethylamino-hexyl)-ureido]-isothiazole-4-carboxylic acid amide;

3-(2-Fluoro-4-methyl-benzyloxy)-5-{3-[3-(4-methyl-piperazin-1-yl)-propyl]-ureido}-isothiazole-4-carboxylic acid amide;

3-(2,5-Difluoro-4-methyl-benzyloxy)-5-{3-[4-(2-hydroxymethyl-pyrrolidin-1-yl)-butyl]-ureido}-isothiazole-4-carboxylic acid amide;

3-(3-Chloro-2,6-difluoro-benzyloxy)-5-[3-(6-dimethylamino-hexyl)-ureido]-isothiazole-4-carboxylic acid amide;

3-(3-Chloro-2,6-difluoro-benzyloxy)-5-{3-[3-(4-methyl-piperazin-1-yl)-propyl]-ureido}-isothiazole-4-carboxylic acid amide;

3-(2,6-Difluoro-4-methyl-benzyloxy)-5-{3-[3-(4-methyl-piperazin-1-yl)-propyl]-ureido}-isothiazole-4-carboxylic acid amide;

3-(2,6-Difluoro-4-methyl-benzyloxy)-5-[3-(4-pyrrolidin-1-yl-butyl)-ureido]-isothiazole-4-carboxylic acid amide;

3-(2,6-Difluoro-4-methyl-benzyloxy)-5-[3-(3-hydroxy-5-pyrrolidin-1-yl-pentyl)-ureido]-isothiazole-4-carboxylic acid amide;

3-(2,5-Difluoro-4-methyl-benzyloxy)-5-[3-(4-hydroxy-5-piperidin-1-yl-pentyl)-ureido]-isothiazole-4-carboxylic acid amide;

3-(4-Chloro-2,6-difluoro-benzyloxy)-5-[3-(4-piperidin-1-yl-butyl)-ureido]-isothiazole-4-carboxylic acid amide;

3-(2,5-Difluoro-4-methyl-benzyloxy)-5-[3-(3-hydroxy-5-pyrrolidin-1-yl-pentyl)-ureido]-isothiazole-4-carboxylic acid amide;

3-(2,5-Difluoro-4-methyl-benzyloxy)-5-{3-[4-(3-hydroxy-pyrrolidin-1-yl)-butyl]-ureido{-isothiazole-4-carboxylic acid amide;

5-[3-(4-Pyrrolidin-1-yl-butyl)-ureido]-3-(2,3,6-trifluoro-4-methyl-benzyloxy)-isothiazole-4-carboxylic acid amide;

5-{3-[3-(4-Methyl-piperazin-1-yl)-propyl]-ureido}-3-(2,3,6-trifluoro-4-methyl-benzyloxy)-isothiazole-4-carboxylic acid amide;

5-[3-(3-Hydroxy-5-pyrrolidin-1-yl-pentyl)-ureido]-3-(2,3,6-trifluoro-4-methyl-benzyloxy)-isothiazole-4-carboxylic acid amide;

3-(2,5-Difluoro-4-methyl-benzyloxy)-5-{3-[3-(4-methyl-piperazin-1-yl)-propyl]-ureido}-isothiazole-4-carboxylic acid amide;

3-(4-Chloro-2,5-difluoro-benzyloxy)-5-{3-[4-(2-hydroxymethyl-pyrrolidin-1-yl)-butyl]-ureido}-isothiazole-4-carboxylic acid amide;

3-(4-Chloro-2,5-difluoro-benzyloxy)-5-(3-{4-[ethyl-(2-hydroxy-ethyl)-amino]-butyl}-ureido)-isothiazole-4-carboxylic acid amide 3-(4-Chloro-2,5-difluoro-benzyloxy)-5-[3-(4-hydroxy-5-piperidin-1-yl-pentyl)-ureido]-isothiazole-4-carboxylic acid amide;

3-(4-Chloro-2,5-difluoro-benzyloxy)-5-{3-[4-(3-hydroxy-piperidin-1-yl)-butyl]-ureido}-isothiazole-4-carboxylic acid amide;

3-(4-Chloro-2,6-difluoro-benzyloxy)-5-[3-(3-pyrrolidin-1-yl-propyl)-ureido]-isothiazole-4-carboxylic acid amide;

3-(4-Chloro-2,6-difluoro-benzyloxy)-5-{3-[2-(1-methyl-pyrrolidin-2-yl)-ethyl]-ureido}-isothiazole-4-carboxylic acid amide;

3-(4-Chloro-2,6-difluoro-benzyloxy)-5-{3-[4-(2-hydroxymethyl-piperidin-1-yl)-butyl]-ureido}-isothiazole-4-carboxylic acid amide;

3-(2,5-Difluoro-4-methyl-benzyloxy)-5-{3-[3-(5-methyl-2,5-diaza-bicyclo[2.2.1]hept-2-yl)-propyl]-ureido}-isothiazole-4-carboxylic acid amide;

3-(4-Chloro-2,6-difluoro-benzyloxy)-5-{3-[3-(5-methyl-2,5-diaza-bicyclo[2.2.1]hept-2-yl)-propyl]-ureido}-isothiazole-4-carboxylic acid amide;

3-(4-Chloro-2,5-difluoro-benzyloxy)-5-{3-[4-(2-hydroxymethyl-piperidin-1-y)-butyl]-ureido}-isothiazole-4-carboxylic acid amide;

3-(4-Chloro-2,6-difluoro-benzyloxy)-5-[3-ethyl-3-(4-pyrrolidin-1-yl-butyl)-ureido]-isothiazole-4-carboxylic acid amide;

3-(2,5-Difluoro-4-methyl-benzyloxy)-5-[3-ethyl-3-(4-pyrrolidin-1-yl-butyl)-ureido]-isothiazole-4-carboxylic acid amide;

3-(4-Chloro-2,3,6-trifluoro-benzyloxy)-5-{3-[3-(5-methyl-2,5-diaza-bicyclo[2.2.1]hept-2-yl)-propyl]-ureido}-isothiazole-4-carboxylic acid amide;

3-(4-Chloro-2,3,6-trifluoro-benzyloxy)-5-{3-[2-(1-methyl-pyrrolidin-2-yl)-ethyl]-ureido}-isothiazole-4-carboxylic acid amide;

3-(4-Chloro-2,3,6-trifluoro-benzyloxy)-5-[3-(4-pyrrolidin-1-yl-butyl)-ureido]-isothiazole-4-carboxylic acid amide;

3-(4-Chloro-2,3,6-trifluoro-benzyloxy)-5-{3-[4-(2-hydroxymethyl-pyrrolidin-1-yl)-butyl]-ureido}-isothiazole-4-carboxylic acid amide;

3-(4-Chloro-2,3,6-trifluoro-benzyloxy)-5-{3-[3-(4-methyl-piperazin-1-yl)-propyl]-ureido)-isothiazole-4-carboxylic acid amide;

3-(4-Chloro-2,3,6-trifluoro-benzyloxy)-5-(3-{4-[ethyl-(2-hydroxy-ethyl)-amino]-butyl}-ureido)-isothiazole-4-carboxylic acid amide;

3-(4-Chloro-2,6-difluoro-benzyloxy)-5-{3-ethyl-3-[3-(4-methyl-piperazin-1-yl)-propyl]-ureido}-isothiazole-4-carboxylic acid amide;

3-(2,5-Difluoro-4-methyl-benzyloxy)-5-{3-ethyl-3-[3-(4-methyl-piperazin-1-yl)-propyl]-ureido}-isothiazole-4-carboxylic acid amide;

3-(4-Chloro-2,6-difluoro-benzyloxy)-5-[3-ethyl-3-(4-piperidin-1-yl-butyl)-ureido]-isothiazole-4-carboxylic acid amide;

3-(2,5-Difluoro-4-methyl-benzyloxy)-5-[3-ethyl-3-(4-piperidin-1-yl-butyl)-ureido]-isothiazole-4-carboxylic acid amide;

5-(3-Methyl-ureido)-3-(2,3,6-trifluoro-4-methyl-benzyloxy)-isothiazole-4-carboxylic acid amide;

5-(3-Ethyl-ureido)-3-(2,3,6-trifluoro-4-methyl-benzyloxy)-isothiazole-4-carboxylic acid amide;

5-(3-Cyclopropylmethyl-ureido)-3-(2,3,6-trifluoro-4-methyl-benzyloxy)-isothiazole-4-carboxylic acid amide;

5-(3-Cyclobutyl-ureido)-3-(2,3,6-trifluoro-4-methyl-benzyloxy)-isothiazole-4-carboxylic acid amide;

5-(3-Allyl-ureido)-3-(2,3,6-trifluoro-4-methyl-benzyloxy)-isothiazole-4-carboxylic acid amide;

5-(3-isobutyl-ureido)-3-(2,3,6-trifluoro-4-methyl-benzyloxy)-isothiazole-4-carboxylic acid amide;

5-[3-(3-Hydroxy-propyl)-ureido]-3-(2,3,6-trifluoro-4-methyl-benzyloxy)-isothiazole-4-carboxylic acid amide;

5-{3-[2-(1-Methyl-pyrrolidin-2-yl)-ethyl]-ureido}-3-(2,3,6-trifluoro-4-methyl-benzyloxy)-isothiazole-4-carboxylic acid amide;

5-[3-(2-Dimethylamino-ethyl)-ureido]-3-(2,3,6-trifluoro-4-methyl-benzyloxy)-isothiazole-4-carboxylic acid amide;

5-[3-(4-Dimethylamino-butyl)-ureido]-3-(2,3,6-trifluoro-4-methyl-benzyloxy)-isothiazole-4-carboxylic acid amide;

5-[3-(7-Dimethylamino-6-hydroxy-heptyl)-ureido]-3-(2,3,6-trifluoro-4-methyl-benzyloxy)-isothiazole-4-carboxylic acid amide;

5-{3-[4-(5-Methyl-2,5-diaza-bicyclo[2.2.1]hept-2-yl)-butyl]-ureido}-3-(2,3,6-trifluoro-4-methyl-benzyloxy)-isothiazole-4-carboxylic acid amide;

5-[3-(3-Dimethylamino-propyl)-ureido]-3-(2,3,6-trifluoro-4-methyl-benzyloxy)-isothiazole-4-carboxylic acid amide;

5-[3-(3-Hydroxy-5-isopropylamino-pentyl)-ureido]-3-(2,3,6-trifluoro-4-methyl-benzyloxy)-isothiazole-4-carboxylic acid amide;

5-[3-(3-Isopropylamino-propyl)-ureido]-3-(2,3,6-trifluoro-4-methyl-benzyloxy)-isothiazole-4-carboxylic acid amide;

5-{3-[3-(4-Methyl-piperazin-1-yl)-propyl]-ureido}-3-(2,3,6-trifluoro-4-methyl-benzyloxy)-isothiazole-4-carboxylic acid amide;

5-{3-[4-(4-Methyl-piperazin-1-yl)-butyl]-ureido}-3-(2,3,6-trifluoro-4-methyl-benzyloxy)-isothiazole-4-carboxylic acid amide;

5-{3-[5-(4-Methyl-piperazin-1-yl)-pentyl]-ureido}-3-(2,3,6-trifluoro-4-methyl-benzyloxy)-isothiazole-4-carboxylic acid amide;

5-{3-[6-(4-Methyl-piperazin-1-yl)-hexyl]-ureido}-3-(2,3,6-trifluoro-4-methyl-benzyloxy)-isothiazole-4-carboxylic acid amide;

5-{3-[3-Hydroxy-5-(4-methyl-piperazin-1-yl)-pentyl]-ureido}-3-(2,3,6-trifluoro-4-methyl-benzyloxy)-isothiazole-4-carboxylic acid amide;

5-(3-{4-[4-(2-Hydroxy-ethyl)-piperazin-1-yl]-butyl}-ureido)-3-(2,3,6-trifluoro-4-methyl-benzyloxy)-isothiazole-4-carboxylic acid amide;

5-(3-{4-[4-(3-Hydroxy-propyl)-piperazin-1-yl]-butyl}-ureido)-3-(2,3,6-trifluoro-4-methyl-benzyloxy)-isothiazole-4-carboxylic acid amide;

5-[3-(3-Pyrrolidin-1-yl-propyl)-ureido]-3-(2,3,6-trifluoro-4-methyl-benzyloxy)-isothiazole-4-carboxylic acid amide;

5-[3-(3-Hydroxy-5-pyrrolidin-1-yl-pentyl)-ureido]-3-(2,3,6-trifluoro-4-methyl-benzyloxy)-isothiazole-4-carboxylic acid amide;

3-(4-Chloro-2,6-difluoro-benzyloxy)-5-[3-methyl-3-(4-piperidin-1-yl-butyl)-ureido]-isothiazole-4-carboxylic acid amide;

3-(2,5-Difluoro-4-methyl-benzyloxy)-5-[3-methyl-3-(4-piperidin-1-yl-butyl)-ureido]-isothiazole-4-carboxylic acid amide;

5-[3-(4-Pyrrolidin-1-yl-butyl)-ureido]-3-(2,3,6-trifluoro-4-methyl-benzyloxy)-isothiazole-4-carboxylic acid amide;

5-[3-(4-Hydroxy-5-piperidin-1-yl-pentyl)-ureido]-3-(2,3,6-trifluoro-4-methyl-benzyloxy-isothiazole-4-carboxylic acid amide;

5-[3-(5-Hydroxy-6-piperidin-1-yl-hexyl)-ureido]-3-(2,3,6-trifluoro-4-methyl-benzyloxy)-isothiazole-4-carboxylic acid amide;

5-[3-(5-Hydroxy-7-piperidin-1-yl-heptyl)-ureido]-3-(2,3,6-trifluoro-4-methyl-benzyloxy)-isothiazole-4-carboxylic acid amide;

3-(2,6-Difluoro-4-methyl-benzyloxy)-5-{3-[3-(4-methyl-piperazin-1-yl)-propyl]-ureido}-isothiazole-4-carboxylic acid amide;

3-(2,6-Difluoro-4-methyl-benzyloxy)-5-{3-[3-(4-methyl-piperazin-1-yl)-propyl]-ureido}-isothiazole-4-carboxylic acid amide;

5-[3-(4-Hydroxy-5-morpholin-4-yl-pentyl)-ureido]-3-(2,3,6-trifluoro-4-methyl-benzyloxy)-isothiazole-4-carboxylic acid amide;

5-[3-(5-Hydroxy-6-morpholin-4-yl-hexyl)-ureido]-3-(2,3,6-trifluoro-4-methyl-benzyloxy)-isothiazole-4-carboxylic acid amide;

5-[3-(5-Hydroxy-7-morpholin-4-yl-heptyl)-ureido]-3-(2,3,6-trifluoro-4-methyl-benzyloxy)-isothiazole-4-carboxylic acid amide;

5-[3-(2-Morpholin-4-yl-ethyl)-ureido]-3-(2,3,6-trifluoro-4-methyl-benzyloxy)-isothiazole-4-carboxylic acid amide;

5-[3-(4-Morpholin-4-yl-butyl)-ureido]-3-(2,3,6-trifluoro-4-methyl-benzyloxy)-isothiazole-4-carboxylic acid amide;

5-(3-{3-[Bis-(2-hydroxy-ethyl)-amino]-propyl}-ureido)-3-(2,3,6-trifluoro-4-methyl-benzyloxy)-isothiazole-4-carboxylic acid amide;

5-(3-{4-[Bis -(2-hydroxy-ethyl)-amino]-butyl}-ureido)-3-(2,3,6-trifluoro-4-methyl-benzyloxy)-isothiazole-4-carboxylic acid amide;

5-(3-{4-[Ethyl-(2-hydroxy-ethyl)-amino]-butyl}-ureido)-3-(2,3,6-trifluoro-4-methyl-benzyloxy)-isothiazole-4-carboxylic acid amide;

5-[3-(3-tert-Butylamino-propyl)-ureido]-3-(2,3,6-trifluoro-4-methyl-benzyloxy)-isothiazole-4-carboxylic acid amide;

3-(4-Chloro-2,6-difluoro-benzyloxy)-5-[3-(4-imidazol-1-yl-butyl)-ureido]-isothiazole-4-carboxylic acid amide;

3-(4-Chloro-2,3,6-trifluoro-benzyloxy)-5-{3-[4-(3-hydroxy-pyrrolidin-1-yl)-butyl]-ureido}-isothiazole-4-carboxylic acid amide;

3-(2,5-Difluoro-4-methyl-benzyloxy)-5-[3-(4-imidazol-1-yl-butyl)-ureido]-isothiazole-4-carboxylic acid amide;

5-{3-[4-(2-Methoxymethyl-pyrrolidin-1-yl)-butyl]-ureido}-3-(2,3,6-trifluoro-4-methyl-benzyloxy)-isothiazole-4-carboxylic acid amide;

3-(4-Chloro-2,6-difluoro-benzyloxy)-5-{3-methyl-3-[3-(4-methyl-piperazin-1-yl)-propyl]-ureido}-isothiazole-4-carboxylic acid amide;

5-{3-[4-(3-Hydroxy-pyrrolidin-1-yl)-butyl]-ureido}-3-(2,3,6-trifluoro-4-methyl-benzyloxy)-isothiazole-4-carboxylic acid amide;

3-(2,5-Difluoro-4-methyl-benzyloxy)-5-{3-methyl-3-[3-(4-methyl-piperazin-1-yl)-propyl]-ureido)-isothiazole-4-carboxylic acid amide;

5-{3-[4-(3,4-Dihydroxy-pyrrolidin-1-yl)-butyl]-ureido}-3-(2,3,6-trifluoro-4-methyl-benzyloxy)-isothiazole-4-carboxylic acid amide;

5-{3-[4-(2-Hydroxymethyl-pyrrolidin-1-yl)-butyl]-ureido}-3-(2,3,6-trifluoro-4-methyl-benzyloxy)-isothiazole-4-carboxylic acid amide;

5-{3-[4-(3-Hydroxy-piperidin-1-yl)-butyl]-ureido}-3-(2,3,6-trifluoro-4-methyl-benzyloxy)-isothiazole-4-carboxylic acid amide;

5-{3-[4-(2-Hydroxymethyl-piperidin-1-yl)-butyl]-ureido}-3-(2,3,6-trifluoro-4-methyl-benzyloxy)-isothiazole-4-carboxylic acid amide;

5-[3-(3-Cyclohexylamino-propyl)-ureido]-3-(2,3,6-trifluoro-4-methyl-benzyloxy)-isothiazole-4-carboxylic acid amide;

5-(3-{4-[Bis-(2-hydroxy-propyl)-amino]-butyl}-ureido)-3-(2,3,6-trifluoro-4-methyl-benzyloxy)-isothiazole-4-carboxylic acid amide;

5-{3-[3-(5-Methyl-2,5-diaza-bicyclo[2.2.1]hept-2-yl)-propyl]-ureido}-3-(2,3,6-trifluoro-4-methyl-benzyloxy)-isothiazole-4-carboxylic acid amide;

5-[3-(3-Imidazol-1-yl-propyl)-ureido]-3-(2,3,6-trifluoro-4-methyl-benzyloxy)-isothiazole-4-carboxylic acid amide;

3-(4-Chloro-2,3,6-trifluoro-benzyloxy)-5-{3-[4-(2-hydroxymethyl-piperidin-1-yl)-butyl]-ureido}-isothiazole-4-carboxylic acid amide;

3-(4-Chloro-2,3,6-trifluoro-benzyloxy)-5-[3-(3-hydroxy-5-pyrrolidin-1-yl-pentyl)-ureido]-isothiazole-4-carboxylic acid amide;

3-(4-Chloro-2,3,6-trifluoro-benzyloxy)-5-{3-[4-(3-hydroxy-piperidin-1-yl)-butyl]-ureido}-isothiazole-4-carboxylic acid amide;

3-(4-Chloro-2,3,6-trifluoro-benzyloxy)-5-[3-(4-hydroxy-5-piperidin-1-yl-pentyl)-ureido]-isothiazole-4-carboxylic acid amide;

3-(2,6-Difluoro-4-methyl-benzyloxy)-5-(3-methyl-ureido)-isothiazole-4-carboxylic acid amide;

5-(3-Cyclopropylmethyl-ureido)-3-(2,6-difluoro-4-methyl-benzyloxy)-isothiazole-4-carboxylic acid amide;

5-(3-Cyclobutyl-ureido)-3-(2,6-difluoro-4-methyl-benzyloxy)-isothiazole-4-carboxylic acid amide;

3-(2,6-Difluoro-4-methyl-benzyloxy)-5-[3-(3-hydroxy-propyl)-ureido]-isothiazole-4-carboxylic acid amide;

5-(3-Allyl-ureido)-3-(2,6-difluoro-4-methyl-benzyloxy)-isothiazole-4-carboxylic acid amide;

3-(2,6-Difluoro-4-methyl-benzyloxy)-5-(3-isobutyl-ureido)-isothiazole-4-carboxylic acid amide;

3-(2,6-Difluoro-4-methyl-benzyloxy)-5-{3-[2-(1-methyl-pyrrolidin-2-yl)-ethyl]-ureido}-isothiazole-4-carboxylic acid amide 3-(2,6-Difluoro-4-methyl-benzyloxy)-5-[3-(2-dimethylamino-ethyl)-ureido]-isothiazole-4-carboxylic acid amide;

3-(2,6-Difluoro-4-methyl-benzyloxy)-5-[3-(4-dimethylamino-butyl)-ureido]-isothiazole-4-carboxylic acid amide;

3-(2,6-Difluoro-4-methyl-benzyloxy)-5-[3-(7-dimethylamino-6-hydroxy-heptyl)-ureido]-isothiazole-4-carboxylic acid amide;

3-(2,6-Difluoro-4-methyl-benzyloxy)-5-{3-[4-(5-methyl-2,5-diaza-bicyclo[2.2.1]hept-2-yl)-butyl]-ureido}-isothiazole-4-carboxylic acid amide;

3-(2,6-Difluoro-4-methyl-benzyloxy)-5-[3-(3-dimethylamino-propyl)-ureido]-isothiazole-4-carboxylic acid amide;

3-(2,6-Difluoro-4-methyl-benzyloxy)-5-[3-(3-hydroxy-5-isopropylamino-pentyl)-ureido]-isothiazole-4-carboxylic acid amide;

3-(2,6-Difluoro-4-methyl-benzyloxy)-5-[3-(3-isopropylamino-propyl)-ureido]-isothiazole-4-carboxylic acid amide;

3-(2,6-Difluoro-4-methyl-benzyloxy)-5-{3-[4-(4-methyl-piperazin-1-yl)-butyl]-ureido}-isothiazole-4-carboxylic acid amide;

3-(2,6-Difluoro-4-methyl-benzyloxy)-5-{3-[5-(4-methyl-piperazin-1-yl)-pentyl]-ureido}-isothiazole-4-carboxylic acid amide;

3-(2,6-Difluoro-4-methyl-benzyloxy)-5-{3-[6-(4-methyl-piperazin-1-yl)-hexyl]-ureido}-isothiazole-4-carboxylic acid amide;

3-(2,6-Difluoro-4-methyl-benzyloxy)-5-{3-[3-hydroxy-5-(4-methyl-piperazin-1-yl)-pentyl]-ureido}-isothiazole-4-carboxylic acid amide;

3-(2,6-Difluoro-4-methyl-benzyloxy)-5-(3-{4-[4-(3-hydroxy-propyl)-piperazin-1-yl]-butyl}-ureido)-isothiazole-4-carboxylic acid amide;

3-(2,6-Difluoro-4-methyl-benzyloxy)-5-[3-(3-pyrrolidin-1-yl-propyl)-ureido]-isothiazole-4-carboxylic acid amide;

3-(4-Chloro-2,3,6-trifluoro-benzyloxy)-5-{3-[4-(3,4-dihydroxy-pyrrolidin-1-yl)-butyl]-ureido}-isothiazole-4-carboxylic acid amide;

5-{3-[4-(4-Acetyl-piperazin-1-yl)-butyl]-ureido}-3-(4-chloro-2,6-difluoro-benzyloxy)-isothiazole-4-carboxylic acid amide;

5-{3-[4-(4-Acetyl-piperazin-1-yl)-butyl]-ureido}-3-(2,5-difluoro-4-methyl-benzyloxy)-isothiazole-4-carboxylic acid amide;

3-(2,5-Difluoro-4-methyl-benzyloxy)-5-{3-[4-(3-hydroxy-piperidin-1-yl)-butyl]3-methyl-ureido}-isothiazole-4-carboxylic acid amide;

3-(4-Chloro-2,6-difluoro-benzyloxy)-5-(3-{4-[ethyl-(2-hydroxy-ethyl)-amino]-butyl}-3-methyl-ureido)-isothiazole-4-carboxylic acid amide;

3-(2,3,6-Trifluoro-4-methyl-benzyloxy)-5-ureido-isothiazole-4-carboxylic acid amide;

3-(4-Bromo-2,6-difluoro-benzyloxy)-5-{3-[3-(4-methyl-piperazin-1-yl)-propyl]-ureido}-isothiazole-4-carboxylic acid amide;

3-(4-Bromo-2,3,6-trifluoro-benzyloxy)-5-[3-(4-pyrrolidin-1-yl-butyl)-ureido]-isothiazole-4-carboxylic acid amide;

3-(2,5-Difluoro-4-methyl-benzyloxy)-5-(3-{4-[ethyl-(2-hydroxy-ethyl)-amino]-butyl}-3-methyl-ureido)-isothiazole-4-carboxylic acid amide;

3-(2,6-Difluoro-4-methyl-benzyloxy)-5-[3-(3-hydroxy-5-pyrrolidin-1-yl-pentyl)-ureido]-isothiazole-4-carboxylic acid amide;

3-(2,6-Difluoro-4-methyl-benzyloxy)-5-[3-(4-hydroxy-5-piperidin-1-yl-pentyl)-ureido]-isothiazole-4-carboxylic acid amide;

3-(2,6-Difluoro-4-methyl-benzyloxy)-5-[3-(5-hydroxy-6-piperidin-1-yl-hexyl)-ureido]-isothiazole-4-carboxylic acid amide;

3-(2,6-Difluoro-4-methyl-benzyloxy)-5-[3-(6-hydroxy-7-piperidin-1-yl-heptyl)-ureido]-isothiazole-4-carboxylic acid amide;

3-(2,6-Difluoro-4-methyl-benzyloxy)-5-[3-(4-hydroxy-5-morpholin-4-yl-pentyl)-ureido]-isothiazole-4-carboxylic acid amide;

3-(2,6-Difluoro-4-methyl-benzyloxy)-5-[3-(5-hydroxy-6-morpholin-4-yl-hexyl)-ureido]-isothiazole-4-carboxylic acid amide;

3-(2,6-Difluoro-4-methyl-benzyloxy)-5-[3-(6-hydroxy-7-morpholin-4-yl-heptyl)-ureido]-isothiazole-4-carboxylic acid amide;

3-(2,6-Difluoro-4-methyl-benzyloxy)-5-[3-(4-morpholin-4-yl-butyl)-ureido]-isothiazole-4-carboxylic acid amide;

5-(3-{4-[Bis-(2-hydroxy-ethyl)-am ino]-butyl}-ureido)-3-(2,6-difluoro-4-methyl-benzyloxy)-isothiazole-4-carboxylic acid amide;

3-(2,6-Difluoro-4-methyl-benzyloxy)-5-(3-{4-[ethyl-(2-hydroxy-ethyl)-amino]-butyl}-ureido)-isothiazole-4-carboxylic acid amide;

5-[3-(3-tert-Butylamino-propyl)-ureido]-3-(2,6-difluoro-4-methyl-benzyloxy)-isothiazole-4-carboxylic acid amide;

3-(2,6-Difluoro-4-methyl-benzyloxy)-5-{3-[4-(2-methoxymethyl-pyrrolidin-1-yl)-butyl]-ureido}-isothiazole-4-carboxylic acid amide;

3-(2,6-Difluoro-4-methyl-benzyloxy)-5-{3-[4-(3-hydroxy-pyrrolidin-1-yl)-butyl]-ureido}-isothiazole-4-carboxylic acid amide;

3-(2,6-Difluoro-4-methyl-benzyloxy)-5-{3-[4-(3,4-dihydroxy-pyrrolidin-1-yl)-butyl]-ureido}-isothiazole-4-carboxylic acid amide;

3-(2,6-Difluoro-4-methyl-benzyloxy)-5-{3-[4-(2-hydroxymethyl-pyrrolidin-1-yl)-butyl]-ureido}-isothiazole-4-carboxylic acid amide;

5-[3-(4-Imidazol-1-yl-butyl)-ureido]-3-(2,3,6-trifluoro-4-methyl-benzyloxy)-isothiazole-4-carboxylic acid amide;

3-(4-Chloro-2,3,6-trifluoro-benzyloxy)-5-{3-[4-(3,4-dihydroxy-pyrrolidin-1-yl)-butyl-ureido}-isothiazole-4-carboxylic acid amide;

3-(4-Chloro-2,3,6-trifluoro-benzyloxy)-5-[3-(4-imidazol-1-yl-butyl)-ureido]-isothiazole-4-carboxylic acid amide;

3-(4-Chloro-2,3,6-trifluoro-benzyloxy)-5-{3-[5-(4-methyl-piperazin-1-yl)-pentyl]-ureido}-isothiazole-4-carboxylic acid amide;

3-(4-Chloro-2,3,6-trifluoro-benzyloxy)-5-{3-[3-hydroxy-5-(4-methyl-piperazin-1-yl)-pentyl]-ureido}-isothiazole-4-carboxylic acid amide;

3-(4-Chloro-2,3,6-trifluoro-benzyloxy)-5-(3-{4-[4-(2-hydroxy-ethyl)-piperazin-1-yl]-butyl}-ureido)-isothiazole-4-carboxylic acid amide;

3-(4-Chloro-2,3,6-trifluoro-benzyloxy)-5-{3-[4-(5-methyl-2,5-diaza-bicyclo[2.2.1]hept-2-yl)-butyl]-ureido}-isothiazole-4-carboxylic acid amide;

3-(2,6-Difluoro-4-methyl-benzyloxy)-5-{3-[4-(3-hydroxy-piperidin-1-yl)-butyl]-ureido}-isothiazole-4-carboxylic acid amide;

3-(2,6-Difluoro-4-methyl-benzyloxy)-5-{3-[4-(2-hydroxymethyl-piperidin-1-yl)-butyl]-ureido}-isothiazole-4-carboxylic acid amide;

5-[3-(3-Cyclohexylamino-propyl)-ureido]-3-(2,6-difluoro-4-methyl-benzyloxy)-isothiazole-4-carboxylic acid amide;

3-(2,6-Difluoro-4-methyl-benzyloxy)-5-{3-[3-(5-methyl-2,5-diaza-bicyclo[2.2.1]hept-2-yl)-propyl]-ureido}-isothiazole-4-carboxylic acid amide;

3-(2,6-Difluoro-4-methyl-benzyloxy)-5-ureido-isothiazole-4-carboxylic acid amide;

3-(2,6-Difluoro-4-methyl-benzyloxy)-5-(3-ethyl-ureido)-isothiazole-4-carboxylic acid amide;

3-(4-Chloro-2,6-difluoro-benzyloxy)-5-[3-(3-cyclopropylamino-propyl)-ureido]-isothiazole-4-carboxylic acid amide;

5-[3-(3-Cyclopropylamino-propyl)-ureido]-3-(2,5-difluoro-4-methyl-benzyloxy)-isothiazole-4-carboxylic acid amide;

3-(4-Chloro-2,6-difluoro-benzyloxy)-5-(3-{3-[ethyl-(2-hydroxy-ethyl)-amino]-propyl}-ureido)-isothiazole-4-carboxylic acid amide;

3-(2,5-Difluoro-4-methyl-benzyloxy)-5-(3-{3-[ethyl-(2-hydroxy-ethyl)-amino]-propyl}-ureido)-isothiazole-4-carboxylic acid amide;

3-(4-Chloro-2,3,6-trifluoro-benzyloxy)-5-(3-{3-[4-(2-hydroxy-ethyl)-piperazin-1-yl]-propyl}-ureido)-isothiazole-4-carboxylic acid amide;

3-(4-Chloro-2,3,6-trifluoro-benzyloxy)-5-[3-(3-hydroxy-5-isopropylamino-pentyl)-ureido]-isothiazole-4-carboxylic acid amide;

3-(4-Chloro-2,6-difluoro-benzyloxy)-5-[3-(3-imidazol-1-yl-propyl)-ureido]-isothiazole-4-carboxylic acid amide;

3-(4-Chloro-2,3,6-trifluoro-benzyloxy)-5-(3-{3-[ethyl-(2-hydroxy-ethyl)-amino]-propyl}-ureido)-isothiazole-4-carboxylic acid amide;

5-{3-[2-(1-Methyl-pyrrolidin-2-yl)-ethyl]-ureido}-3-(2,3,6-trifluoro-4-methyl-benzyloxy-isothiazole)-4-carboxylic acid amide;

5-[3-(4-Dimethylamino-butyl)-ureido]-3-(2,3,6-trifluoro-4-methyl-benzyloxy)-isothiazole-4-carboxylic acid amide;

5-[3-(3-Dimethylamino-propyl)-ureido]-3-(2,3,6-trifluoro-4-methyl-benzyloxy)-isothiazole-4-carboxylic acid amide;

5-[3-(3-Hydroxy-5-isopropylamino-pentyl)-ureido]-3-(2,3,6-trifluoro-4-methyl-benzyloxy)-isothiazole-4-carboxylic acid amide;

5-[3-(3-Isopropylamino-propyl)-ureido]-3-(2,3,6-trifluoro-4-methyl-benzyloxy)-isothiazole-4-carboxylic acid amide;

5-{3-[4-(4-Methyl-piperazin-1-yl)-butyl]-ureido}-3-(2,3,6-trifluoro-4-methyl-benzyloxy)-isothiazole-4-carboxylic acid amide;

5-(3-{4-[4-(2-Hydroxy-ethyl)-piperazin-1-yl]-butyl}-ureido)-3-(2,3,6-trifluoro-4-methyl-benzyloxy)-isothiazole-4-carboxylic acid amide;

5-(3-{4-[4-(3-Hydroxy-propyl)-piperazin-1-yl]-butyl}-ureido)-3-(2,3,6-trifluoro-4-methyl-benzyloxy)-isothiazole-4-carboxylic acid amide;

5-[3-(3-Pyrrolidin-1-yl-propyl)-ureido]-3-(2,3,6-trifluoro-4-methyl-benzyloxy)-isothiazole-4-carboxylic acid amide;

5-[3-(4-Hydroxy-5-piperidin-1-yl-pentyl)-ureido]-3-(2,3,6-trifluoro-4-methyl-benzyloxy)-isothiazole-4-carboxylic acid amide;

5-(3-Ethyl-ureido)-3-(2,3,6-trifluoro-4-methyl-benzyloxy)-isothiazole-4-carboxylic acid amide;

5-(3-Methyl-ureido)-3-(2,3,6-trifluoro-4-methyl-benzyloxy)-isothiazole-4-carboxylic acid amide;

5-(3-{4-[Bis-(2-hydroxy-propyl)-amino]-butyl}-ureido)-3-(2,6-difluoro-4-methyl-benzyloxy)-isothiazole-4-carboxylic acid amide;

5-{3-[3-(4-Acetyl-piperazin-1-yl)-propyl]-ureido}-3-(2,5-difluoro-4-methyl-benzyloxy)-isothiazole-4-carboxylic acid amide;

5-{3-[3-(4-Acetyl-piperazin-1-yl)-propyl]-ureido}-3-(4-chloro-2,3,6-trifluoro-benzyloxy)-isothiazole-4-carboxylic acid amide;

3-(1,3-Difluoro-naphthalen-2-ylmethoxy)-5-(3-{4-[ethyl-(2-hydroxy-ethyl)-amino]-butyl}-ureido)-isothiazole-4-carboxylic acid amide'

5-{3-[3-(4-Acetyl-piperazin-1-yl)-propyl]-ureido}-3-(4-chloro-2,6-difluoro-benzyloxy)-isothiazole-4-carboxylic acid amide;

5-{3-[4-(4-Acetyl-piperazin-1-yl)-butyl]-ureido}-3-(4-chloro-2,3,6-trifluoro-benzyloxy)-isothiazole-4-carboxylic acid amide;

3-(4-Chloro-2,3,6-trifluoro-benzyloxy)-5-[3-(3-imidazol-1-yl-propyl)-ureido]-isothiazole-4-carboxylic acid amide;

5-[3-(2-Amino-ethyl)-ureido]-3-(2,3,6-trifluoro-4-methyl-benzyloxy)-isothiazole-4-carboxylic acid amide;

5-[3-(4-Amino-butyl)-ureido]-3-(2,3,6-trifluoro-4-methyl-benzyloxy)-isothiazole-4-carboxylic acid amide;

5-[3-(5-Amino-pentyl)-ureido]-3-(2,3,6-trifluoro-4-methyl-benzyloxy)-isothiazole-4-carboxylic acid amide;

5-[3-(6-Amino-hexyl)-ureido]-3-(2,3,6-trifluoro-4-methyl-benzyloxy)-isothiazole-4-carboxylic acid amide;

5-[3-(7-Amino-heptyl)-ureido]-3-(2,3,6-trifluoro-4-methyl-benzyloxy)-isothiazole-4-carboxylic acid amide;

3-(1,3-Difluoro-naphthalen-2-ylmethoxy)-5-{3-[2-(1-methyl-pyrrolidin-2-yl)-ethyl]-ureido}-isothiazole-4-carboxylic acid amide;

3-(1,3-Difluoro-naphthalen-2-ylmethoxy)-5-{3-[4-(2-hydroxymethyl-pyrrolidin-1-yl)-butyl]-ureido}-isothiazole-4-carboxylic acid amide;

3-(1,3-Difluoro-naphthalen-2-ylmethoxy)-5-{3-[3-(5-methyl-2,5-diaza-bicyclo[2.2.1]hept-2-yl)-propyl]-ureido}-isothiazole-4-carboxylic acid amide;

3-(1,3-Difluoro-naphthalen-2-ylmethoxy)-5-[3-(4-pyrrolidin-1-yl-butyl)-ureido]-isothiazole-4-carboxylic acid amide;

3-(1,3-Difluoro-naphthalen-2-ylmethoxy)-5-{3-[3-(4-methyl-piperazin-1-yl)-propyl]-ureido}-isothiazole-4-carboxylic acid amide;

5-(3-{4-[Ethyl-(2-hydroxy-ethyl)-amino]-butyl}-ureido)-3-(2,3,6-trifluoro-4-methyl-benzyloxy)-isothiazole-4-carboxylic acid amide;

5-{3-[4-(3-Hydroxy-piperidin-1-yl)-butyl]-ureido}-3-(2,3,6-trifluoro-4-methyl-benzyloxy)-isothiazole-4-carboxylic acid amide;

5-[3-(3-tert-Butylamino-propyl)-ureido]-3-(2,3,6-trifluoro-4-methyl-benzyloxy)-isothiazole-4-carboxylic acid amide;

5-{3-[4-(3-Hydroxy-pyrrolidin-1-yl)-butyl]-ureido}-3-(2,3,6-trifluoro-4-methyl-benzyloxy)-isothiazole-4-carboxylic acid amide;

5-{3-[4-(3,4-Dihydroxy-pyrrolidin-1-yl)-butyl]-ureido}-3-(2,3,6-trifluoro-4-methyl-benzyloxy)-isothiazole-4-carboxylic acid amide;

5-{3-[4-(2-Hydroxymethyl-pyrrolidin-1-yl)-butyl]-ureido}-3-(2,3,6-trifluoro-4-methyl-benzyloxy)-isothiazole-4-carboxylic acid amide;

5-{3-[4-(2-Hydroxymethyl-piperidin-1-yl)-butyl]-ureido}-3-(2,3,6-trifluoro-4-methyl-benzyloxy)-isothiazole-4-carboxylic acid amide;

3-(2,6-Difluoro-4-methyl-benzyloxy)-5-(3-methyl-ureido)-isothiazole-4-carboxylic acid amide;

3-(2,6-Difluoro-4-methyl-benzyloxy)-5-{3-[2-(1-methyl-pyrrolidin-2-yl)-ethyl]-ureido}-isothiazole-4-carboxylic acid amide;

3-(2,6-Difluoro-4-methyl-benzyloxy)-5-[3-(2-dimethylamino-ethyl)-ureido]-isothiazole-4-carboxylic acid amide;

3-(2,6-Difluoro-4-methyl-benzyloxy)-5-[3-(4-dimethylamino-butyl)-ureido]-isothiazole-4-carboxylic acid amide;

3-(2,6-Difluoro-4-methyl-benzyloxy)-5-{3-[4-(5-methyl-2,5-diaza-bicyclo[2.2.1]hept-2-yl)-butyl]-ureido}-isothiazole-4-carboxylic acid amide;

5-(3-{4-[Bis-(2-hydroxy-ethyl)-amino]-butyl}-ureido)-3-(2,3,6-trifluoro-4-methyl-benzyloxy)-isothiazole-4-carboxylic acid amide;

5-{3-[3-(5-Methyl-2,5-diaza-bicyclo[2.2.1]hept-2-yl)-propyl]-ureido}-3-(2,3,6-trifluoro-4-methyl-benzyloxy)-isothiazole-4-carboxylic acid amide;

3-(2,6-Difluoro-4-methyl-benzyloxy)-5-[3-(3-dimethylamino-propyl)-ureido]-isothiazole-4-carboxylic acid amide;

3-(2,6-Difluoro-4-methyl-benzyloxy)-5-[3-(3-hydroxy-5-isopropylamino-pentyl)-ureido]-isothiazole-4-carboxylic acid amide;

5-[3-(3-Cyclohexylamino-propyl)-ureido]-3-(2,3,6-trifluoro-4-methyl-benzyloxy)-isothiazole-4-carboxylic acid amide;

3-(2,6-Difluoro-4-methyl-benzyloxy)-5-[3-(3-isopropylamino-propyl)-ureido]-isothiazole-4-carboxylic acid amide;

5-[3-(3-Amino-propyl)-ureido]-3-(2,3,6-trifluoro-4-methyl-benzyloxy)-isothiazole-4-carboxylic acid amide;

5-{3-[2-(2-Amino-ethoxy)-ethyl]-ureido}-3-(2,3,6-trifluoro-4-methyl-benzyloxy)-isothiazole-4-carboxylic acid amide;

5-[3-(4-Pyrrolidin-1-yl-butyl)-ureido]-3-(2,3,6-trifluoro-4-methyl-benzyloxy)-isothiazole-4-carboxylic acid amide;

5-{3-[3-(4-Methyl-piperazin-1-yl)-propyl]-ureido}-3-(2,3,6-trifluoro-4-methyl-benzyloxy)-isothiazole-4-carboxylic acid amide;

5-[3-(4-Amino-butyl)-ureido]-3-(4-chloro-2,6-difluoro-benzyloxy)-isothiazole-4-carboxylic acid amide;5-[3-(7-Amino-heptyl)-ureido]-3-(4-chloro-2,6-difluoro-benzyloxy)-isothiazole-4-carboxylic acid amide;

5-[3-(5-Amino-pentyl)-ureido]-3-(4-chloro-2,6-difluoro-benzyloxy)-isothiazole-4-carboxylic acid amide;5-[3-(4-Amino-butyl)-ureido]-3-(2,3,6-trifluoro-4-methyl-benzyloxy)-isothiazole-4-carboxylic acid amide;

5-[3-(3-Azepan-1-yl-propyl)-ureido]-3-(2,3,6-trifluoro-4-methyl-benzyloxy)-isothiazole-4-carboxylic acid amide;

5-[3-(3-Diethylamino-propyl)-ureido]-3-(2,3,6-trifluoro-4-methyl-benzyloxy)-isothiazole-4-carboxylic acid amide;

5-[3-(3-Methylamino-propyl)-ureido]-3-(2,3,6-trifluoro-4-methyl-benzyloxy)-isothiazole-4-carboxylic acid amide;

5-{3-[3-(2-Methyl-piperidin-1-yl)-propyl]-ureido}-3-(2,3,6-trifluoro-4-methyl-benzyloxy)-isothiazole-4-carboxylic acid amide;

3-(2,5-Difluoro-4-methyl-benzyloxy)-5-{3-[4-(pyridin-2-ylamino)-butyl]-ureido}-isothiazole-4-carboxylic acid amide;

3-(2,5-Difluoro-4-methyl-benzyloxy)-5-{3-[3-(pyridin-2-ylamino)-propyl]-ureido}-isothiazole-4-carboxylic acid amide;

5-[3-(6-Amino-hexyl)-ureido]-3-(4-chloro-2,6-difluoro-benzyloxy)-isothiazole-4-carboxylic acid amide;

3-(4-Chloro-2,6-difluoro-benzyloxy)-5-{3-[4-(pyridin-2-ylamino)-butyl]-ureido}-isothiazole-4-carboxylic acid amide;

3-(4-Chloro-2,3,6-trifluoro-benzyloxy)-5-{3-[4-(pyridin-2-ylamino)-butyl]-ureido}-isothiazole-4-carboxylic acid amide;

3-(4-Chloro-2,3,6-trifluoro-benzyloxy)-5-{3-[3-(pyridin-2-ylamino)-propyl]-ureido}-isothiazole-4-carboxylic acid amide;

3-(4-Chloro-2,6-difluoro-benzyloxy)-5-{3-[3-(pyridin-2-ylamino)-propyl]-ureido}-isothiazole-4-carboxylic acid amide;

3-(4-Chloro-2,6-difluoro-benzyloxy)-5-[3-(4-cyclopropylamino-butyl)-ureido]-isothiazole-4-carboxylic acid amide;

5-[3-(3-Amino-propyl)-3-methyl-ureido]-3-(2,3,6-trifluoro-4-methyl-benzyloxy)-isothiazole-4-carboxylic acid amide;

3-(3-Chloro-2,6-difluoro-4-methyl-benzyloxy)-5-{3-[2-(1-methyl-pyrrolidin-2-yl)-ethyl]-ureido}-isothiazole-4-carboxylic acid amide;

3-(3-Chloro-2,6-difluoro-4-methyl-benzyloxy)-5-[3-(3-dimethylamino-propyl)-ureido]-isothiazole-4-carboxylic acid amide;

3-(3-Chloro-2,6-difluoro-4-methyl-benzyloxy)-5-[3-(4-dimethylamino-butyl)-ureido]-isothiazole-4-carboxylic acid amide;

5-[3-(2-Amino-ethyl)-ureido]-3-(4-chloro-2,6-difluoro-benzyloxy)-isothiazole-4-carboxylic acid amide;

5-[3-(2-Amino-ethyl)-ureido]-3-(2,5-difluoro-4-methyl-benzyloxy)-isothiazole-4-carboxylic acid amide;

5-[3-(7-Amino-heptyl)-ureido]-3-(2,5-difluoro-4-methyl-benzyloxy)-isothiazole-4-carboxylic acid amide;

5-[3-(3-Amino-propyl)-ureido]-3-(2,5-difluoro-4-methyl-benzyloxy)-isothiazole-4-carboxylic acid amide;

3-(2,5-Difluoro-4-methyl-benzyloxy)-5-{3-[4-(pyridin-4-ylamino)-butyl]-ureido}-isothiazole-4-carboxylic acid amide;

3-(4-Chloro-2,6-difluoro-benzyloxy)-5-{3-[4-(pyridin-4-ylamino)-butyl]-ureido}-isothiazole-4-carboxylic acid amide;

3-(4-Chloro-2,3,6-trifluoro-benzyloxy)-5-{3-[4-(pyridin-4-ylamino)-butyl]-ureido}-isothiazole-4-carboxylic acid amide.

The invention claimed is:

1. A compound of the formula

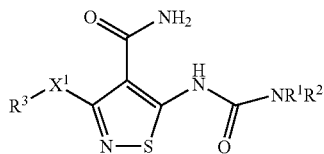

or a pharmaceutically acceptable salt or prodrug thereof, wherein:
wherein $X^1$ is O or S;
$R^1$ is $C_2$-$C_{10}$ alkynyl, —C(O)($C_1$-$C_{10}$ alkyl), —$(CH_2)_t(C_6$-$C_{10}$ aryl), —C(O)($CH_2)_t(C_6$-$C_{10}$ aryl), or —C(O)($CH_2$) $_t$(5-10 membered heterocyclic), wherein t is an integer from 0 to 5; said alkyl group optionally includes 1 or 2 hetero moieties selected from O, S and —N($R^6$)— with the proviso that two O atoms, two S atoms, or an O and S atom are not attached directly to each other; said aryl and heterocyclic $R^1$ groups are optionally fused to a $C_6$-$C_{10}$ aryl group, a $C_5$-$C_8$ saturated cyclic group, or a 5-10 membered heterocyclic group; 1 or 2 carbon atoms in the foregoing heterocyclic moieties are optionally substituted by an oxo (=O) moiety; the —$(CH_2)_t$— moieties of the foregoing $R^1$ groups optionally include a carbon-carbon double or triple bond where t is an integer from 2 to 5; and the foregoing $R^1$ groups, are optionally substituted by 1 to 3 $R^4$ groups;

$R^2$ is selected from the list of substituents provided in the definition of $R^1$, —$SO_2(CH_2)_t(C_6$-$C_{10}$ aryl), —$SO_2(CH_2)_t$(5-10 membered heterocyclic), and —$OR^5$, t is an integer ranging from 0 to 5, the —$(CH_2)_t$— moieties of the foregoing $R^2$ groups optionally include a carbon-carbon double or triple bond where t is an integer from 2 to 5, and the foregoing $R^2$ groups are optionally substituted by 1 to 3 $R^4$ groups;

or $R^1$ and $R^2$ may be taken together with the nitrogen to which each is attached to form a 4-10 membered saturated monocyclic or polycyclic ring or a 5-10 membered heteroaryl ring, wherein said saturated and heteroaryl rings eoptionally include 1 or 2 heteroatoms selected from O, S and —N($R^6$)— in addition to the nitrogen to which $R^1$ and $R^2$ are attached, said —N($R^6$)— is optionally =N— or —N= where $R^1$ and $R^2$ are taken together as said heteroaryl group, said saturated ring optionally may be partially unsaturated by including 1 or 2 carbon-carbon double bonds, and said saturated and heteroaryl rings, including the $R^6$ group of said —N($R^6$), are optionally substituted by 1 to 3 $R^4$ groups;

$R^3$ is H, $C_1$-$C_{10}$ alkyl, $C_2$-$C_{10}$ alkenyl, $C_2$-$C_{10}$ alkynyl, or —$(CH_2)_t(C_5$-$C_{10}$ membered heterocyclic), wherein t is an integer from 0 to 5; said alkyl group optionally includes 1 or 2 hetero moieties selected from O, S and —N($R^6$)— with the proviso that two O atoms, two S atoms, or an O and S atom are not attached directly to each other; said heterocyclic $R^3$ group is optionally fused to a $C_6$-$C_{10}$ aryl group, a $C_5$-$C_8$ saturated cyclic group, or a 5-10 membered heterocyclic group; 1 or 2 carbon atoms in the foregoing heterocyclic moieties are optionally substituted by an oxo (=O) moiety; the —$(CH_2)_t$— moieties of the foregoing $R^3$ groups optionally include a carbon-carbon double or triple bond where t is an integer from 2 to 5, and the foregoing $R^3$ groups are optionally substituted by 1 to 5 $R^4$ groups;

each $R^4$ is independently selected from $C_1$-$C_{10}$ alkyl, $C_2$-$C_{10}$ alkenyl, $C_2$-$C_{10}$ alkynyl, halo, cyano, nitro, trifluoromethyl, trifluoromethoxy, azido, —$OR^5$, —C(O)$R^5$, —C(O)$OR^5$, —$NR^6$C(O)$OR^5$, —OC(O)$R^5$, —$NR^6SO_2R^5$, —$SO_2NR^5R^6$, —$NR^6$C(O)$R^5$, —C(O)$NR^5R^6$, —$NR^5R^6$, —S(O)$_jR^7$ wherein j is an integer ranging from 0 to 2, —$SO_3H$, —$NR^5(CR^6R^7)_tOR^6$, —$(CH_2)_t(C_6$-$C_{10}$ aryl), —$SO_2(CH_2)_t(C_6$-$C_{10}$ aryl), —S$(CH_2)_t(C_6$-$C_{10}$ aryl), —O($CH_2$) $_t(C_6$-$C_{10}$ aryl), —$(CH_2)_t$(5-10 membered heterocyclic), and —$(CR^6R^7)_mOR^6$, wherein m is an integer from 1 to 5 and t is an integer from 0 to 5; said alkyl group optionally contains 1 or 2 hetero moieties selected from O, S and —N($R^6$)— with the proviso that two O atoms, two S atoms, or an O and S atom are not attached directly to each other; said aryl and heterocyclic $R^4$ groups are optionally fused to a $C_6$-$C_{10}$ aryl group, a $C_5$-$C_8$ saturated cyclic group, or a 5-10 membered heterocyclic group; 1 or 2 carbon atoms in the foregoing heterocyclic moieties are optionally substituted by an oxo (=O) moiety; and the alkyl, aryl and heterocyclic moieties of the foregoing $R^4$ groups are optionally substituted by 1 to 3 substituents independently selected from halo, cyano, nitro, trifluoromethyl, trifluoromethoxy, azido, —$NR^6SO_2R^5$, —$SO_2NR^5R^6$, —$C(O)R^5$, —$C(O)OR^5$, —$OC(O)R^5$, —$NR^6C(O)R^5$, —$C(O)NR^5R^6$, —$NR^5R^6$, —$(CR^6R^7)_mOR^6$ wherein m is an integer from 1 to 5, —$OR^5$ and the substituents listed in the definition of $R^5$;

each $R^5$ is independently selected from H, $C_1$-$C_{10}$ alkyl, —$(CH_2)_t(C_6$-$C_{10}$ aryl), and —$(CH_2)_t$(5-10 membered heterocyclic), wherein t is an integer from 0 to 5; said alkyl group optionally includes 1 or 2 hetero moieties selected from O, S and —$N(R^6)$— with the proviso that two O atoms, two S atoms, or an O and S atom are not attached directly to each other; said aryl and heterocyclic $R^5$ groups are optionally fused to a $C_6$-$C_{10}$ aryl group, a $C_5$-$C_8$ saturated cyclic group, or a 5-10 membered heterocyclic group; and the foregoing $R^5$ subsituents, except H, are optionally substituted by 1 to 3 substituents independently selected from halo, cyano, nitro, trifluoromethyl, trifluoromethoxy, azido, —$C(O)R^6$, —$C(O)OR^6$, —$CO(O)R^6$, —$NR^6C(O)R^7$, —$C(O)NR^6R^7$, —$NR^6R^7$, hydroxy, $C_1$-$C_6$ alkyl, and, each $R^6$ and $R^7$ is independently H or $C_1$-$C_6$ alkyl.

2. A pharmaceutical composition comprises a therapeutically effective amount of a compound according to claim 1 and a pharmaceutically acceptable carrier.

* * * * *